US010217045B2

(12) United States Patent
Lal et al.

(10) Patent No.: US 10,217,045 B2
(45) Date of Patent: Feb. 26, 2019

(54) COMPUTATION DEVICES AND ARTIFICIAL NEURONS BASED ON NANOELECTROMECHANICAL SYSTEMS

(71) Applicant: Cornell University, Ithaca, NY (US)

(72) Inventors: Amit Lal, Ithaca, NY (US); Serhan Ardanuc, Ithaca, NY (US); Jason T. Hoople, Ithaca, NY (US); Justin C. Kuo, Ithaca, NY (US)

(73) Assignee: Cornell University, Ithaca, NY (US)

( * ) Notice: Subject to any disclaimer, the term of this patent is extended or adjusted under 35 U.S.C. 154(b) by 362 days.

(21) Appl. No.: 14/273,540

(22) Filed: May 8, 2014

(65) Prior Publication Data

US 2014/0355381 A1 Dec. 4, 2014
US 2018/0174021 A9 Jun. 21, 2018

Related U.S. Application Data

(63) Continuation-in-part of application No. PCT/US2013/050772, filed on Jul. 16, 2013.
(Continued)

(51) Int. Cl.
*B06B 1/06* (2006.01)
*G06N 3/04* (2006.01)
(Continued)

(52) U.S. Cl.
CPC ............. *G06N 3/04* (2013.01); *B81B 3/0021* (2013.01); *G01S 7/521* (2013.01); *G01S 15/02* (2013.01);
(Continued)

(58) Field of Classification Search
USPC .......................................... 367/140
See application file for complete search history.

(56) References Cited

U.S. PATENT DOCUMENTS 4,827,229 A * 5/1989 Sabet-Peyman ....... G01R 23/17
333/133
7,125,383 B2 * 10/2006 Hoctor ................. A61B 8/4236
600/438
(Continued)

OTHER PUBLICATIONS

Fesenko, Pavlo. "Capacitive micromachined ultrasonic transducer (cMUT) for biometric applications." (2012).*
(Continued)

*Primary Examiner* — Isam A Alsomiri
*Assistant Examiner* — Jonathan D Armstrong
(74) *Attorney, Agent, or Firm* — Perkins Coie LLP

(57) ABSTRACT

Techniques, systems, and devices are described for implementing for implementing computation devices and artificial neurons based on nanoelectromechanical (NEMS) systems. In one aspect, a nanoelectromechanical system (NEMS) based computing element includes: a substrate; two electrodes configured as a first beam structure and a second beam structure positioned in close proximity with each other without contact, wherein the first beam structure is fixed to the substrate and the second beam structure is attached to the substrate while being free to bend under electrostatic force. The first beam structure is kept at a constant voltage while the other voltage varies based on an input signal applied to the NEMS based computing element.

7 Claims, 53 Drawing Sheets

Related U.S. Application Data

(60) Provisional application No. 61/672,214, filed on Jul. 16, 2012, provisional application No. 61/821,195, filed on May 8, 2013, provisional application No. 61/932,234, filed on Jan. 27, 2014.

(51) Int. Cl.
| | | |
|---|---|---|
| B81B 3/00 | (2006.01) | |
| G06K 9/00 | (2006.01) | |
| G01S 7/521 | (2006.01) | |
| G01S 15/02 | (2006.01) | |
| G06N 3/063 | (2006.01) | |
| H01J 49/02 | (2006.01) | |
| H01H 1/00 | (2006.01) | |
| G01S 15/89 | (2006.01) | |
| G01S 7/52 | (2006.01) | |

(52) U.S. Cl.
CPC ......... G06K 9/0002 (2013.01); G06N 3/0635 (2013.01); H01J 49/025 (2013.01); *B81B 2201/018* (2013.01); *B81B 2201/0214* (2013.01); *B81B 2201/0285* (2013.01); *B81B 2203/04* (2013.01); *G01S 7/52079* (2013.01); *G01S 15/8925* (2013.01); *H01H 1/0094* (2013.01)

(56) References Cited

U.S. PATENT DOCUMENTS

| | | | | |
|---|---|---|---|---|
| 7,425,199 | B2* | 9/2008 | Hoctor | A61B 8/4236 600/438 |
| 7,443,765 | B2* | 10/2008 | Thomenius | B06B 1/0292 367/153 |
| 2003/0173408 | A1* | 9/2003 | Mosher, Jr. | A61B 5/117 235/492 |
| 2004/0052406 | A1* | 3/2004 | Brooks | G06K 9/00 382/115 |
| 2005/0143640 | A1* | 6/2005 | Hoctor | A61B 8/4236 600/407 |
| 2005/0154299 | A1* | 7/2005 | Hoctor | A61B 8/4236 600/437 |
| 2005/0237858 | A1* | 10/2005 | Thomenius | B06B 1/0292 367/155 |
| 2006/0114081 | A1 | 6/2006 | Furuhata et al. | |
| 2006/0283249 | A1 | 12/2006 | Liu et al. | |
| 2007/0073150 | A1 | 3/2007 | Gopalsami et al. | |
| 2008/0042517 | A1 | 2/2008 | Stokes et al. | |
| 2008/0168638 | A1 | 7/2008 | Bhattacharjee et al. | |
| 2012/0147698 | A1* | 6/2012 | Wong | B60B 1/02 367/7 |
| 2014/0219062 | A1* | 8/2014 | Rothberg | B81B 3/0021 367/135 |
| 2016/0117541 | A1* | 4/2016 | Lu | G06K 9/0002 382/124 |
| 2018/0055369 | A1* | 3/2018 | Burns | A61B 5/0095 |
| 2018/0218859 | A1* | 8/2018 | Ligtenberg | G06K 9/00375 |

OTHER PUBLICATIONS

Wang, Shengxiang, et al. "SU-8-based nanocomposites for acoustical matching layer." IEEE transactions on ultrasonics, ferroelectrics, and frequency control 56.7 (2009): 1483-1489.*
NDT. Characteristics of Piezoelectric Transducers. [URL: https://web.archive.org/web/20050115000000*/https://www.nde-ed.org/EducationResources/CommunityCollege/Ultrasonics/EquipmentTrans/characteristicspt.htm]. May 5th, 2005.*
Ergun, A. S., Temelkuran, B., Ozbay, E., & Atalar, A. (2001). A new detection method for capacitive micromachined ultrasonic transducers. ieee transactions on ultrasonics, ferroelectrics, and frequency control, 48(4), 932-942. (Year: 2001).*
Liao et al., "A micromirror module using a MEMS digital-to-analog converter and its application for optical surface profiling", Journal of Micromechanics and Microengineering, v 20, n. 10, Mar. 9, 2010.

* cited by examiner

10 — Conventional Integrated Circuit Design

20 — Acoustic Communications Integrated Circuit

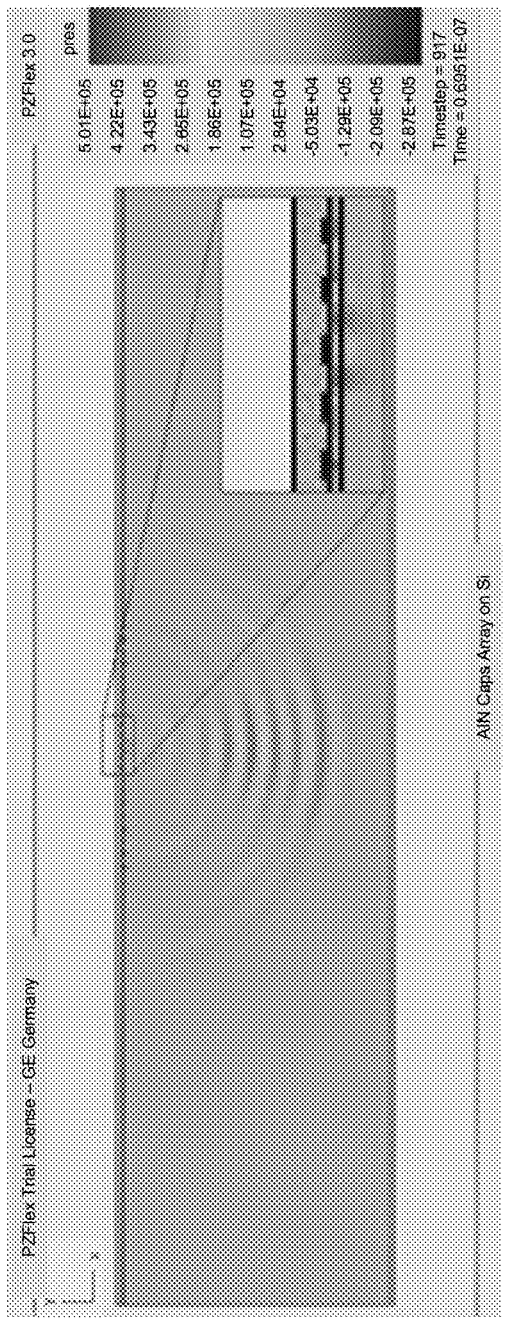
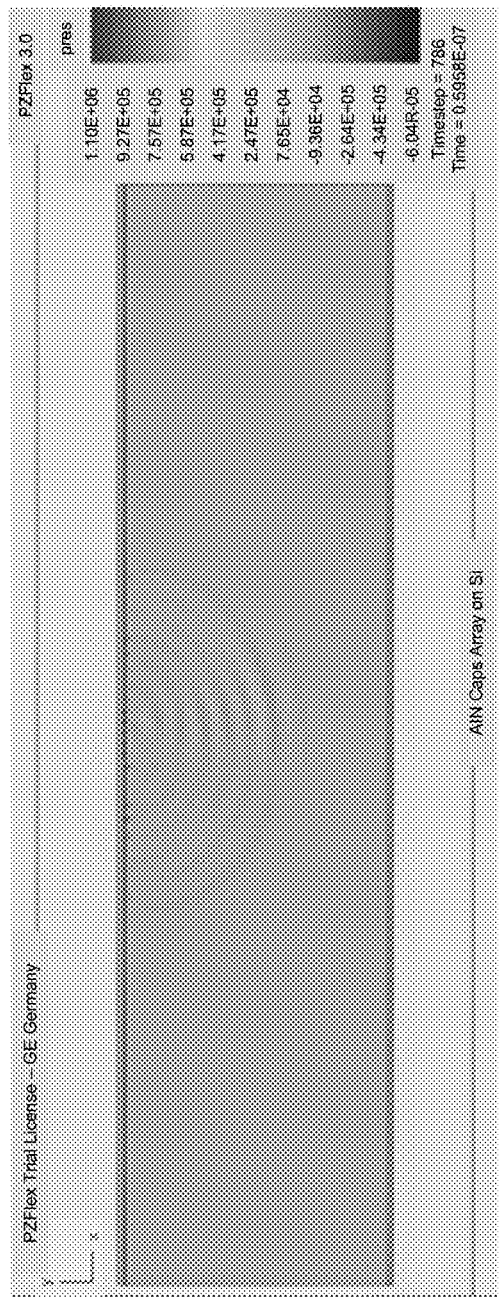
FIG. 3A
FIG. 3B

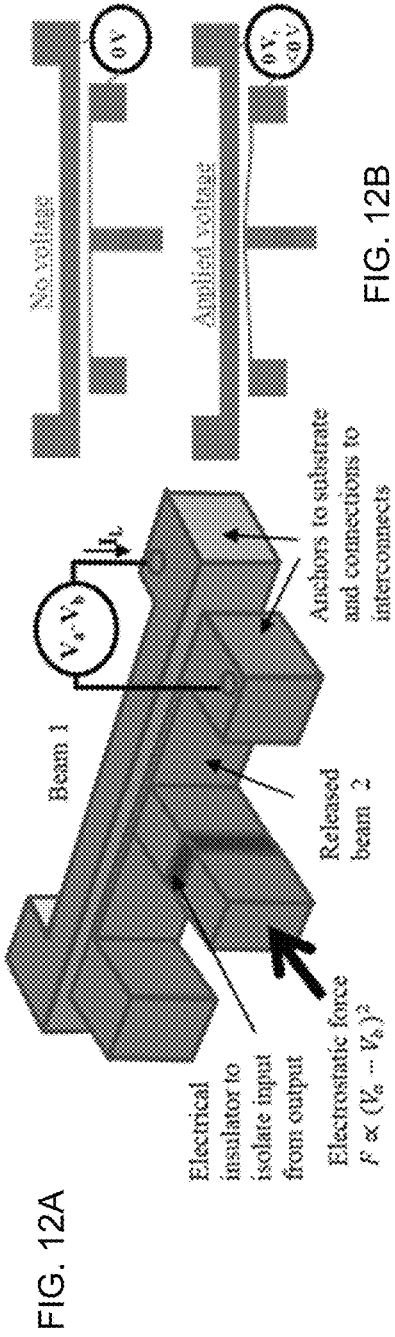
FIG. 12A
FIG. 12B
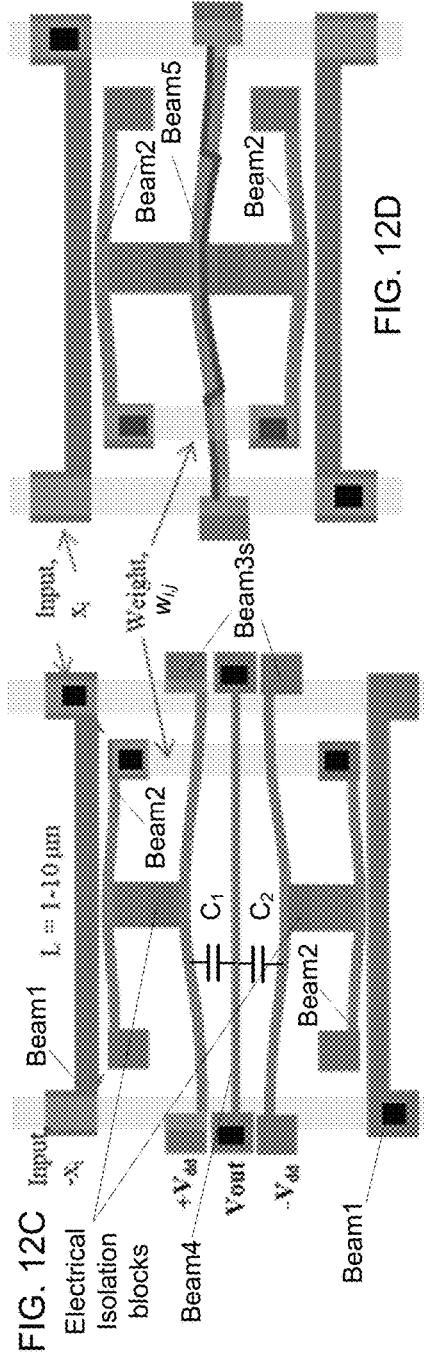
FIG. 12C
FIG. 12D
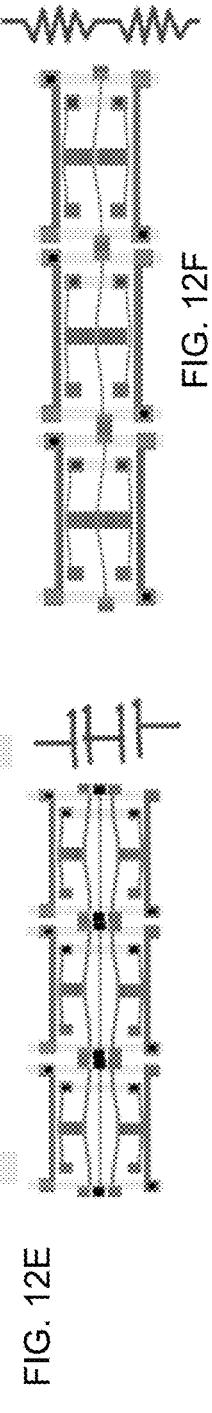
FIG. 12E
FIG. 12F

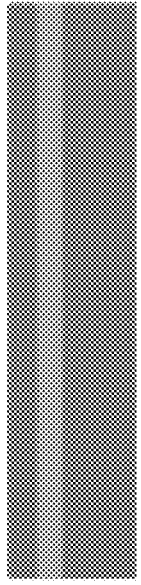 Starting with SOI Wafer

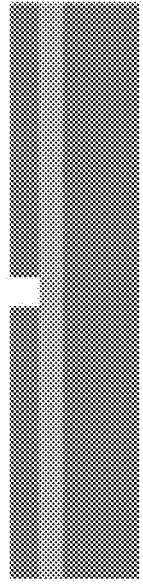 Lithographically define and etch a hole into the silicon down to the Silicon Dioxide layer

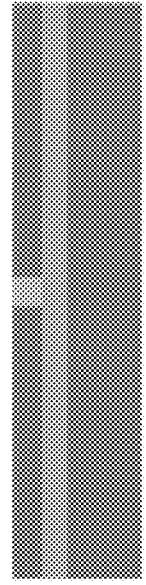 Atomic layer deposition of Nitride layer across the entire surface until the plug is filled. Use CMP (Chemical Mechanical Polishing) to smooth back to the original silicon.

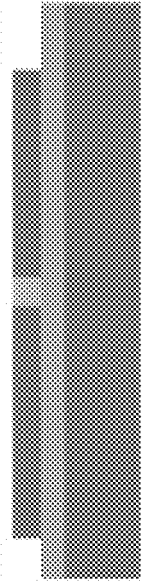 Lithographically define and etch through the silicon

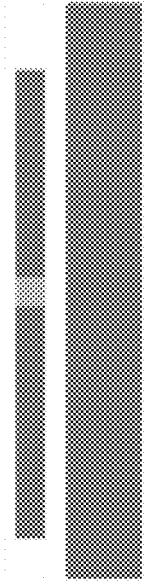 Use Vapor HF to etch away the Silicon Dioxide

FIG. 12M

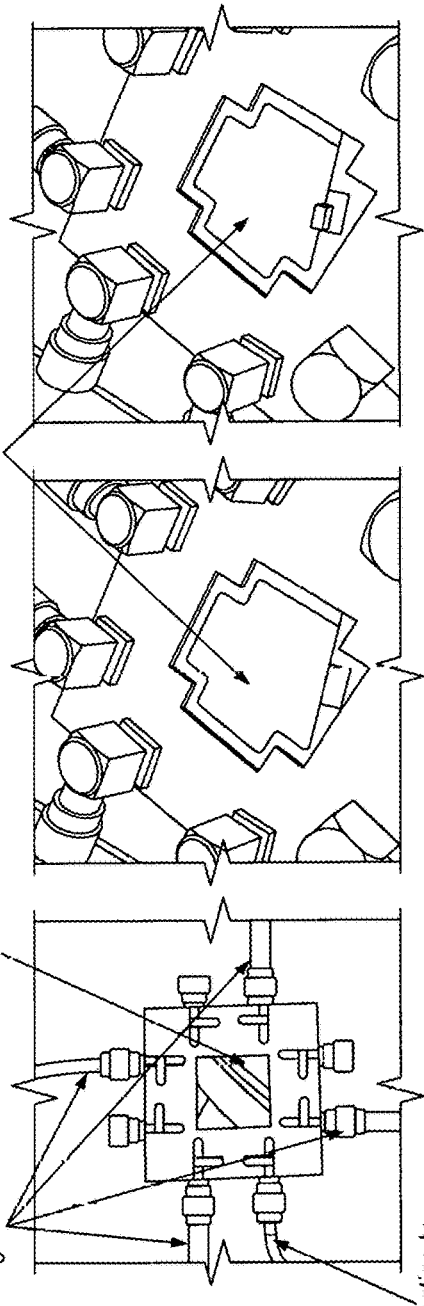
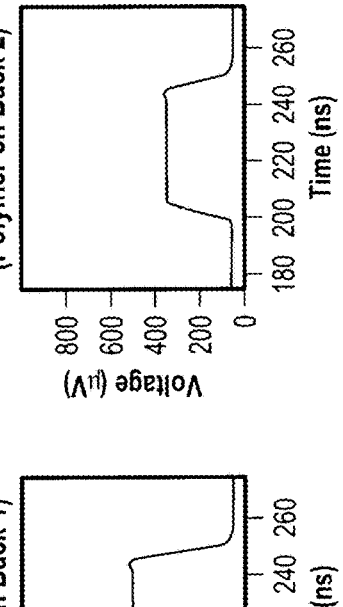
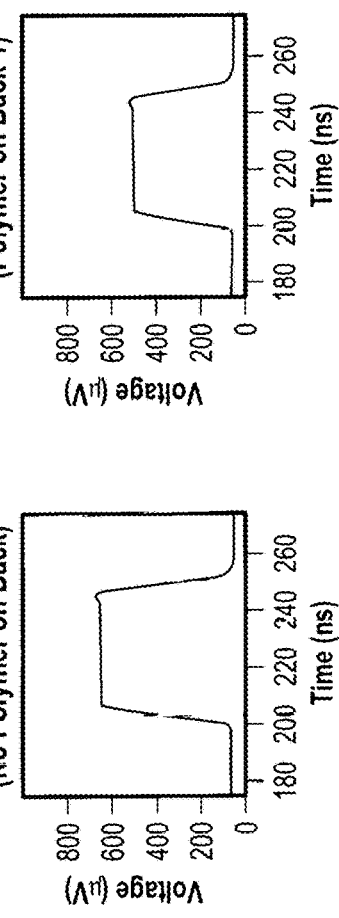
FIG. 42a
FIG. 42b
FIG. 42c
FIG. 42d
FIG. 42e
FIG. 42f

COMPUTATION DEVICES AND ARTIFICIAL NEURONS BASED ON NANOELECTROMECHANICAL SYSTEMS

PRIORITY CLAIM

Under 35 U.S.C. § 120, this application is a continuation-in-part of International Patent Application No. PCT/US2013/050772 entitled "INTEGRATED CIRCUITS HAVING INTEGRATED ACOUSTIC COMMUNICATION LINKS," filed on Jul. 16, 2013, and, under 35 U.S.C. § 119(e), claims the benefit of priority of U.S. Provisional Patent Application No. 61/821,195 entitled "COMPUTATION DEVICES AND ARTIFICIAL NEURONS BASED ON NANOELECTROMECHANICAL SYSTEMS," filed on May 8, 2013 and U.S. Provisional Patent Application No. 61/932,234 entitled "INTEGRATED CIRCUITS BASED BIOSENSORS," filed on Jan. 27, 2014. The entire content of the before-mentioned patent applications is incorporated by reference as part of the disclosure of this application.

STATEMENT OF GOVERNMENT SUPPORT

This invention was made with government support under Grant No. N66001-12-C-2009, awarded by the Intelligence Advanced Research Projects Activity (IARPA) Trusted Integrated Chips (TIC) program. The government has certain rights in this invention.

TECHNICAL FIELD

This patent document relates to semiconductor technologies.

BACKGROUND

Semiconductor fabrication and nanotechnology provide techniques or processes for fabricating structures, devices, and systems with features at a micro or nano scale, e.g., structures in a range of one to hundreds of nanometers in some applications. Integrated circuits and microprocessors are examples of such structures, devices and systems.

SUMMARY

Techniques, systems, and devices are described for implementing for implementing computation devices and artificial neurons based on nanoelectromechanical (NEMS) systems.

In one aspect, a nanoelectromechanical system (NEMS) based computing element includes: a substrate; two electrodes configured as a first beam structure and a second beam structure positioned in close proximity with each other without contact, wherein the first beam structure is fixed to the substrate and the second beam structure is attached to the substrate while being free to bend under electrostatic force. The first beam structure is kept at a constant voltage while the other voltage varies based on an input signal applied to the NEMS based computing element.

In another aspect, an artificial neural network includes: a plurality of nanoelectromechanical system (NEMS) based computing elements interfaced with one another and forming synaptic nodes, the NEMS based computing elements including: a substrate; and two electrodes configured as a first beam structure and a second beam structure, wherein the first beam structure is fixed to the substrate and the second beam structure is attached to the substrate while being free to bend under electrostatic force. The first beam structure is kept at a constant voltage while the other voltage varies based on an input signal applied to the NEMS based computing element.

In another aspect, a device based on nanoelectromechanical system (NEMS) elements includes: a substrate; nanoelectromechanical system (NEMS) elements formed over the substrate, each NEMS element including two electrodes configured as a first beam structure and a second beam structure positioned in close proximity with each other without contact to allow for relative motion therebetween under an electrostatic force in response to an electrical signal applied to the NEMS element; and an array of SONAR (Sound Navigation and Ranging) devices formed over the substrate, each SONAR device operable to produce a sonic signal directed to the NEMS elements so that sonic signals from the SONAR devices form sonic communication links within the NMES elements.

In another aspect, a nanoelectromechanical system (NEMS) based multiplier element includes: a substrate; a first pair of electrodes disposed on the substrate and configured as a first beam structure and a second beam structure positioned in close proximity with each other without contact, wherein the first beam structure is fixed to the substrate and the second beam structure is attached to the substrate while being free to bend under electrostatic force; a second pair of electrodes disposed on the substrate mirroring the first pair of electrodes and configured as a third beam structure and a fourth beam structure positioned in close proximity with each other without contact, wherein the third beam structure is fixed to the substrate and the fourth beam structure is attached to the substrate while being free to bend under electrostatic force; wherein the first pair of electrodes and the second pair of electrodes mirror each other such that the second and fourth beam structures are on the inside of the combined structure. The multiplier element also includes a fifth beam structure disposed on the substrate between the second and fourth beam structures and serves as an output electrode. The first beam structure is coupled to a first voltage, the third beam structure is coupled to a second voltage that is the negative version of the first voltage, wherein the second and fourth beam structures are coupled to a third voltage. The fifth beam structure is configured to output a fourth voltage which is proportional to the product of the first voltage and the third voltage.

In another aspect, an ion-gas sensor device includes: a substrate including an array of pillars and troughs; a micro-fan component including a first stack and a second stack of layers of a piezoelectric composite material formed on the pillars of the substrate and protruding over the troughs, the first stack of layers to sense the flow of ions in a gas and the second stack of layers actuate to drive the ions to a detection region of the device at a controlled flow rate; a layer of a radioactive material formed in the trough of the substrate to ionize the gas when flowed above the layer; and an array of electrodes formed in the detection region to detect ion mobility of the ions of the gas In another aspect, an chip-size gas analyzer includes: a chipscale ionization source configured to generate ions of the target compounds in the gas flowing through the sensor; a gas pump module configured to pump the ions of the target compounds into an area of chemical sensing; and a detection module configured to detect and identify target compounds.

In another aspect, a monolithic ultrasonic fingerprint scanner includes: an acoustic matching layer to provide a contact surface for a finger to make contact; an array of piezoelectric transducers disposed beneath the acoustic matching layer, wherein each of the piezoelectric transducers is operable to generate an incident acoustic wave or an incident acoustic pulse toward the acoustic matching layer and receive reflected acoustic waves or acoustic pulses off of an object being detected; and a CMOS die electrically coupled to the array of piezoelectric transducers to receive and process the piezoelectric transducers outputs produced in response to the reflected acoustic waves or the acoustic pulses.

BRIEF DESCRIPTION OF THE DRAWINGS

FIG. 3A shows an exemplary simulation plot of phased array acoustic radiation pressure for zero degree phase shift between elements.

FIG. 3B shows an exemplary simulation plot of acoustic radiation pressure for 20 degrees phase shift between elements of a phased array.

FIG. 12A shows that an applied voltage across the air/vacuum gap of capacitor formed by two micromechanical beams beam1 and beam2 generates an electrostatic force proportional to $(V_a-V_b)^2$.

FIG. 12B shows the displacement of released beam2 for the case when there is no voltage difference between beam1 and beam2 (top plot) as opposed to the case when there is a voltage difference between the two beams (bottom plot).

FIG. 12C shows the representation of an exemplary capacitive multiplier by placing two beam1-beam2 combinations.

FIG. 12D shows the representation of an exemplary resistive multiplier by placing two beam1-beam2 combinations.

FIG. 12E shows an array of capacitive multipliers in FIG. 12C cascaded across the synapses for generating the sum of products.

FIG. 12F shows an array of pizeoresistive multipliers in FIG. 12D cascaded across the synapses for generating the sum of products.

FIG. 12M illustrates a process flow for fabricating the MEMS-based capacitive multiplier including the silicon nitride electrical isolation as viewed from a cross-section of AA' in FIG. 12L.

FIG. 42 shows experimental measurements of different silicon backing conditions.

DETAILED DESCRIPTION

Figure 1A:
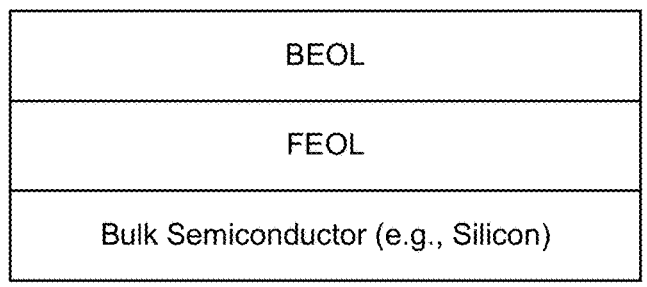
FIG. 1A shows an architectural diagram of a conventional integrated circuit chip design and an architectural diagram of an integrated circuit chip design of the disclosed technology.
Figure 1A:
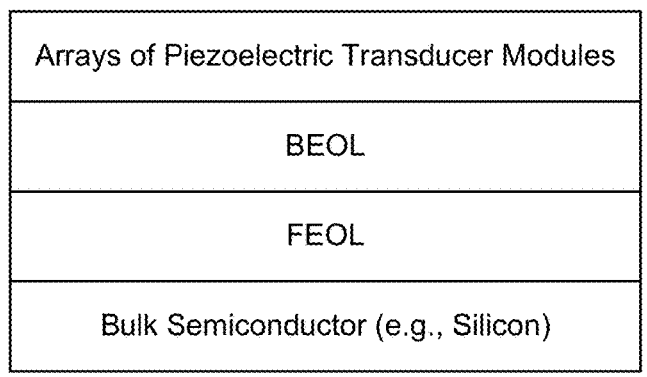

Silicon-based and other semiconductor integrated circuit (IC) chips typically use conductive wires for in-chip communication links, which create several limitations in IC chip designs including spot heating, thermal cycling degradation of components, signal interference, among others. Some chip-scale communications approaches to mitigating such problems associated with conductive wires include optical and/or wireless in-chip communications which have been explored in several physical domains, but complement and/or add to the traditional metal interconnects.

In one example, photonic interconnects have been proposed as a way to transmit digital and analog information on optical waveguides integrated into a complementary metal-oxide-semiconductor (CMOS) stack. For example, optical waveguide interconnects can provide very high bandwidth and low power consumption information transmission within chips. However, due to the internal losses of optical signals in CMOS compatible optical waveguides, and the resulting high power for optical links, much work is still needed for use of optical interconnects. Also, one of the drawbacks of the photonic links is that the links are defined by lithography in the front end of line (FEOL) or back end of line (BEOL) IC fabrication processes, which can enable adversarial interests in the IC design to physically detect function, e.g., by detecting scattered light, or tracing the optical paths.

In another example, radio-on-chip networks have been proposed for ad-hoc wireless networks on chip. For example, such radio-on-chip networks can transmit over the chip using RF radio. Due to the large signal wavelengths corresponding to common RF frequencies, such RF transmitters are point emitters operating in the near field configurations that tend to use coded signals to reduce EM interference and thus require significant power consumption.

Additionally, there has been some effort in protecting IC designs that are mapped to field programmable gate arrays (FPGAs). For example, the key to determining the functionality of an FPGA is determining its bit-stream patterns with various parts of FPGAs. Bit-streams can be encrypted in high-end FPGAs to protect the contents of the configuration memory. The encryption key (e.g., a key based on the advanced encryption standard (AES)) is stored in volatile memory, and powered by a battery in an effort to defeat unsophisticated tampering. Obfuscation is also a commonly used software technique, and can also be applied to the hardware description language used to create the design mapped to the FPGA. These techniques can be combined with the notion of a physically unclonable function (e.g., logic whose behavior is a function of chip-specific process variations) to protect a design. However, these approaches do not protect against EM-based attacks or differential power analysis. In addition, an adversary may have access to the FEOL processing or the entire IC processing during the fabrication and production at a semiconductor foundry that is operated by another party.

In the past, microelectronic devices were manufactured by companies that both designed and produced the devices. At that time, manufacturing involved fine-tuning device and manufacturing process parameters, which often warranted a need for redesign involving both the research and development (R&D of the microcircuit design and the manufacturing processes. Currently, manufacturing processes are highly advanced and standardized such that multiple microelectronic device designs can be fabricated by a single, large-scale manufacturing entity. For example, separation of manufacturing and design has created a new model for microelectronic device fabrication: the foundry model. The foundry model refers to the separation of a semiconductor fabrication plant operation (foundry) from an integrated circuit design operation, e.g., enabling a "fabless" semiconductor company to operate without any semiconductor manufacturing capability but rather contract production from a separate manufacturer entity (merchant foundry). While the foundry model is economically efficient for rapid development of integrated circuit devices, it is subject to device security concerns including theft of device designs and unauthorized alterations or modifications during production by the merchant foundry or other adversarial actors.

Moreover, as the need for computational power increases, high density integration of transistors and other circuit elements, such as 2D integration and 3D integration of multiple processor layers, are becoming increasingly necessary for many IC applications to increase the IC processing power. One of the problems in highly integrated IC chips, e.g., vertically stacked 3D ICs, is the difficulty to provide complex and a large number of interconnects between different circuit elements. In a 3D stacked chip, for example, the number of communication channels between wafers tends to be limited because of the relatively large size of through-wafer vias (TWV) to ensure bonding reliability.

The technology disclosed in this patent document uses ultrasound transducers as communication transceivers for providing wireless ultrasonic communication interconnects between different circuit elements without hardwiring between circuit elements and as built-in circuit sensors for sensing circuit conditions. Such ultrasonic communication interconnects can significantly reduce the metal interconnects between circuit elements. The disclosed technology can be used to provide programmable or reconfigurable interconnects to enable fixed circuit elements to form various functionally different circuit devices and to conceal the final circuit functions and designs from an unauthorized party and from the physical fabrication or manufacturing of the circuits. The disclosed technology can also be implemented to address the above aforementioned technical problems and limitations.

Techniques, systems, and devices are described to provide 2D and 3D integrated circuit chip designs having integrated ultrasonic or acoustic in-chip communication links and nodes.

The disclosed technology integrates ultrasound actuator arrays into 2D or 3D IC chips to form sonar arrays that transmit a directional sonic pulse from one functional unit or module in the chip to another, providing tunable sonic intra-chip communication links between any two points by adjusting the delays/phases and/or amplitudes of the sonic communication signals on transmit. In some implementations, for example, the ultrasound actuators can be based on piezoelectric materials or elements. In addition, the ultrasound actuators can be configured using electrostatic transducers, e.g., including capacitive/electrostatic materials or elements (e.g., including capacitive micro-machined ultrasonic transducers (CMUT)), which can be implemented, for example, in addition to or instead of the piezoelectric-based actuators (e.g., the piezoelectric AlN transducer elements). Examples of CMUT transducer elements are described in Wygant, I., "A comparison of CMUTs and piezoelectric transducer elements for 2D medical imaging based on conventional simulation models", Ultrasonics Symposium (IUS), 2011 IEEE International, Vol. 100, No. 18-21, October 2011, which is incorporated by reference as part of this patent document. More generally, the disclosed technology can implement the ultrasound in-chip wireless communication links using any of piezoelectric, electrostatic, magnetic, thermal, electrostrictive actuation/sensing elements acoustic communication signaling. In some implementations, such sonar modules can be used to transmit signals from one chip to another chip through a common substrate, while making use of the frequency-selective nature of acoustic transducers and waveguides to communicate to multiple receivers over different frequency bands at the same time, e.g., via frequency division multiplexing. Frequency division multiplexing can be implemented to carry different channels at different acoustic frequencies. For example, the integrated sonars can also be used to interrogate defects in chip interconnects over time to measure chip reliability.

FIG. 1A shows an architectural diagram of a conventional integrated circuit chip design 10 based on the complementary metal-oxide-semiconductor (CMOS) technology and an architectural diagram of an example of an integrated circuit chip design 20 for implementing the disclosed technology. The conventional CMOS IC chip design 10 includes a bulk semiconductor portion, e.g., bulk silicon die or substrate, upon which an front-end-of-line (FEOL) portion is structured to include individual and discrete circuit elements, e.g., transistors, capacitors, resistors, etc., patterned in layers within the FEOL portion formed over the semiconductor substrate. In some configurations, the FEOL portion of the conventional IC chip design 10 can include CMOS circuit elements for one or more digital logic circuits. The conventional IC chip design 10 includes a back-end-of-line (BEOL) portion to provide the hardwiring connects within each circuit element and hardwiring interconnects between the discrete circuit elements in the FEOL portion, such as metal contacts or lines. For example, the BEOL includes conductive contacts such as metal lines, metal contacts or metal vias, insulating layers or materials (e.g., dielectrics), and bonding sites for chip-to-package connections. The interconnects in the BEOL in the IC chip design 10 link the discrete circuit elements in FEOL to form functional circuit blocks.

The architectural diagram of the IC chip design 20 of the disclosed technology shown in FIG. 1A is based on a different interconnect configuration using ultrasound communication links. The IC chip design 20 includes a bulk semiconductor portion, a front-end-of-line (FEOL) portion that includes discrete circuit elements, a back-end-of-line (BEOL) portion and ultrasound transducer modules (e.g., piezoelectric transducer modules). Different from the IC chip design 10 where the interconnects in the BEOL link the discrete circuit elements in the FEOL portion to form functional circuit blocks, the IC chip design 20 uses the ultrasound transducer modules as communication nodes to provide a significant portion of or all of inter-element communication interconnects between different circuit elements in the FEOL portion by using wireless ultrasound signaling as interconnects. The BEOL portion of the IC chip design 20 provides conductive connections between the ultrasound transducer modules and circuit elements in the FEOL portion and may also include, in some implementations, certain interconnects for the circuit elements in the FEOL portion. When the ultrasound transducer modules are not activated or functional, the circuit elements in the FEOL portion are largely discrete or isolated circuit elements or circuit element blocks or clusters of two or more interconnected circuit elements. When the ultrasound transducer modules are activated to provide desired interconnects between the circuit elements in the FEOL portion, the circuit elements in the FEOL portion form a functional IC device under the IC chip design 20 and become functional. Therefore, the ultrasound transducer modules provide ultrasonic or acoustic communication signaling capabilities of the discrete circuit elements (e.g., CMOS digital logic circuits) to communicate wirelessly between such elements, thereby reducing some or all of the hardwired interconnections in a conventional IC chip design. In some examples, the IC chip design 20 includes control circuits including driver, read, and logic circuits as part of the FEOL portion that electrically communicate with the piezoelectric transducer modules via electrical connections of the BEOL portion. The BEOL portion can also include metal reflectors or other components that aid in the acoustic signal propagation. In FIG. 1A, the IC chip design 20 is shown to have a particular structure where the FEOL portion, the BEOL portion, and the layers for the ultrasound transducer modules are formed in the shown sequential order over the substrate. This configuration of the IC chip design 20 is an example only and other configurations or structural sequences may be implemented depending the specific needs of IC designs and circuit applications.

An ultrasound signal tends to have a footprint and spatial extent determined by the acoustic frequency of the signal and the physical conditions of the signal path that may cause diffraction, scattering and spreading of the ultrasound signal. The smallest beam spot size is dictated by the diffraction limit on the order of one half of the ultrasound signal wavelength. Accordingly, a metal interconnect may be configured to have a smaller footprint than that of an ultrasound signal interconnect. In implementing the wireless ultrasound signaling as interconnects for different circuit elements in the IC chip design 20 in FIG. 1A, it may be advantageous in some applications to use ultrasound signaling for all interconnects of the different circuit elements and, in other applications, it may be more beneficial to use ultrasound signaling for part of the interconnects and use metal lines or contacts for the remaining interconnects. Such metal lines or contacts for interconnects between different circuit elements are can be in the BEOL portion.

Figure 1B:
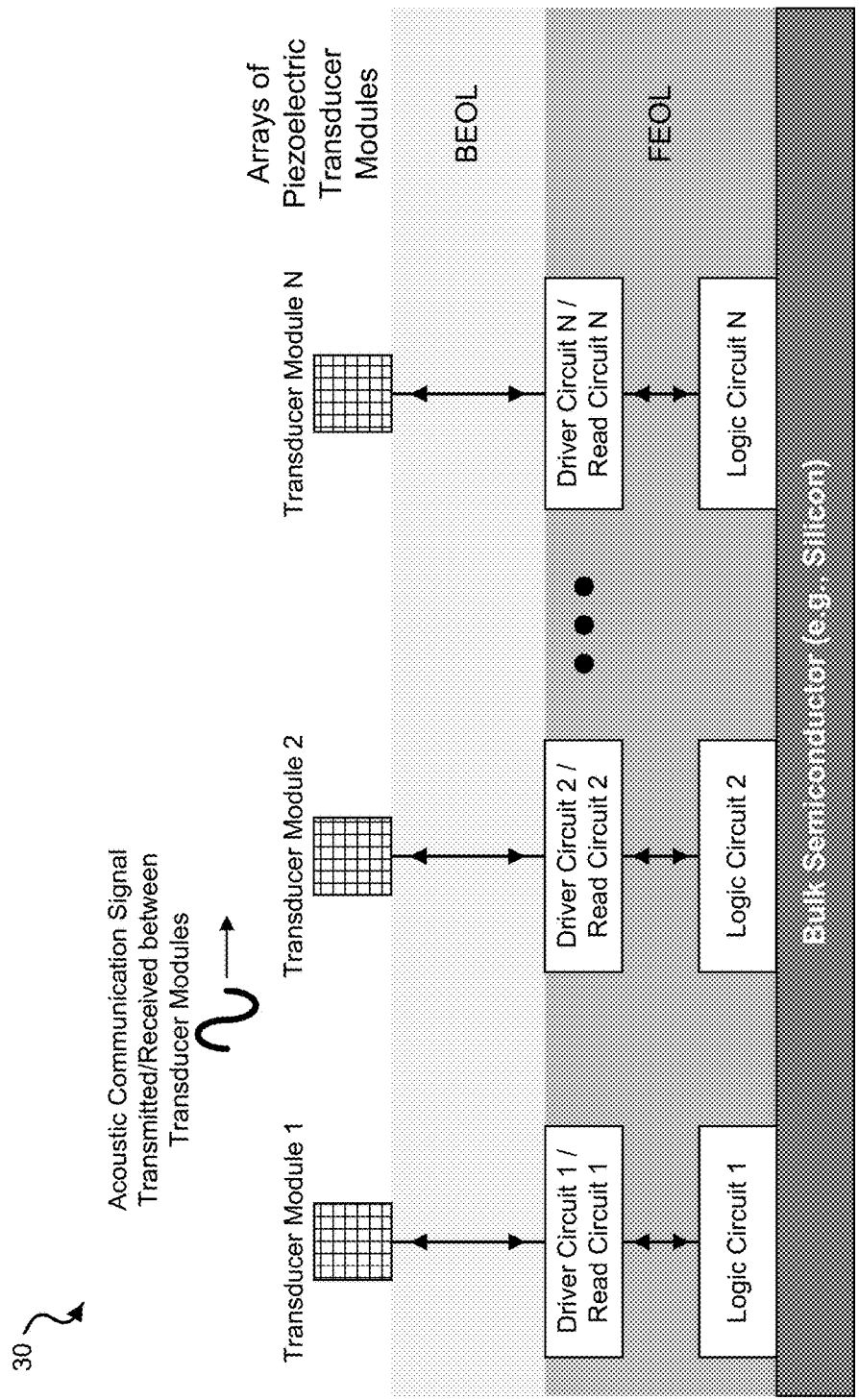
FIG. 1B shows a diagram of the disclosed acoustic in-chip communication signaling IC chip design.

FIG. 1B shows a functional diagram 30 of the IC chip design 20 of the disclosed technology illustrating wireless intra-communication in a semiconductor medium between circuit modules of the IC chip. The diagram 30 shows an exemplary embodiment of the IC chip design 20 in which an array of 1, 2, . . . N piezoelectric transducer modules are operable to transmit and receive directional acoustic signals carrying information to communicate between the transducer modules. For example, the wavelength of the sonic signals depends on the frequency and propagation speed of the signal, and the propagation speed depends on the medium through which the signal propagates. The speed of sonic transmission in a semiconductor medium (e.g., $\sim 9 \times 10^3$ m/s in a dielectric medium such as silicon) is five orders of magnitude lower that the speed of electromagnetic transmission (e.g., $2.997 \times 10^8$ m/s). Thus, sonic signals can be transmitted at wavelengths in the microns for desired frequencies in the GHz range, e.g., protecting the acoustic communication signal from RF and other noise within the IC circuit. The array of piezoelectric transducer modules are communicatively coupled to individual control circuit elements or blocks (e.g., of two or more circuit elements), e.g., which can be formed in the FEOL portion over the semiconductor substrate. The individual control circuits can include a driver circuit to generate an electric signal to the corresponding transducer module that determines the magnitude, frequency, and/or phase of the acoustic communication signal. The individual control circuits can include a read circuit to receive a transduced electric signal from the corresponding transducer module that receives the transmitted acoustic communication signal. For example, the driver circuits and/or read circuits can include analog and digital circuit components (e.g., inverter delay elements, analog-to-digital converters (ADC) and digital-to-analog converters (DAC), amplifiers, etc.). The individual control circuits can include a logic circuit, e.g., of digital and/or analogic logic circuit components, to provide and receive electric signals as digital waveform carrying the information to and from the driver and read circuits, respectively, which can be processed by other circuits of the IC chip. For example, the digital waveform can be a phase-coded and/or frequency-coded waveform or waveforms included in a composite waveform. In some examples, the logic circuits can be configured of one or more CMOS layers.

Figure 1C:
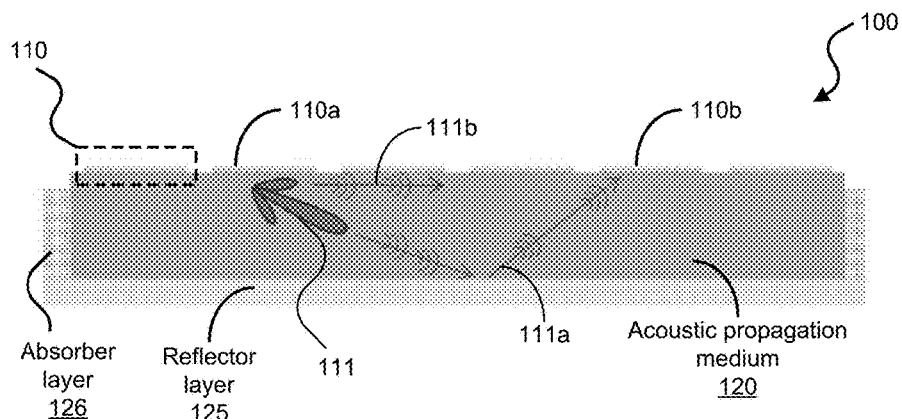
FIG. 1C shows a schematic illustration of an exemplary chip-scale wireless communications IC device.

Each of the ultrasound transducer modules of FIGS. 1A and 1C is configured to generate a steerable acoustic ultrasound signal to target one or more desired ultrasound transducer modules to provide desired ultrasound interconnects for the circuit elements associated with the transmitting and receiving ultrasound transducer modules. As illustrated in FIG. 1C and described in greater detail below, each ultrasound transducer module includes multiple ultrasound transducer elements, e.g., in a 2-D array, and operates to control the relative amplitude and phase values of ultrasound signals generated by multiple ultrasound transducer elements so that the ultrasound signals are added up to form a final composite ultrasound signal that is directed to a particular location or region in the circuit where one or more targeted receiving ultrasound transducer modules are located. Each ultrasound transducer module can be operated as a transmitter and a receiver and thus is a ultrasound transducer transceiver element. The driver/read and logic circuits for the ultrasound transducer modules are shown to be part of the FEOL portion in FIG. 1B, but may also be in the BEOL portion or other layers. The use of multiple ultrasound transducer elements for an ultrasound transducer module as a transceiver device for transmitting steerable output ultrasound signals and for receiving/detecting ultrasound signals can be implemented in various configurations, including some examples described in "Two-Port Electromechanical Model for Bulk-Piezoelectric Excitation of Surface Micromachines Beam Resonators" by Ardanuc and Lal in Journal of Microelectromechanical Systems, pp. 626-640 in Vol. 18, No. 3, June 2009, and "Beam Steering with Pulsed Two-Dimensional Transducer Arrays" by Turnbull and Foster in IEEE Transactions on Ultrasonics, Ferroelectrics, and Frequency Control, pp. 320-333, Vol. 28, No. 4, July 1991, which are part of the U.S. provisional application No. 61/672,214 and are incorporated by reference as part of this patent document.

The disclosed acoustic in-chip communication technology can be implemented to provide many advantages. For example, the disclosed acoustic in-chip communication can use linear and two-dimensional arrays of piezoelectric transducers to generate directional ultrasonic pulses in three dimensions for CMOS information processing and trusted integrated circuit (TIC) operation. For example, exemplary phased array sonic transducers can be operated at GHz frequencies alongside and/or integrated with other analog or digital chip logic on a single IC chip. For example, the disclosed technology can be implemented in a variety of applications including medical (ultrasound) imaging, non-destructive evaluation (NDE) of IC chip components, and sonar communications. Historically, for example, these arrays have operated in the frequency range of 1-30 MHz for medical imaging, 100 kHz to 10 MHz for NDE, and 1-100 kHz for sonar communications. By operating at high frequencies of 1-10 GHz, the wavelength in silicon can be in an exemplary range of 9 to 0.9 µm. Since the elements of a sonar array are spaced by fractions of the sonic wavelength (e.g., k/2), chip devices employing the disclosed technology can be configured with hundreds to thousands of sonar arrays, e.g., for a millimeter to centimeter sized IC chip.

For example, the disclosed acoustic in-chip communication technology can provide a sonic 2D or 3D programmable interconnect framework for massively parallel computation in IC chip devices. The sonic 2D or 3D IC interconnects can enable communications in one chip, or through IC stacks, forming a user defined communications layer for 3D ICs. In some implementations, encrypted pulse sequences can be used to form secure communication channels that are ad-hoc in nature, e.g., providing programmable wireless interconnections between discrete IC elements (e.g., of the FEOL portion). The added interconnect capability can allow the programmers to use ultra-high fan-out and fan-in capabilities, e.g., which is often needed to implement algorithms in associative pattern recognition algorithms, such as in applications including face or feature recognition in image processing. Furthermore, the added acoustic programmable wireless link can relieve the communications bottleneck encountered in multi-core digital systems.

For example, the disclosed acoustic in-chip communication technology can provide sonar based chip-interrogation. For example, the disclosed integrated piezoelectric transducer arrays can be used to interrogate the chip or a multi-chip package to realize an integrated non-destructive evaluation (NDE) capability. Such interrogations can be employed for chip-scale NDE of wire-bonds, chip-to-chip interconnects, vias, etc. Also, for example, for security, an adversary initiated chip manipulation could be detected at a very early stage (e.g., such as by a merchant foundry for manufacturing of an IC chip design). Moreover, early detection of chip tampering could lead to immediate removal of memory or self-destruction for trusted use of integrated circuits.

Furthermore, most existing IC devices generate substantial amounts of heat that can (1) lead to degradation of portions or the entire IC device and (2) lower performance (e.g., speed) of the device during operation, e.g., particularly during extensive periods of use. IC devices can undergo various spot heating, in which particular locations or regions (e.g., circuit blocks) of the IC generate high heat. For example, the disclosed integrated piezoelectric transducer arrays can be used to monitor spot heating within the IC device to which the disclosed transducer arrays are employed. Knowledge of spot heating during operation of IC devices is of great interest, as such monitoring could be used to reroute process implementations to other IC device resources in areas outside of the spot heating, thereby allowing for the spot heat to dissipate faster and avoid reduced device performance or degradation.

Moreover, for example, the disclosed integrated piezoelectric transducer arrays can be used to image and thereby monitor structural defects and fractures of in-chip elements and chip-to-chip interconnection structures that can lead to device failure. For example, thermal cycling of ICs in various microchip-based devices like computers, mobile communication (smart phone devices), etc. can also cause degradation at the grease interface between IC chips and their coupled heat syncs. Additionally, delamination of solder balls at wire bonding interfaces is a common problems that result in premature failure of such chip-based devices. Thus, using the disclosed technology, sonar based chip-interrogation can be implemented to prolong the lifetime of such chip-based devices.

For example, the disclosed acoustic in-chip communication technology can provide sonar based lock-key operations. For example, for safe operation of some proprietary chip-sets, a lock/key system is employed to ensure activation by a known entity, and deem the chip inoperable by an adversary. Current methods include microelectromechanical systems (MEMS) gears and beams for enabling a lock, which although effective can be not as reliable due to stiction. For example, the disclosed integrated piezoelectric transducer arrays can be used to provide sonar links to read surfaces preprogrammed to reflect ultrasonic pulses through a set of programmable reflectors, triggering a device if the pulse makes it to a target receiver on chip.

In one aspect, an integrated circuit chip device with wireless on-chip communications capabilities includes a semiconductor substrate capable of propagating acoustic energy signals and an array of acoustic signaling modules formed on the substrate and structured to include a sub-array of acoustic transducer elements capable of transmitting and receiving the acoustic energy signals, in which each acoustic transducer element is operable to generate an acoustic communications signal to propagate through the substrate based on an electronic control signal and to receive the acoustic communications signal an acoustic signaling module to communicate with one or more other acoustic signaling modules. For example, the device can further include a control circuit layer formed on the semiconductor substrate and under the array of acoustic signaling modules to receive an external electronic signal and produce the electronic control signal to one or more acoustic transducer elements. For example, the acoustic communications signal can be modulated by the device using one or more of amplitude modulation, frequency modulation, or phase modulation.

In another aspect, a semiconductor integrated circuit device having wireless ultrasonic communication links includes a semiconductor substrate, layers formed over the semiconductor substrate and patterned to form circuit elements including transistors, and an array of ultrasound transducers formed in the layers over the semiconductor substrate, each ultrasound transducer including ultrasound transducer elements which are operable to generate an ultrasound signal carrying information to communicate with one or more ultrasound transducers in the array and are operable to receive an incident ultrasound signal from one or more ultrasound transducers, the ultrasound transducers being communicatively coupled to respective individual circuit elements or blocks of two or more circuit elements of the circuit elements formed in the layers over the semiconductor substrate to act as communication nodes for the respective individual circuit elements or blocks of two or more circuit elements with other individual circuit elements or blocks of two or more circuit elements. Each ultrasound transducer in the array of ultrasound transducers is configured to control transmission or reception of the ultrasound transducers so that the ultrasound transducers in the array of ultrasound transducers are interconnected via ultrasound signals to form an ultrasound communication network of ultrasonic communication links, without hardwiring via metal contacts, between the circuit elements formed in the layers over the semiconductor substrate.

FIG. 1C shows a schematic illustration of an exemplary chip-scale wireless communications IC device 100 including an array of acoustic transceiver (sonar) modules 110 capable of transmitting and receiving acoustic communications signals. The device 100 is structured to include a substrate 120 to provide a base for the array of sonar modules 110 and formed of a solid state semiconductor material capable of propagating acoustic energy (e.g., ultrasound signal) within the device 100, e.g., including between sonar modules 110 of the array. In some examples, the sonar modules 110 can be configured as thin films of aluminum nitride (AlN) and/or lead zirconium titanate (PZT) on top of a metallization layer. In some examples, the acoustic propagation medium 120 can include silicon, e.g., such as the silicon material of a silicon die. Each or any of the sonar modules 110 can be structured to include a sub-array of individual piezoelectric transducer elements 130 (shown in FIG. 1D), e.g., sometimes referred to herein as pixel elements or pixels. The sub-array of individual piezoelectric transducer elements 130 can be communicatively linked to underlying electronic control circuits (shown in FIG. 1D as control circuit layer 132). The electronic control circuits can include driving circuits for providing the driving signals that the transducer elements 130 transduce to produce the acoustic communication signals and logic circuits to process received acoustic communication signals transduced by the transducer elements 130.

In some implementations, for example, the device 100 can further include an acoustic reflector/mismatching layer 125 capable of reflecting or refracting the exemplary intra-device ultrasound signal, e.g., which can be used to steer the ultrasound communication signal from one or more sonar modules 110 to another one or more sonar modules 110. For example, the acoustic reflector layer 125 can be configured under the acoustic propagation medium substrate 120, as shown in FIG. 1C, and/or be configured along one or more sides of the substrate 120. In some implementations, for example, the device 100 can further include an acoustic absorber layer 126 to absorb the exemplary intra-device ultrasound signal, e.g., preventing the ultrasound communication signal from transmission beyond the device 100. In the example shown in FIG. 1C, the acoustic absorber layer 126 is configured along the sides of the acoustic propagation medium substrate 120. In some implementations, for example, the device 100 can be included in an array of devices 100 for both intra- and inter-device in-chip wireless communication signaling. In some implementations, for example, the device 100 can be included on a conventional integrated circuit chip, as described later in this patent document.

Figure 1D:
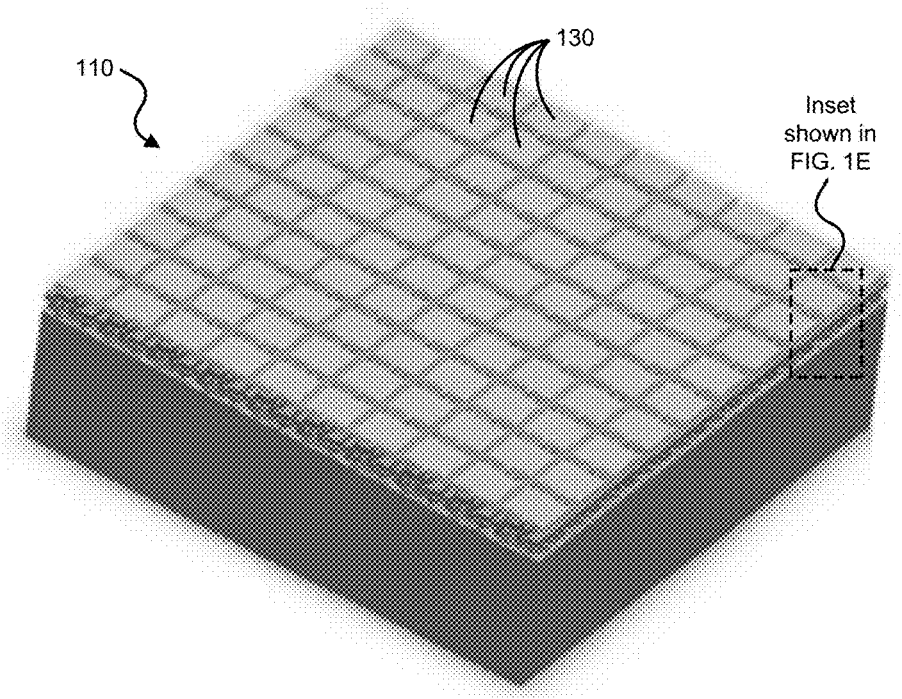
FIG. 1D shows an inset schematic from FIG. 1C showing an exemplary CMOS-integrated piezoelectric transducer array of an exemplary sonar module.

As shown in FIG. 1D, the piezoelectric transducer elements 130 of the sonar modules 110 can be configured with uniform or periodic spacing in the pixel array, e.g., including $\lambda/2$ spacing. For example, since each piezoelectric transducer element 130 of the sub-array (of a sonar module 110) is a fraction of a wavelength in lateral dimensions, relatively small phased arrays for sonar transmit and receive blocks can be implemented. In some embodiments of the device 100, for example, each sonar module 110 can include 10-20 pixels which are placed approximately one-half of an acoustic wave wavelength apart. In one example, each pixel can be configured to a size in a range of 3-10 µm, such that each sonar module 110 includes a planar size of ~100×100 µm, e.g., which is about the size of a contact pad on a CMOS chip. Also for example, the acoustic propagation medium substrate 120 can be configured to a height of 750 µm (or 84$\lambda$ in this example).

Figure 1E:
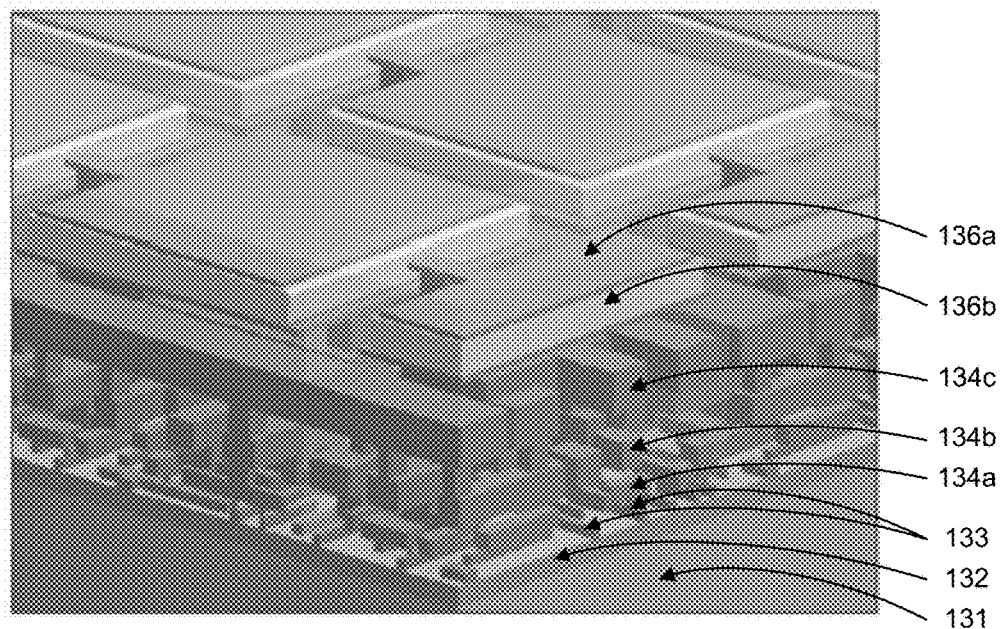
FIG. 1E shows an inset schematic from FIG. 1D showing an exemplary CMOS-integrated piezoelectric transducer element.
Figure 1F:
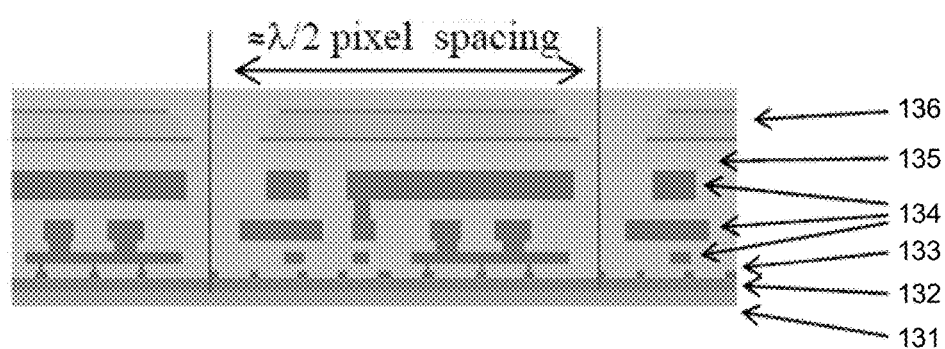
FIG. 1F shows an inset schematic from FIG. 1D showing a cross-sectional view of the exemplary CMOS-integrated piezoelectric transducer element.

FIGS. 1E and 1F show inset schematics from FIG. 1D showing the piezoelectric transducer element 130 of the device 100 in a three-dimensional view and a cross-sectional view, respectively, over a control circuit layer 132 and the substrate 120. For example, the acoustic propagation medium material of the substrate 120 can include bulk Silicon material 131. In some examples, the control circuit layer 132 can be structured to include one or more CMOS active layers 132 structured to include individual control circuit blocks corresponding to the individual piezoelectric transducer elements 130 of the sub-array, e.g. in which the control circuits can include one or more driving circuits, read circuits, and logic circuits including digital logic, analog logic and/or amplifiers, which are formed on the exemplary bulk Silicon layer 131. A first metal layer 133 can be formed over the one or more CMOS active layers 132. For example, the bulk Silicon substrate 131, the CMOS active layers 132, and the first metal layer 133 form a FEOL region of the device 100. The transducer element 130 can be structured to include more metal layers, e.g., including a second, a third, and a fourth metal layers 134a, 134b, and 134c, respectively, as shown in FIGS. 1E and 1F. The transducer element 130 can be structured to include an electrode structure layer 136b, upon which, a piezoelectric material (e.g., AlN) layer 136a is formed. The transducer element 130 can be structured to include an inter-metal dielectric material 135 that is formed between the metal layers 134a, 134b, and 134c, and over the FEOL region. For example, the metal layers 134a, 134b, and 134c, the electrode structure layer 136b, the inter-metal dielectric material 135, and the piezoelectric material layer 136a form a BEOL region of the device 100.

For example, the metal layer structures 133, 134a, 134b, and/or 134c function both as interconnect layer(s) for electronics, and can also function as part of the disclosed technology as custom designed acoustic wave guiding, channeling, or scattering structures. In some examples, is also possible to clear the underlying regions of certain pixels of metals and route them around the pixels to allow propagation of ultrasonic signals without any obstruction.

The sonar modules 110 are operable to receive and convert an electrical control signal to generate an acoustic energy wave or pulse carrying a communication signal to communicate with one or more other sonar modules of the array, which can receive the acoustic communication signal and transduce it to an electrical signal. For example, the array of sonar modules 110 can operate as acoustic transmitter and receiver (transceiver) modules, which can communicate with each other by proper phasing of sonar pulses sent at desired angles, frequency division modulation, or other techniques. As shown in FIG. 1C, a sonar transceiver module 110A transduces an electrical control signal that it receives to an ultrasound signal 111 that propagates through the acoustic propagation medium 120. For example, the ultrasound signal 111 can reflect off a device boundary (e.g., such as acoustical reflector layer 125) and be incident on another sonar transceiver module 110b, as shown by the signal propagation path 111a. Additionally or alternatively, for example, surface acoustic waves (SAW) can be used to communicate laterally, as shown by the SAW propagation path 111b.

In some implementations, the generated ultrasound signal 111 can be a continuous or pulsed ultrasound (sonic) wave. For example, the sonic waves can be generated at frequencies from the hundreds of MHz to GHz in a silicon-based propagation medium, with the corresponding wavelengths in a range from the tens to single microns, e.g., including 90 to 9 μm wavelength sonic waves at 100 MHz to 1 GHz frequencies, respectively, in a silicon medium. The relatively small acoustic wavelength, e.g., as compared to the thickness of the silicon medium or substrate, enables the use of the propagation medium 120 to transmit the ultrasound signals from one place to another.

For example, the ultrasound beam 111 can be launched into the propagation medium 120 at a wide range of solid angles and targeted to a specific receiver sonar module 110b, e.g. any of the sonar modules in the array, by adjusting the delays/phases and amplitudes of the ultrasound pulses to each of the piezoelectric transducer elements 130.

In some implementations of the disclosed acoustic in-chip communication technology, for example, further accuracy in targeting can be achieved by recombining the electronic signals from the receiving transducer array with appropriate delays for the desired channel. This sonic programmable communications channel can be used as a reconfigurable interconnect network that a non-desired party (adversarial interests) cannot determine with any physical scheme. The sonic interconnects can be software defined, and hence protectable using many methods of software encoding.

The exemplary acoustic in-chip communication devices can be configured to prevent the acoustic signals from propagating out of the device, or leaking. For example, because sound waves decay very fast and they cannot propagate out of the device, it can be very hard for a non-desired user (or adversary) to listen to the acoustic channels. For example, since optimal communication uses both the configuration of the transmitter and receiver arrays, the actual acoustic signals can be obfuscated with deliberate transmitter spurious signals that match nulls in the receivers but are otherwise indistinguishable from the real signals.

For example, a different modality of ultrasonic chip-scale/board-level communication is possible under acoustically mismatched or highly reflective boundary conditions instead of absorbing boundary conditions. In this exemplary mode, individual ultrasonic transducers on the transmitting array can be used to control standing wave patterns at the transducers of the receiving array. As such, the disclosed acoustic in-chip communication devices can be regarded as a large acoustic resonator, to which different transducers located at different locations couple to with varying coupling coefficients that are a function of frequency of excitation. A matrix approach based on linear superposition is useful to model the linear regime of this modality.

Linear phased arrays can be used to focus a beam and aim it in the desired direction with characteristic radiation profiles. In ultrasound imaging, the beam can be scanned over the target field, and the returned signal is used to form the image based on acoustic reflection/transmission characteristics or time-of-flight information. In the disclosed technology, scanning a beam and focusing it in a single direction allows for the choice of where to communicate data. The principles of beam steering and focusing, e.g., using a linear phased array, is described, which is important for the understanding of the disclosed techniques of SONAR (SOund NAvigation & Ranging) operation. Examples of beam steering and focusing of the disclosed transducer arrays based devices for ultrasound imaging applications, for example, are described in: "An Integrated Circuit with Transmit Beamforming and Parallel Receive Channels for Real-Time Three-Dimensional Ultrasound Imaging" by Wygant et al., 2006 IEEE Ultrasonics Symposium (IUS), pp. 2186-89; "Circuit Design and Simulation of a Transmit Beamforming ASIC for High-Frequency Ultrasonic Imaging Systems" by Athanasopoulos et al., 2011 IEEE Transactions on Ultrasonics, Ferroelectrics, and Frequency Control, Vol. 58, No. 7, pp. 1320-31; and "Medical Imaging: Principles, Detectors, and Electronics—Chapter 7: Electronics for Diagnostic Ultrasound" by Wodnicki et al., Krzysztof Iniewski (ed), John Wiley & Sons 2009, in which the aforementioned documents are incorporated by reference as part of this patent document.

Figure 2A:
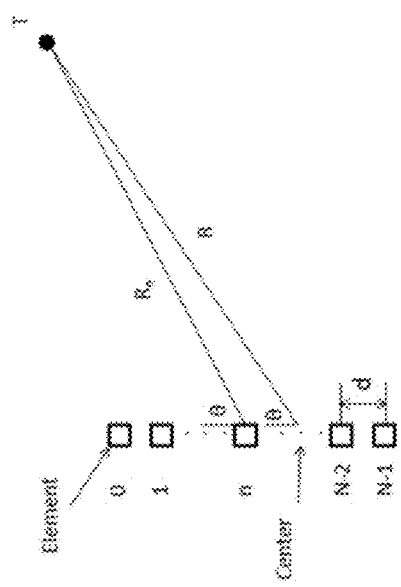
FIG. 2A shows a diagram of an exemplary one dimensional array of transducer elements spaced apart and used to focus on a single point.

FIG. 2A shows a diagram of an exemplary one dimensional array of N elements spaced d apart, used to focus on a single point T. The distance from the center of the array to the target is denoted as R, and the distance from element n to the target is denoted as R. Each element is represented as an isotropic emitter. As such the wave radiating from each would be represented as in Equation (1):

$$w = Ae^{j(kr-\omega t+\beta)} \qquad (1)$$

In Equation (1), A is the amplitude of the signal, k is the wavenumber, r is the spherical radius from the source, w is the frequency, t is time, and β is the time phase delay of the source. If the target point T is far enough away such that R is much greater than the inter-element spacing d, than the angle θ (with respect to the positive z direction) for all the elements can be approximated as the same. This means that effectively all of the paths to the target from the elements are parallel, and the difference in path length, $\Delta r_n = R_n - R$, can be found from a simple trigonometric identity:

$$\Delta r_n = R_n - R = \frac{2n - N + 1}{2} \cdot d \cdot \cos(\theta) \qquad (2)$$

This leads to the pattern radiating from the $n^{th}$ element in the array to have the following form in Equation (3):

$$w_n = = Ae^{j(k(R+\Delta r_n)-\omega t+\beta_n)} \qquad (3)$$

If the actuation pattern of the array is chosen so that all elements are operated with the same amplitude and frequency but different phases, then the corresponding acoustic phasor at the target point T, ωt, is the sum of all the wave contributions $w_n$ of the individual elements as given by Equation (4):

$$w_t = Ae^{jkR}e^{-j\omega t}\sum_{n=0}^{N-1} e^{j(k\Delta r_n+\beta_n)} \qquad (4)$$

From this equation, it can be seen that a maximum will occur when the following equality is met:

$$k \cdot \frac{2n - N + 1}{2} \cdot d \cdot \cos(\theta) + \beta_n = 0 \qquad (5)$$

By selecting a value for θ, the phase delay needed at each element can be calculated. From Equation (5), it can be seen that the phase is linear between elements. However, for example, due to the cyclic nature of both Equations (4) and (5), in addition to the designed main lobe of the beam, undesirable side-lobes may appear as well. Careful design of element spacing and number of elements is implemented to treat such results. In addition to this, there can be a trade-off in terms of space and power, which is taken into account.

Figure 2B:
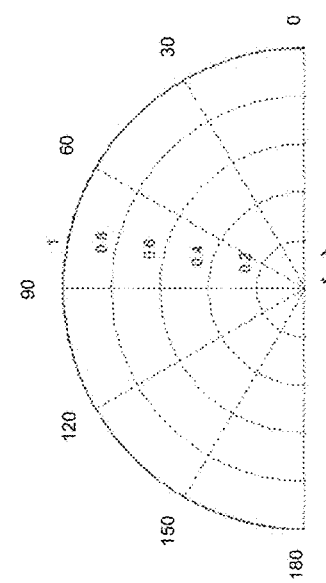
FIG. 2B shows data plots of exemplary acoustic responses from an acoustic radiator source.
Figure 2B:
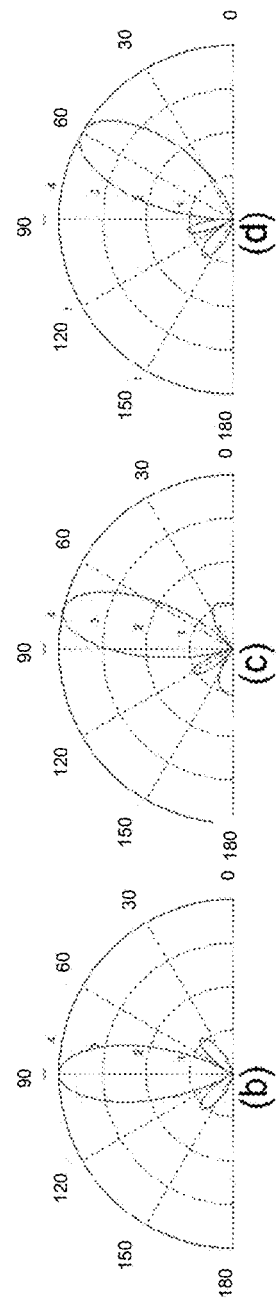

For example, using a single isotropic acoustic radiator as in FIG. 2B(a) shows a uniform response at all angles from the source. For example, using four isotropic acoustic radiators separated by $d=\lambda/2$ and actuated with the same phase, a pattern as shown in FIG. 2B(b) can be produced. In this case, the amplitude is 4 times as large at the 90 degree and reduced for other angles. The plots shown in FIGS. 2B(c) and 2B(d) represent patterns obtained from phase delays of 20 degree and 45 degree, respectively.

Exemplary simulations of the disclosed acoustic in-chip communication devices were performed. For example, the exemplary simulations utilized Finite Element Modeling (FEM) software, which can provide a tool to aid in the phased-array design, especially in the presence of complex boundary conditions. Also, for example, PZFlex was used to calculate time domain responses of materials to phased acoustic excitations of piezoelectric elements on a silicon substrate. In the exemplary simulations, each element is pulsed with wavelet pulses of either in-phase or a linearly changing phase difference between elements. The exemplary resulting acoustic pressure field is plotted in FIGS. 3A and 3B for in-phase and linearly changing phase difference (e.g., steps of 20° between neighboring elements) excitations, respectively.

FIG. 3A shows an exemplary simulation plot of phased array acoustic radiation pressure for zero degree phase shift between elements. The inset diagram in FIG. 3A shows a zoomed view of an exemplary AlN transducer array. In this example, the input excitation was 1 V at 100 MHz, yielding an ultrasonic wave with a maximum pressure of 20 kPa. FIG. 3B shows an exemplary simulation plot of acoustic radiation pressure for 20 degrees phase shift between elements of the phased array. In this example, the maximum amplitude of the pressure wave is 20 kPa.

PZFlex was also used to calculate the time domain response of a single element pulsed as well as the received signals on the neighboring pixels. For example, a voltage signal on the first pixel creates an acoustic wave, which travels through the silicon substrate and reflects off of the back surface and returns to the top surface. As it travels beam spreads out and the neighboring pixel will generate a voltage in response to the acoustic pulse.

Figure 3C:
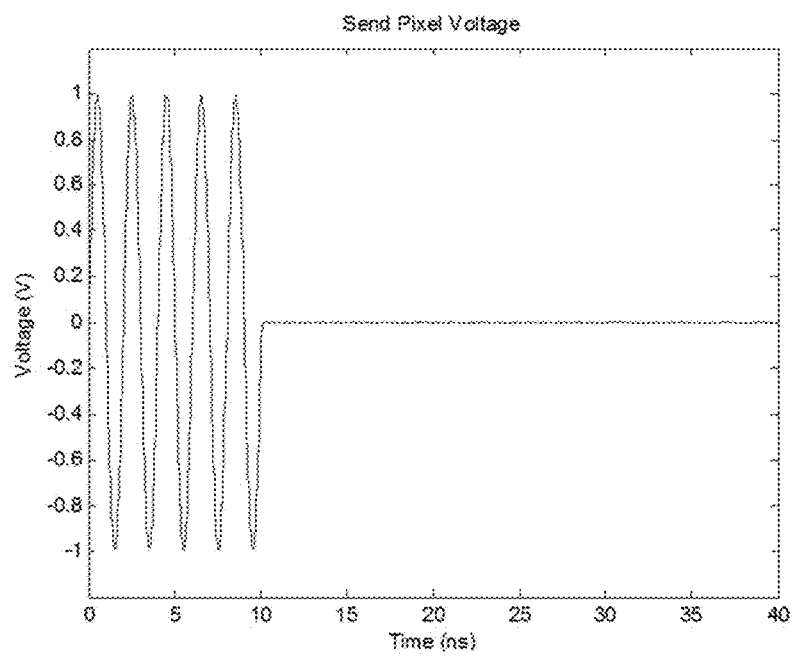
FIG. 3C shows a plot of the applied signal voltage for an exemplary simulation of the time domain response of an exemplary transducer element generating an acoustic pulse.
Figure 3D:
FIG. 3D shows an exemplary simulation plot of the acoustic radiation pressure for the initial pulse.
Figure 3E:
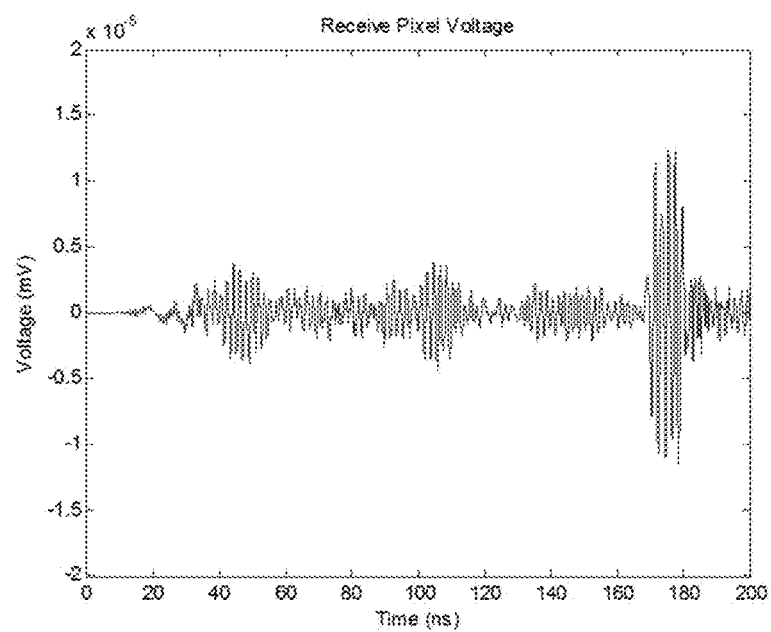
FIG. 3E shows a data plot of the signal received by an exemplary transducer element in the array.
Figure 3F:
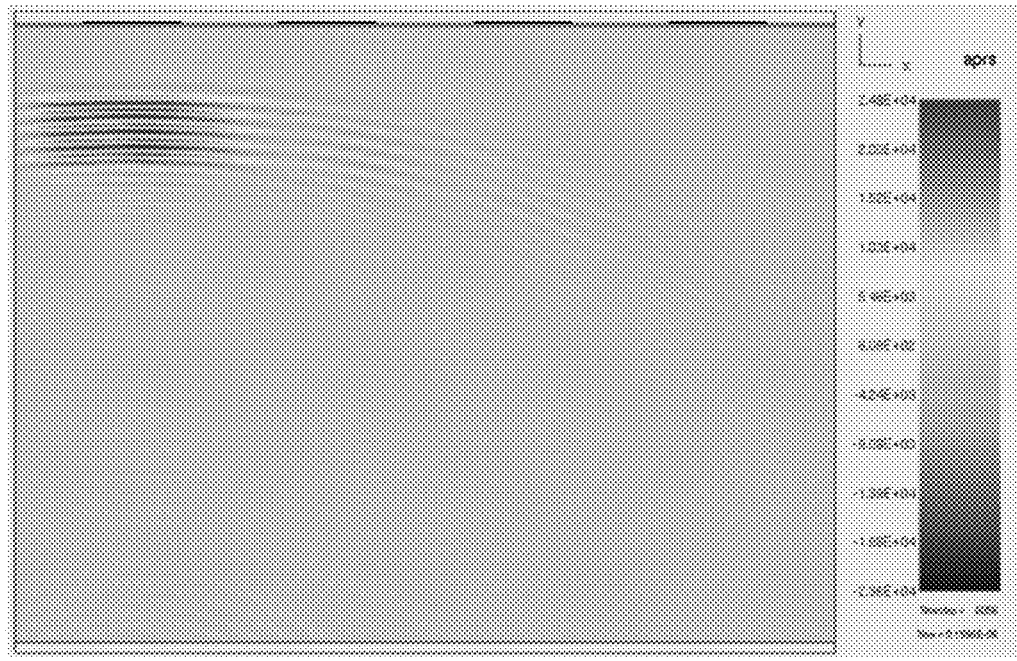
FIG. 3F shows an exemplary simulation plot of acoustic radiation pressure for the traveling and reflected pulse.

FIG. 3C shows a plot of the applied signal voltage, e.g., 1 Vp-p 5 cycles of 500 MHz Sine wave, for the exemplary simulation of the time domain response of an exemplary single transducer element generating an acoustic pulse wave. FIG. 3D shows an exemplary simulation plot of the acoustic radiation pressure for the initial pulse leaves from the left-most pixel of the exemplary array. FIG. 3E shows a plot of the receive signal at the adjacent pixel, e.g., including a delay is 160 ns, which corresponds to the speed of acoustic waves in silicon. FIG. 3F shows an exemplary simulation plot of acoustic radiation pressure for the pulse after travelling to a reflecting surface (e.g., at the bottom) and reflecting back. As shown in FIG. 3F, the beam width has widened and some of the energy is picked up by the immediately adjacent pixel.

Exemplary implementations of the disclosed acoustic in-chip communication technology were performed. In one implementation, for example, exemplary acoustic in-chip communication devices were fabricated using an RF MEMS process. Starting with a silicon substrate, the RF MEMS process involved deposition of silicon dioxide of 3.5 μm. Trenches were etched into the silicon dioxide and filled with tungsten, which was then planarized using chemical mechanical polishing. The tungsten can act as an etch stop for the aluminum nitride in subsequent steps. Next, a bottom electrode was deposited and patterned for the back side electrical contact. This was followed by the deposition of the piezoelectric aluminum nitride layer. After a photolithography step, the piezoelectric aluminum nitride layer was etched until reaching the tungsten layer. Finally, a top layer metal was deposited and patterned for the exemplary devices. In one exemplary embodiment of the devices for a SONAR system, a four by four piezoelectric transducer element array was laid out in this process. The exemplary transducer elements were configured to be 100 μm×100 μm squares separated by 200 μm.

Figure 4A:
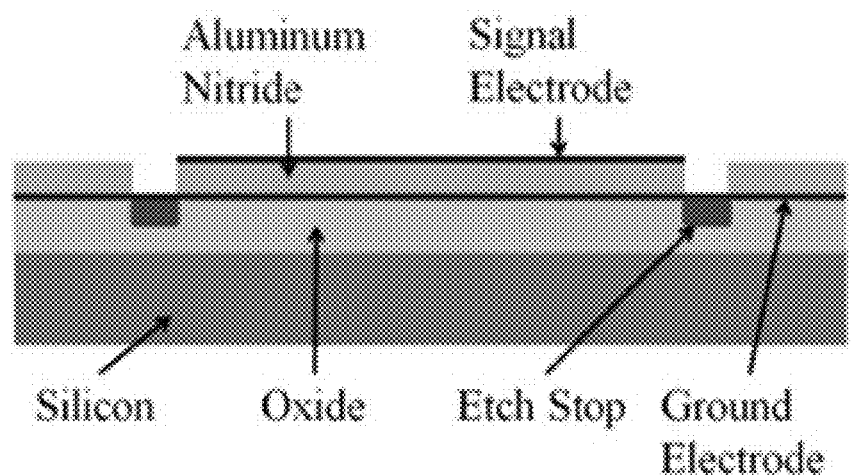
FIG. 4A shows a cross-sectional view of a schematic illustration of one exemplary piezoelectric transducer element produced using an exemplary fabrication process.
Figure 4B:
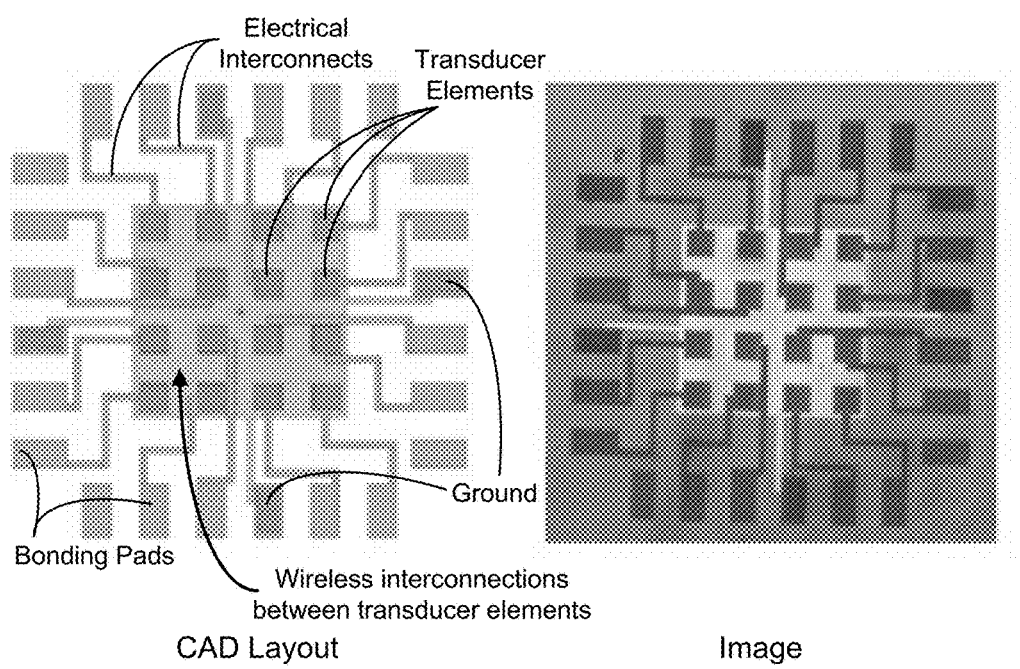
FIG. 4B shows a top view of a CAD layout diagram and an image of an exemplary acoustic in-chip communication device produced using an exemplary fabrication process.

FIG. 4A shows a cross-sectional view of a schematic illustration of one exemplary piezoelectric transducer element fabricated using the exemplary RF MEMS process. FIG. 4B shows a top view of a CAD layout diagram as well as an image of the exemplary acoustic in-chip communication device fabricated using the exemplary RF MEMS process. As shown in FIGS. 4A and 4B, the exemplary acoustic in-chip wireless communication device includes a 4×4 array of the piezoelectric transducer elements each electrically coupled to an electrical bonding pad via corresponding electrical interconnections. The exemplary device includes contact pads that are electrically coupled to the ground electrode of the device.

Figure 5A:
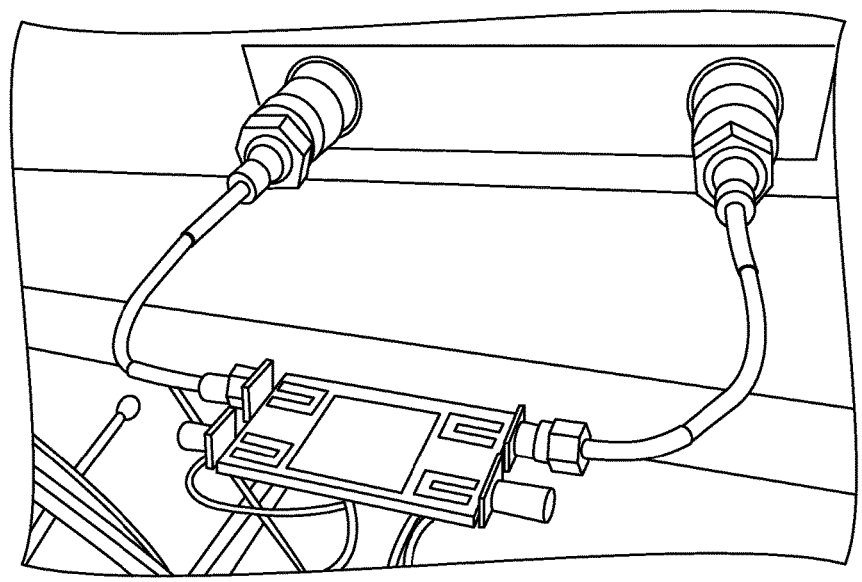
FIGS. 5A and 5B show an image and schematic illustration depicting an exemplary acoustic in-chip communication device in an exemplary implementation setup configuration.
Figure 5B:
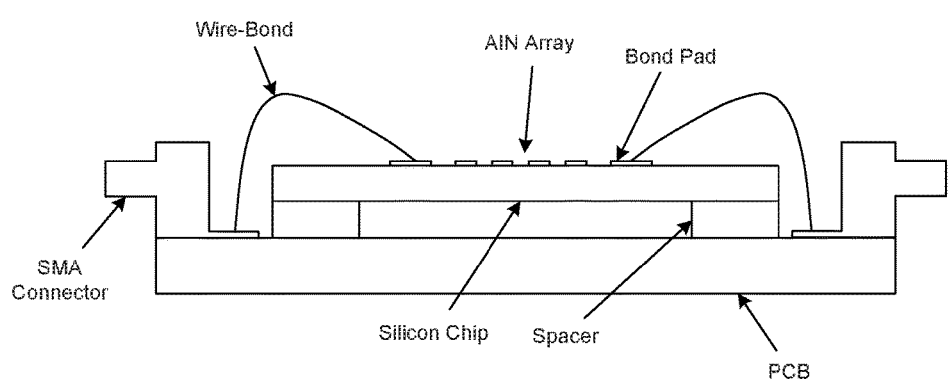

The exemplary fabricated silicon die with the aluminum nitride arrays was mounted to a printed circuit board (PCB) to perform tests using an HP8753ES RF network analyzer, as shown by the image in FIG. 5A. The PCB houses SMA ports to interface with RF equipment. The die was mounted on the PCB on top of spacers. For example, this allows the bottom of the silicon to be exposed to air creating a large contrast in acoustic impedances resulting in a strong reflection at the bottom surface. For example, if the exemplary chip device were secured to the PCB underneath, part of the sound waves would may propagate into the PCB due to its material, e.g., FR4, having a much closer acoustic impedance to silicon compared to air. This exemplary configuration prevents a large loss in signal power transmitted to the target. Wire-bonding pads on the chip, which are used for electrical connections to the PCB, were placed away from the sites of the active piezoelectric elements, e.g., so as to reduce sonic coupling into the wires. FIG. 5B shows a cross-sectional view of a schematic illustration of this exemplary setup.

Figure 6A:
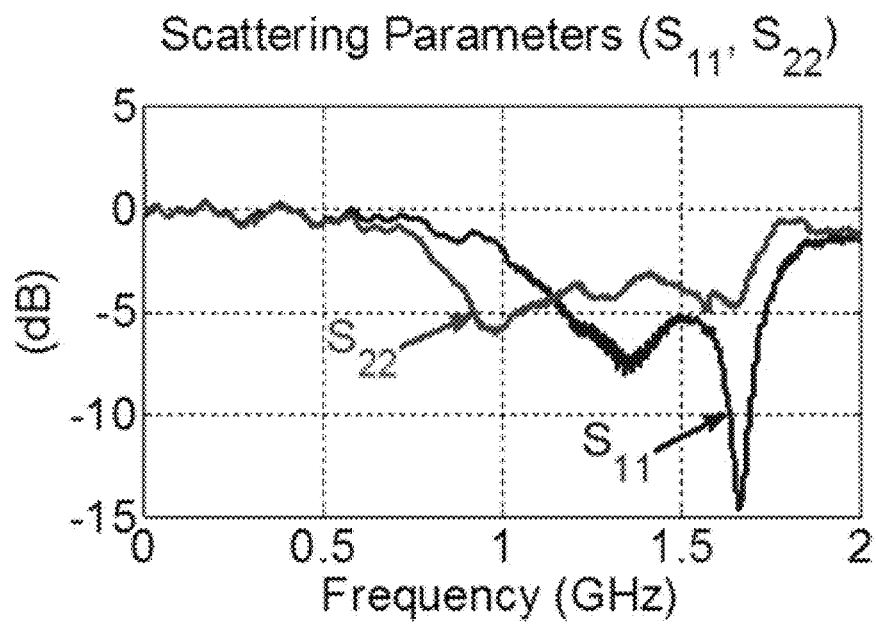
FIG. 6A shows a data plot showing exemplary results of reflection scattering parameters for the two transducer elements in an exemplary sonar array in-chip communication device.
Figure 6B:
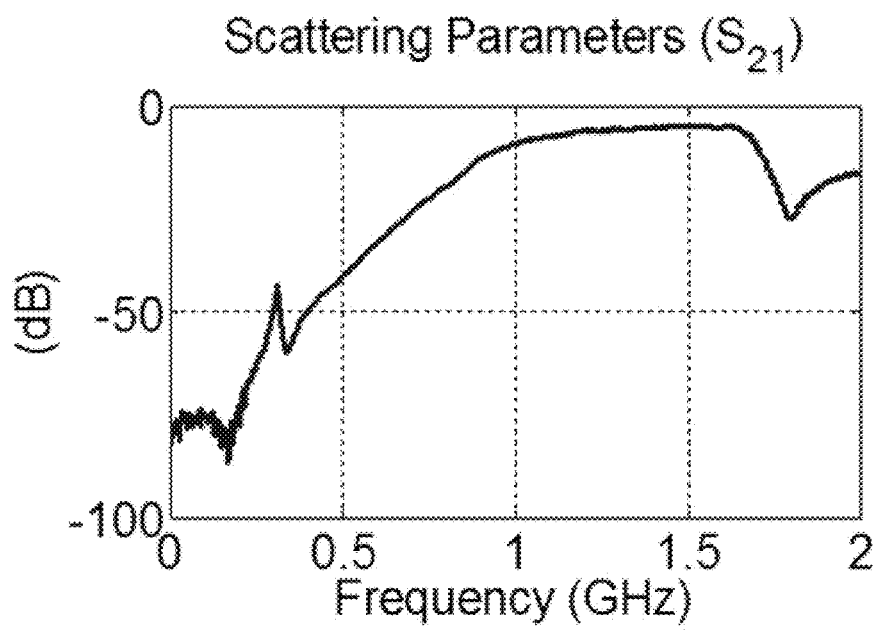
FIG. 6B shows a data plot showing exemplary results of a transmission scattering parameter for the two exemplary transducer elements in the array.

In one exemplary implementation, two pixels in the array of the exemplary device shown in FIGS. 4A-5B, which are 400 μm apart, were wire bonded to the SMA connectors for measurement of the scattering parameters using the network analyzer. For example, reflection scattering parameters $S_{11}$ and $S_{22}$ correspond to the reflection of energy back into the port under the implementation, as shown in FIG. 6A. Exemplary results of the implementation showed that there are peaks at 1.34 GHz and 1.66 GHz, which are the fundamental resonant modes of the exemplary device. These are the modes at which ultrasonic energy is most easily injected into the silicon substrate. FIG. 6B shows a data plot showing exemplary results of a transmission scattering parameter, $S_{21}$, for the two exemplary transducer elements in the array. The $S_{21}$ parameter shows that from 1.06 GHz to 1.67 GHz there is a loss of only 5 dB. This exemplary implementation demonstrates exemplary bandwidth of communication between these two elements.

As shown in these exemplary implementations, exemplary ultrasonic phased arrays in-chip communication devices can be integrated on chip to enable pulses to be transmitted from any location to another by beam steering for reconfigurable communication links. Exemplary results showed acoustic coupling between the transducer elements in the array, e.g., by measuring the reflection scattering parameters of the two exemplary microfabricated, 100 μm×100 μm AlN transducer elements, which are spaced 400 μm away within the same 4×4 array.

In some aspects, the disclosed array of CMOS-integrated piezoelectric transducer (sonar) modules can be integrated into a 3D chip-stack to enable pulses to be transmitted from any location to another by beam steering. An array of sonar elements can transmit sound pulses through stacks with mechanical connections.

Figure 7A:
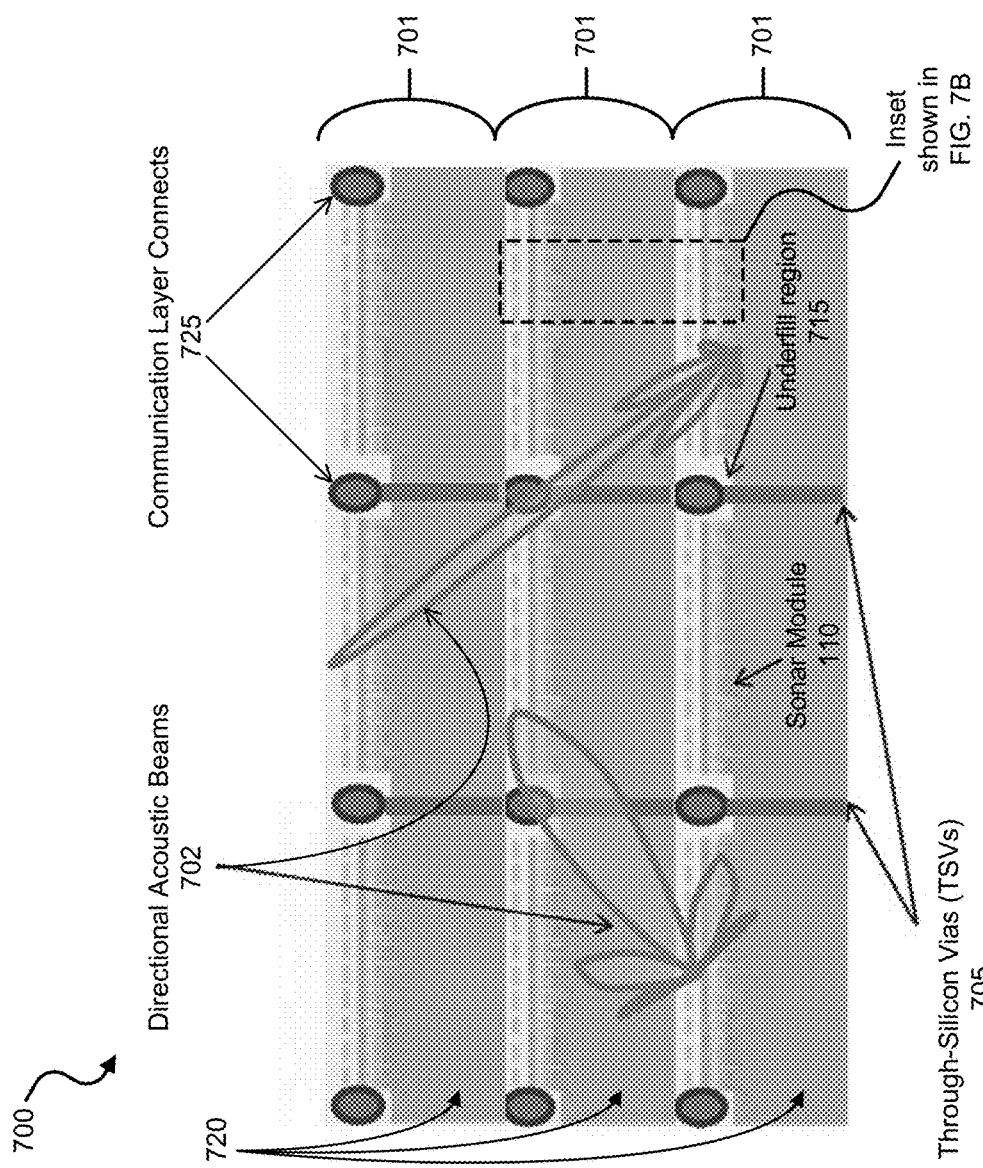
FIG. 7A shows a schematic illustration of an exemplary 3D chip-scale wireless communications IC device.

FIG. 7A shows a schematic illustration of an exemplary 3D chip-scale wireless communications IC device 700 including a plurality of layers 701 of arrays of the acoustic transceiver (sonar) modules 110 capable of transmitting and receiving directional acoustic communications signals 702 in a single layer and between multiple layers. Each of the layers 701 are structured to include dielectric sub-layer 720 to provide an acoustic propagation medium for the acoustic communication signal 702 (e.g., ultrasound wave) to propagate within the device 700, e.g., including between sonar modules 110 of the arrays. The device 700 can include an underfill region 715 between dies and around bumps to provide continuous propagation medium transitions between the layers 701. As previously described and shown in FIGS. 1C-1F, each or any of the sonar modules 110 of the device 700 can be structured to include a sub-array of individual piezoelectric transducer elements 130 (shown in FIG. 1D). The sub-array of individual piezoelectric transducer elements 130 can be communicatively linked to underlying electronic control circuits including driving/read circuits and logic circuits. The device 700 can include a plurality of through-layer vias (TLVs) 705, e.g., in this example represented as through-Silicon vias, which can be used for electronic control signal routing, e.g. including power and clock signal routing. The device 700 can include communication layer interconnections that connect the electronic control circuits in each layer to the TLVs 705.

Figure 7B:
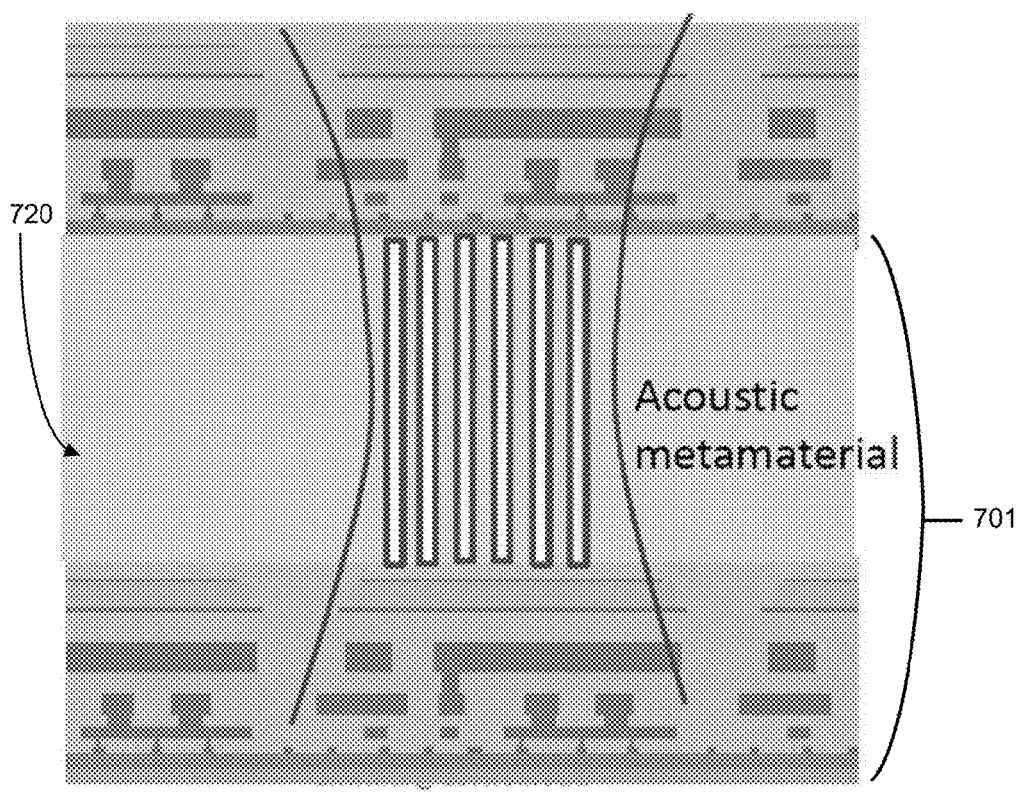
FIG. 7B shows an inset schematic from FIG. 7A showing an exemplary configuration of the acoustic propagation medium sub-layer.

FIG. 7B shows an inset schematic from FIG. 7A showing an exemplary configuration of the acoustic propagation medium sub-layer 720 including artificial structures as acoustic metamaterials to guide the sonic signals, e.g., effectuating the directional acoustic communication signal 702. In implementations, the acoustic metamaterial can function as an acoustic waveguide to promote more efficient transmission of acoustic waves from one point to another. It can also include frequency filtering functionality to transmit only ultrasonic waves of certain frequency (wavelength) or mode (shear or longitudinal waves) while attenuating or obstructing the passage of undesired frequencies or modes.

In some aspects, the disclosed technology includes fabrication methods to produce 2D and 3D in-chip wireless communication signaling devices.

In one exemplary embodiment, a method to fabricate exemplary chip-scale wireless communications IC devices, e.g., including the devices 100 and 700, can include AlN deposition techniques to form the piezoelectric transducer arrays. In some examples, sputter deposition of AlN is implemented at low temperatures (range), e.g., to be compatible with CMOS, but may utilize optimum metals like Tantalum for best films. The deposition of AlN at low temperatures also enables the placement of AlN embedded in the metallization stack. In some implementations, PZT thin films can be deposited though the sol-gel process, and require an anneal step which is typically at 700-800° C. This high temperature implies that the process flow for the PZT is to be implemented after CMOS fabrication. For example, PZT films can be transferred onto CMOS-based chips using oxide-oxide bonding, oxide-metal bonding, or metal-metal bonding.

Figure 8:
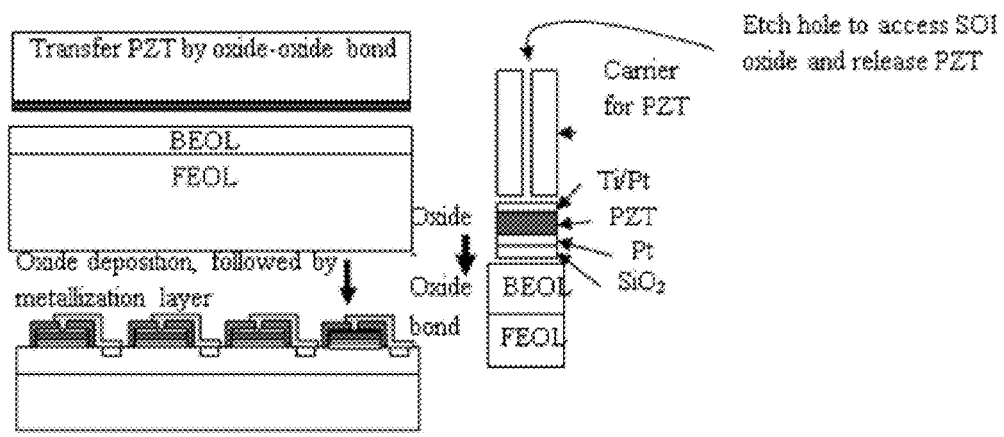
FIG. 8 shows a diagram of an exemplary PZT transfer process to an exemplary CMOS based IC chip.

FIG. 8 shows a diagram of an exemplary PZT transfer process to a CMOS based IC chip, in which a PZT stack is bonded to BEOL oxide-oxide oxide bonding that can be done at low temperatures with follow on processing to enable interconnects to top conductors of the exemplary PZT stack.

Figure 9:
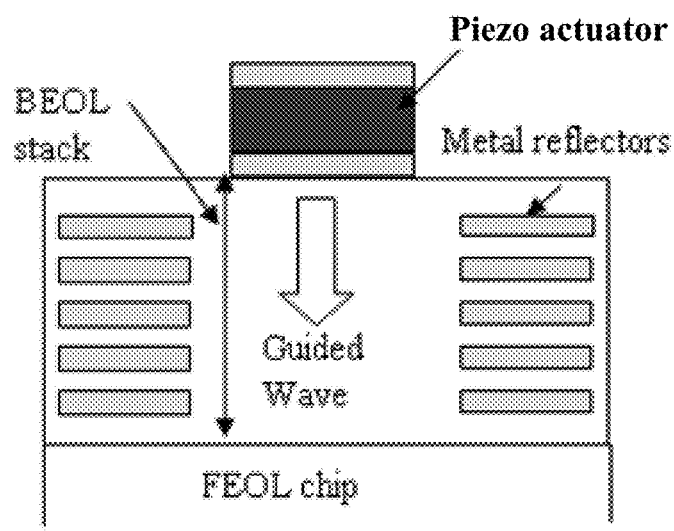
FIG. 9 shows a diagram of an exemplary BEOL stack including metal reflectors to optimize wave coupling to the exemplary semiconductor substrate.

In some implementations for example, the exemplary AlN stack with TEOS oxide layers can form a 1-D waveguide to launch pressure (P) waves, also referred to as longitudinal waves, with the motion transduced into the thickness of the wafer. For such exemplary implementations, the exemplary devices can be designed and fabricated to effectuate the longitudinal wave impedance of the silicon wafer and possible reflections and transmissions through metal layers, e.g., which can be intentionally placed in the IC design to tune the impedance of the transducer. FIG. 9 shows a diagram of an exemplary BEOL stack including metal reflectors to optimize wave coupling to the semiconductor substrate. For example, longitudinal waves can be guided to prevent lateral diffraction based on the metal reflector structures positioned in the BEOL stack, e.g., such that the impedance of an exemplary copper-laden segment can have higher impedance than a TEOS-only segment. For example, the transducer electrical impedance can be calculated using an exemplary 1D model, e.g., including resonances and anti-resonances, and the absolute values of the impedances can lead to calculations of Q (quality factor) and $K^2$ (electromechanical coupling) of the transducers. For example, the value of $QK^2$ can determine the power efficiency of transducer efficiency.

For example, the design and fabrication of the exemplary wireless in-chip communication devices can be implemented to mitigate the effects of shear and SAW waves. For example, in addition to the longitudinal waves, the transducers can couple energy into shear and surface acoustic waves. For a pulse transduction, 67% of the energy is emitted as a surface wave if a surface transducer is used. In some examples, the exemplary techniques can determine the transducers design spacing by spacing the array elements in the stop-band of SAW waves. Longitudinal and shear waves can thus be used for the communication links, e.g., to minimize the coupling of energy into shear and SAW modes, as the wave motion corresponding to these modes will travel at different speeds and different directions, leading to unwanted cross-talk. Similarly, for example, shear waves can be minimized by configuring electrodes in symmetrical geometries to cancel out shear motion.

Figure 10:
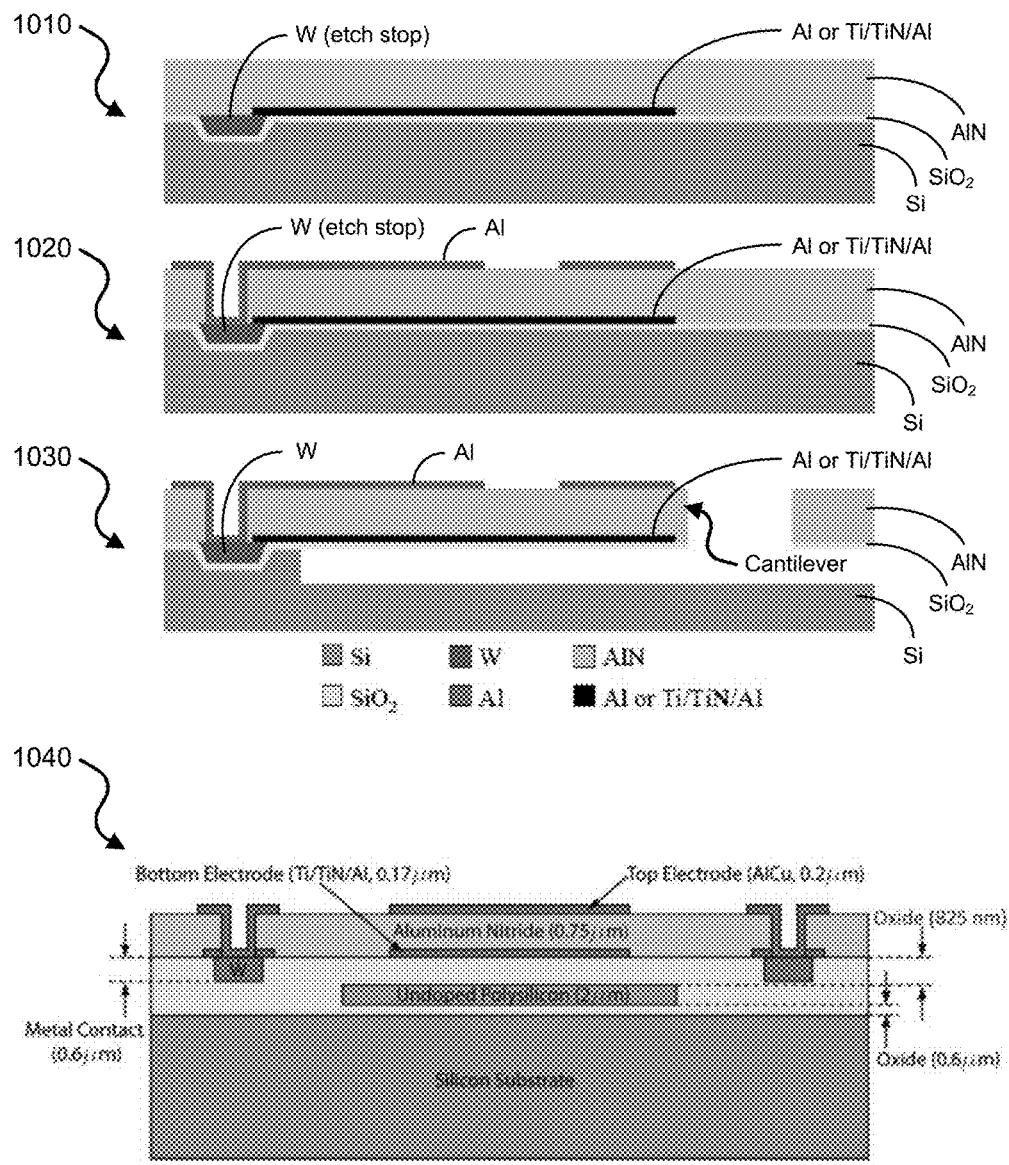
FIG. 10 shows a process diagram of an exemplary fabrication technique to produce wireless in-chip communication devices of the disclosed technology.

FIG. 10 shows a process diagram of an exemplary fabrication technique to produce wireless in-chip communication devices of the disclosed technology including piezoelectric transducer elements formed on a cantilever beam or any other structure to act as a resonator. For example, this resonator characteristic can provide frequency selectivity during both transmission and detection as the ultrasonic transducer can generate (launch) or receive acoustic waves from its anchor, allowing resonant sensing and actuation. The exemplary fabrication technique can include a process 1010 to form the initial layers of materials of the piezoelectric resonator transducer. In the example shown in the process 1010, AlN is formed over a silicon oxide layer over a silicon substrate, in which a Al or Ti/TiN/Al layer is formed between the silicon oxide and AlN layers, and in which tungsten is formed in a cavity of the silicon substrate and/or silicon oxide layers to form an etch stop. The fabrication technique can include a process 1020 to etch into the layers of the materials and deposit an Al layer. In the example shown in the process 1020, a well is etched into the AlN layer above the W etch stop and an Al layer is subsequently patterned over the portions of the AlN layer including the etched well above the W etch stop. The fabrication technique can include a process 1030 to form the cantilever structure. The process 1030 includes etching away a sacrificial layer to have cavities or unconstrained boundaries around the acoustic transducer element. For example, one advantage of resonant sensing is that it can perform better to detect low amplitude acoustic signals on the receiver side. In the example shown in the process 1030, a portion of the AlN, silicon oxide, and silicon substrate are etched to isolate a cantilever structure underneath a portion of the silicon oxide layer and Al or Ti/TiN/Al layer below the AlN layer covered by the Al layer. The materials and process steps shown in FIG. 10 are examples, and other material and/or structural designs can be implemented to fabricate the exemplary piezoelectric resonator transducer structures for the disclosed wireless in-chip communication devices. FIG. 10 includes a diagram 1040 showing a cross-sectional view of an exemplary piezoelectric resonator transducer including an undoped polysilicon layer within the silicon oxide layer.

In some aspects, the disclosed technology includes devices and techniques for direct CMOS integration with the disclosed ultrasonic transducers, e.g., including the piezoelectric transducer elements configured in a layer adjacent to a layer of CMOS transmit and receive electronics on the same wafer. For example, such integration reduces load capacitance and inductance by minimizing interconnect and routing area and by eliminating wire bonds. The reduction of the load capacitance presented by the interconnects between the electronics and the piezoelectric transducer elements can lower transmit amplitudes such that higher receive amplitudes can be obtained. Also, a reduction in area allows more transducers and electronics to be integrated in the IC device. Furthermore, parasitic capacitances and inductances from the interconnects and routing between control circuits and transducer elements can be kept to minimum in the disclosed IC designs, such that their effect on the frequency response of the transmit and receive circuitry is negligible. Also for example, in some implementations, the transmit and receive electronics corresponding to a sonar pixel can be configured directly beneath the transducer element such that the problem of signal crosstalk between wiring carrying signals from different pixels is minimized.

The disclosed technology can include a variety of circuits for controlling the phase or delay of pixel excitation waveforms. Described are two exemplary circuit topologies that can be implemented in the exemplary control electronics for controlling the phase or delay of the acoustic waveforms: delay generation through inverter based delay lines and the generation of phase shifts through quadrature mixing.

In one example, digital delay lines can be used to obtain the necessary delays. These exemplary delay lines can include one or more inverter delay elements, such as those shown in FIG. 11A, in series. For example, such delay elements are essentially inverters whose propagation delay is adjusted by varying the supply current, the load capacitance or the supply voltage. Thus the amount of time that each delay line can delay the input signal can be adjusted by varying one or more control voltages and by the number of delay elements that are in cascade. Instead of using just the output from the end of a delay line, tapped delay lines where the output after each delay element is accessible may be used for finer delay resolution.

Figure 11A:
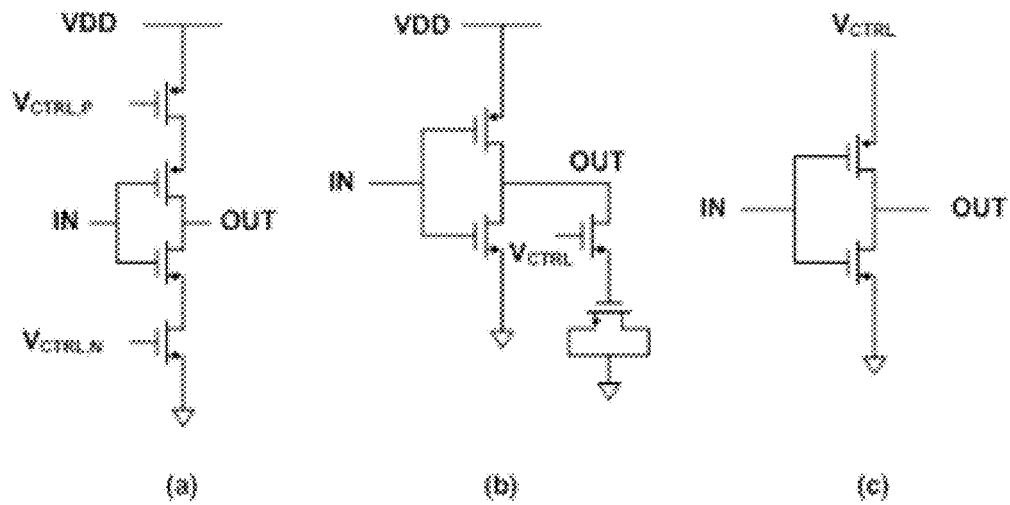
FIG. 11A shows diagrams of exemplary delay lines including one or more inverter delay elements.
Figure 11B:
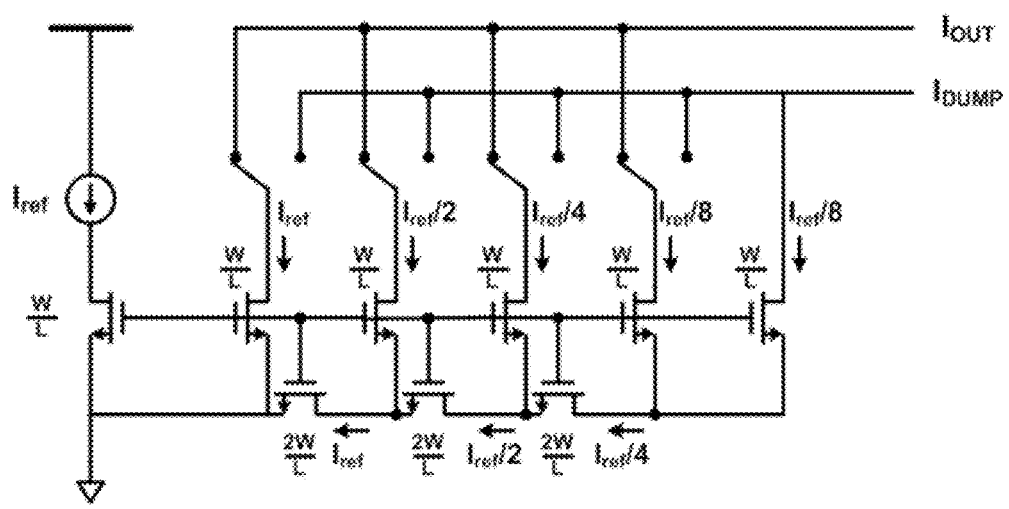
FIG. 11B shows a diagram of an exemplary 4-bit current splitting D/A converter.

For example, the delay control voltages or current sources, as in the case of the current starving topology in FIG. 11A(a), can be generated by storing digital values on-chip in digital memory such as SRAM and using a digital-to-analog (D/A) converter to obtain the analog voltages or currents. For example, per pixel, D/A converters are relatively large components that can affect the size of the electronic area consumed by the pixel. An example of one of the smallest D/A converter topologies includes current splitting or current steering D/A converters, which includes a current mirror comprising N+1 transistors of unit size W/L and N−1 transistors of 2 W/L. N switches of at least 2 transistors each are used to set the D/A converter output current by switching between the output node or a dump node. FIG. 11B shows a diagram of an exemplary 4-bit current splitting D/A converter. For example, to reduce the size and/or power consumption requirements that having one or more D/A converters per pixel would impose, an appropriate analog memory topology can be used as described further below.

Figure 11C:
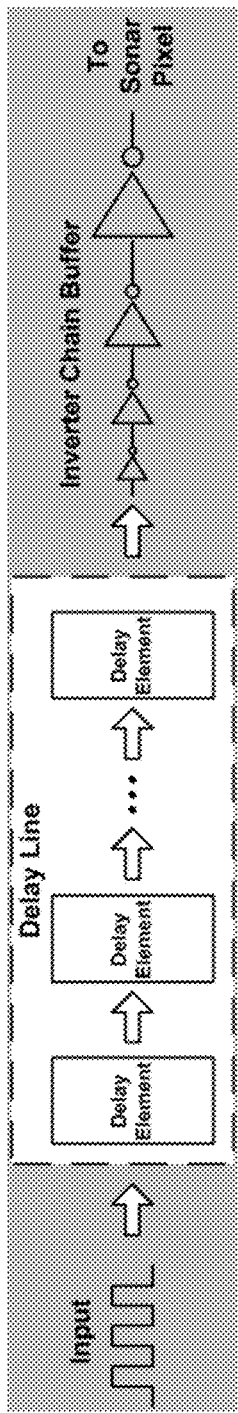
FIG. 11C shows a diagram of an exemplary delay line circuit followed by inverter chain buffer.

FIG. 11C shows a diagram of an exemplary delay line circuit followed by inverter chain buffer. For example, while minimum size inverters can be used for fine delay resolution and to minimize circuit area in each pixel, the output inverter used to drive the sonar should be large enough to drive the capacitive load that the piezoelectric elements present. For example, as large inverters also can present a large capacitive load at their inputs, instead of using a single inverter as the output buffer, an inverter chain with progressively increasing inverter sizing can be used to minimize the loading effect at the buffer input, as shown in FIG. 11C.

In another example, phase shifting a sinusoidal waveform can be implemented to generate the necessary delays. For example, the phase shifting is implemented through a quadrature mixing scheme, e.g., including two analog weights A and B that are multiplied with waveforms $\sin(\omega t)$ and $\cos(\omega t)$, respectively, and then added for an output waveform of A $\sin(\omega t)$+B cos ($\omega t$). For example, this is equivalent to an output of C $\sin(\omega t+\varphi)$, where C is $\sqrt{A^2+B^2}$ and $\varphi$ is $\tan^{-1}(B/A)$. Constant amplitude phase shifting can be obtained by selecting the analog weights A and B to be C cos $\varphi$ and C sin $\varphi$, respectively, where C is the desired output amplitude and $\varphi$ is the desired output phase.

Figure 11E:
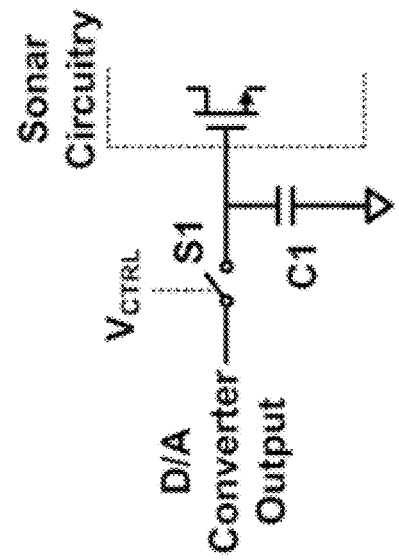
FIG. 11E shows a diagram of an exemplary unit cell of an analog memory.
Figure 11D:
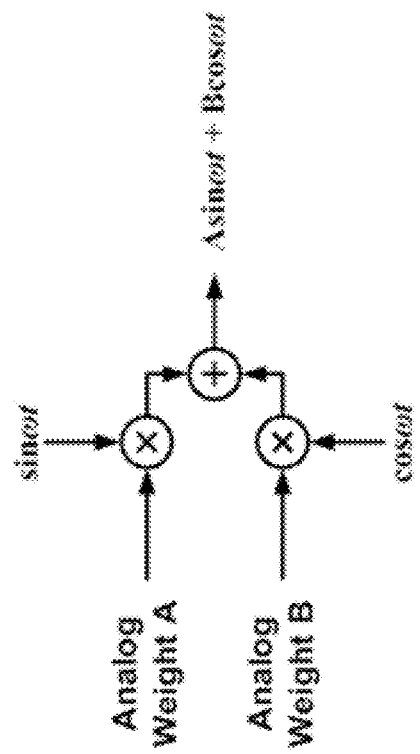
FIG. 11D shows a diagram of an exemplary quadrature mixing circuit for amplitude and phase shift control with two analog weights.

FIG. 11D shows a diagram of the exemplary sinusoidal phase shifting that can be implemented by a typical quadrature modulation circuit, and analog voltages that are applied to the mixer inputs. As in the exemplary inverter delay line topology, they can be generated by on-chip storage of digital weights that are subsequently converted to analog voltages through D/A converters. For example, the mixers can be implemented with generic Gilbert cell mixers with output nodes connected such that the summing occurs through current addition. For example, the sinusoidal voltages sin ($\omega t$) and cos($\omega t$) can be generated by applying a signal with frequency $2\omega$ into a frequency divider circuit, which will output two signals at frequency $\omega$ that are 90 degrees in phase apart. The output of this quadrature phase shifting circuit can be pulsed through the use of appropriately placed switch transistors.

For example, to implement a large number of sonar pixels, it is desired to keep the power and area consumed by the supporting electronics as low as possible. As an exemplary alternative to implementing multiple DACs per pixel, an analog memory for analog weight storage can be used instead. For example, each D/A converter can be replaced by a cell comprising of a single capacitor C1 and a switch S1 used to selectively write to the capacitor. FIG. 11E shows a diagram of an exemplary unit cell of an analog memory. For example, in some implementations of the disclosed devices, metal-insulator-metal (MIM) capacitors may occupy layers in the metal stack above the transistor layers and below the sonar transducer layer. For such implementations, for example, the use of such capacitors can effectively reduce the area required for pixel electronics, despite the relatively large size. In the exemplary unit cell of an analog memory, the capacitor stores the analog voltages required for the sonar circuitry, e.g., either the control voltages for delay lines or the analog weights for phase control. A single or a few global D/A converters can be used to generate these analog voltages for all of the pixels. For example, to set the analog weight on a pixel, the DAC is first set to the desired value and then the access switch for the appropriate capacitor is turned on. Once the capacitor charges to the desired voltage, the switch is turned off and the next capacitor can then be charged. Due to leakage effects, the capacitor voltage must be periodically refreshed. While a single transistor or a transmission gate can be used for the switch, various low leakage switch topologies can also be used.

Several modifications can be made to this exemplary analog memory architecture to increase leakage tolerance. For example, by switching to a differential input mixer topology and using two of the capacitor based analog memory cells instead of a single one, the voltage difference of the two cells is used as the input and thus the effect of leakage can be greatly reduced. Alternatively, active analog memories which employ some form of leak compensation can be used. For even longer term storage, instead of using a capacitor, non-volatile storage elements such as floating gate transistors can be used instead.

Figure 11F:
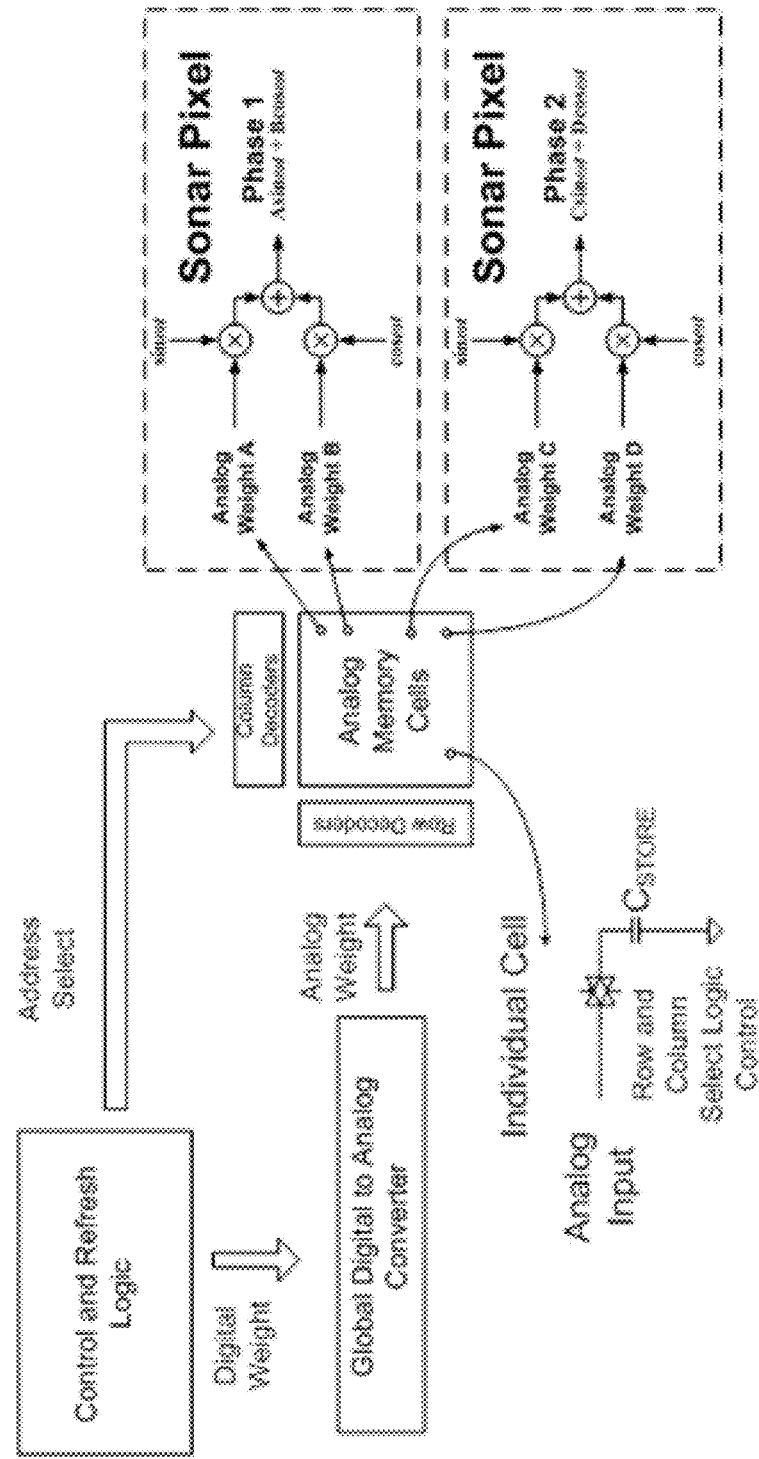
FIG. 11F shows a diagram of an exemplary analog memory for multiple phase generation.

FIG. 11F shows a diagram of an exemplary analog memory for multiple phase generation, which can be integrated into the electronics for each sonar pixel.

Other methods of delay generation derived from ultrasonic imaging systems may also be implemented. In some examples, the transmit path of an ultrasonic imaging system typically includes the transmit beamforming electronics followed by a high voltage pulser. Multilevel pulsers can be used to send signals of different output voltages, which can be used in beamforming. As sufficient receive amplitudes can be obtained while driving the sonar transducer at amplitudes below the nominal supply voltages for transistors on advanced process nodes, a high voltage driver is not necessary.

As the transmit beamformer for ultrasonic imaging applications is typically digital in nature, shift registers or timer/counter circuits may be used to implement the transmit delays. For example, for the case of a counter, instead of applying an input waveform and delaying it, a comparator can be used at the counter outputs to generate a trigger signal once the counter reaches a certain value. This exemplary trigger signal then activates a pulser circuit which outputs a single or multiple pulses at the desired voltage, pulse width, and frequency. For example, delay resolution can be improved by employing clock division with delay locked loop based circuits.

The above-disclosed technology can be implemented in various devices and systems, and applied to various of applications.

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules. Nano-sized materials used to create a nanostructure, nanodevice, or a nanosystem that can exhibit various unique properties, e.g., including optical and electronic properties, that are not present in the same materials at larger dimensions and such unique properties can be exploited for a wide range of applications.

Techniques, systems, and devices are described for implementing for implementing computation devices and artificial neurons based on nanoelectromechanical (NEMS) systems.

Perceptron architectures use a number of computational neurons and learning techniques to adjust the weights depending on the agreements of the outputs of the neurons to input patterns (Hebbian learning). Because the success of the neural computing topologies when performing pattern recognition depend on the number of computational neurons used, much work has focused on providing a higher density of computational neurons and connectivity, attempting to rival the biological neuron densities exhibited in the human brain. For example, CMOS quadrant multiplier arrays in conjunction with analog memory in the form of stored charge on capacitors have been used to form analog CMOS neurons. These approaches consume significant power due to bias currents required for the analog multipliers, compounded by leakage currents in active mode in highly scaled transistors. For example, to maintain a biologically equivalent power budget of 50 W for $10^{11}$ neurons, implies 0.5 nW per neuron, further implying an average bias current of 1 nA assuming 0.5 V power supply. These currents are too low for proper operation of even deep-subthreshold analog designs. Furthermore, the synaptic connection density to other neurons is limited both by the size of the multipliers and by interconnect densities enabled with planar processes.

Table 1 shows the power and area associated with CMOS analog and CMOS digital budgets for adders and multipliers, as well as for that of an exemplary NEMS implementation. In digital systems, the $\frac{1}{2}CV^2$ is determined by the number of transistors at the given technology node.

TABLE 1

| FUNCTION | ADDER | | MULTIPLIER | |
| --- | --- | --- | --- | --- |
| | Power-Delay (digital) or Power/Bandwidth (analog) | Area | Power-Delay (digital) or Power/Bandwidth (analog) | Area |
| CMOS - analog | 0.5 mW/55 MHz = 9.1 pJ [Nsour99] | 135 × 145 µm² = 19575 µm² [Nsour99] | 5.5 µW/200 kHz = 27.5 pJ [Gravati05] AMI 0.35 µm, current mode | 18700 µm² [Gravati05] AMI 0.35 µm, current mode |

TABLE 1-continued

| | ADDER | | MULTIPLIER | |
|---|---|---|---|---|
| FUNCTION | Power-Delay (digital) or Power/Bandwidth (analog) | Area | Power-Delay (digital) or Power/Bandwidth (analog) | Area |
| CMOS-digital | 28.3 pJ [Lin12] TSMC 180 nm, Full-adder | 65 µm² [Lin12] TSMC 180 nm, Full-adder | 25.3 mW × 10.19 ns = 258 pJ [Huang05], TSMC 180 nm, 32-bit | 71,907 µm² [Huang05], TSMC 180 nm, 32-bit |
| NEMS-analog | Capacitive addition - No extra power | Capacitive addition - No extra area | 0.4 fJ | 2 × 3 µm² = 6 µm² |

Described herein is NEMS (Nano Electromechanical Systems) technology to realize multipliers and adders that operate with bias currents on the order of femto-amps at voltages of less than one volt, for example, across capacitances on the order of femtowatts. Hence the power consumed in such multipliers can be on the order of femtowatts.

In the discussion below, a perceptron refers to a network of building blocks (also referred to as "computational neurons") that is operable to multiply the inputs by weights, sum the multiplied terms, and then use a nonlinear function to determine if the neurons should produce output pulses. A "synapse" refers to a weights used to multiply within the computational neuron.

FIG. 12 shows examples of building blocks of an NEMS analog computation device for multiplication and addition. More specifically, FIG. 12A shows that an applied voltage across the air/vacuum gap of capacitor formed by two micromechanical beams beam1 and beam2 generates an electrostatic force proportional to $(V_a-V_b)^2$. In some implementations, beam1 is attached to the substrate, formed from a SOI wafer and DRIE etching. After DRIE etching, the structure is undercut such that beam2 is free to bend and is still anchored at the two ends. The two beams beam1 and beam2 are at potentials $V_a$ and $V_b$, respectively. The two beams beam1 and beam2 form a building block actuator.

FIG. 12B shows the displacement of released beam2 for the case when there is no voltage difference between beam1 and beam2 (top plot) as opposed to the case when there is a voltage difference between the two beams (bottom plot). A voltage across the capacitor formed by the two beams leads to an electrostatic force, pulling released beam2 toward the fixed beam1. The force across the two beams that are at voltages $V_a$ and $V_b$ is $$F = \frac{\varepsilon_0 A}{(g_0-x)^2}(V_a-V_b)^2,$$

where $\varepsilon_0$ is the permittivity of air, $g_0$ is the initial gap, and x is the displacement due to electrostatic force. In the exemplary case the displacement x is going to be much less than the gap g, and then the force can be written as $$F = \frac{\varepsilon_0 A}{g_0^2}(V_a-V_b)^2.$$

The current across this capacitor is dominated by the Fowler-Nordheim tunneling current. This current is typically in fA/um² for 15V/um electric fields, providing the basis of average DC power consumption of femtowatts.

The building block actuator can be combined to form analog multipliers. FIG. 12C shows the representation of an exemplary capacitive multiplier by placing two beam1-beam2 combinations. The weight of the structure shown in FIG. 12C is also referred to as a "synaptic weight". As shown in FIG. 12C, in addition to the two beams, two additional clamped-clamped beams beam3s attached to the moving beams are placed such that they get pulled in the same directions as beam2 by the electrostatic force. Furthermore, an electrical isolation block is placed in the connecting beam. The length of the isolating beam can be sufficiently larger than the gaps so that any capacitive coupling across input and output can be minimized. In addition, a beam4 is also placed as the electrode for the output voltage $V_{out}$. A voltage $w_{i,j}$, equivalent to a synaptic weight, is applied across the clamped-clamped cantilever beam3s. Input voltages $x_i$ and $-x_i$, same signal with opposing polarities, are applied to the two beam1s respectively, to electrostatically actuate the two beam2s. The force acting on the two beams with two opposite input polarities can be written as $$F_+ = \frac{\varepsilon_0 A}{2g^2}(x_i+w_{i,j})^2, \quad (6)$$

$$F_- = \frac{\varepsilon_0 A}{2g^2}(-x_i+w_{i,j})^2.$$

The net force is the sum of F+ and F−, where the quadratic terms cancel out, and only the products remain. This motion can be used to transduce the product term of $x_i$ and $w_{i,j}$.

Capacitive Product Transduction

Referring back to FIG. 12C, note that on each side of the output middle electrode (beam4), the beam displacement changes the capacitance. The displacement of the beams modulate the capacitances ($C_{j+}$ and $C_{j-}$). The capacitor divider leads to a voltage on the center beam (beam4) that is equal to the difference of the two capacitances which can be expressed as:

$$V_{out} = V_{in}\frac{C_1-C_2}{C_1+C_2}.$$

The individual capacitance values can be found as follows:

$$C_1 = \frac{\varepsilon_0 A}{g+x_1},$$

$$C_2 = \frac{\varepsilon_0 A}{g+x_2},$$

where $x_i$ and $x_2$ are found from $$x_1 = \frac{F_+}{k} \text{ and } x_2 = \frac{F_-}{k}.$$

In the above expressions, k $$\left(\text{e.g., } k = \frac{16Ewt^3}{L^3}\right)$$

is the spring constant of a clamped-clamped cantilever beam. By substituting these values into the expression for $V_{out}$ the following expression is obtained:

$$V_{out} = \frac{\varepsilon_0 A L^3}{16 g^3 E w t^3} w_{i,j} x_i. \quad (7)$$

One important assumption made to get (7) is that the displacements $x_1$ and $x_2$ are small compared to the gap length g.

FIG. 12E shows an array of capacitive multipliers in FIG. 12C cascaded across the synapses for generating the sum of products. By cascading many multipliers sections, the capacitive sensing wires can be routed to add the total capacitance change, or sum all of the products. The total output voltage from the array of capacitive multipliers is then:

$$V_{out} = \frac{\varepsilon_0 A L^3}{16 g^3 E w t^3} \sum_{i=1}^{N} w_{i,j} x_i. \quad (8)$$

The operating voltages can be chosen such that the beams never touch and hence will not suffer from stiction, which is one of the concerns in NEMS reliability. Because the multiplication and adding operations in the array of capacitive multipliers shown in FIG. 12E are achieved through capacitive/electrostatic actuation of micromechanical beams without using transistors, these operations require almost no DC power in such architecture, possibly limited by leakage current across insulating layers.

The product of the weight and input is related to the difference between the two capacitances. Since these capacitances are not constant, the sum of the two capacitances will cause a nonlinearity in the circuit read-out. The change in capacitance is small compared to the magnitude of the capacitance; this expression is approximately linear. A simulation is run using this expression for the following design parameters: beam length is 3 um, width is 2 um, thickness is 50 nm, and gaps are 50 nm. FIG. 13 shows the resulting plot of simulated output voltages from the capacitive multiplier of FIG. 12C using the above dimensions.

For the chosen dimensions and the voltages shown in FIG. 13, the simulated output signal shows less than 2% nonlinearity. The output voltages do not exceed 20 millivolts but can be amplified. Resolution of this system can be analyzed from thermal noise considerations which lead the following expression for the RMS displacement of the beam, $$\overline{x_n^2} = \frac{4\sqrt{m} k_B T}{k^{\frac{3}{2}}} \Delta f,$$

where m is the mass of the beam, $k_B$ is Boltzmann constant, T is temperature, k is the spring constant, and $\Delta f$ is the bandwidth. Using this expression for displacement, the RMS value of the output voltage due to thermal noise is on the order of 10 nV. This leads to a dynamic range of 60 dB given the maximum unamplified signal amplitude of 20 mV as mentioned before.

Another useful metric is the resonance frequency and hence the upper bound frequency of device operation. Considering the geometries as described above, the resonant frequency can depend on the spring constant and the mass of the beam. For the previously mentioned geometry, the resonant frequency is 190 MHz. This frequency can be increased by shortening the beam dimensions, which also allows optimization between noise and dynamic range of the overall system. For instance, decreasing the beam length from 3 μm to 1 μm results in a resonant frequency of 1.7 GHz, an RMS noise level of 2 nV, and a signal level of 0.2 mV.

Piezoresistive Product Transduction

While FIG. 12C provides an implementation of a multiplier using a capacitive approach, the multiplication operation can also be implemented based on piezoresistivity. FIG. 12D shows the representation of an exemplary resistive multiplier by placing two beam1-beam2 combinations.

In FIG. 12D, the capacitance beams beam3s and beam4 in FIG. 12C have been replaced by a piezoresistive beam. As the two beam2s pull the center beam5, they cause strain of beam5 such that some part of the beam5 will be in tension while some part of beam5 is in compression. By including an electrode configuration as shown, the net change in resistance will be a function of the products of the weights and the inputs. FIG. 12F shows an array of pizeoresistive multipliers in FIG. 12D cascaded across the synapses for generating the sum of products. In a similar manner to the cascaded capacitive multiplier in FIG. 12E, the resistances can be cascaded and the net change in the resistance will be the sum of the individual products. The central beam can be both heavily doped silicon, and also graphene. The heavily doped silicon beams is a low-risk approach to get results, as its piezoresistivity is a well-established technology, and many devices can be made using silicon piezoresistors, and have an established process flow of the fabrication. A good reason to pursue graphene piezoresistivity is the exemplary result on giant piezoresistivity in grapheme.

Figure 12G:
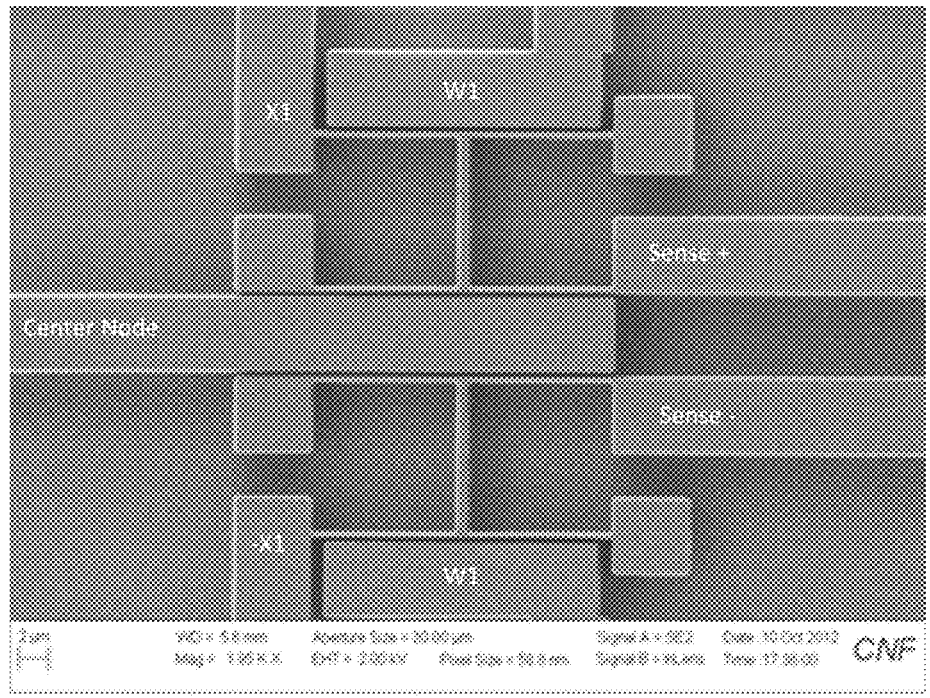
FIG. 12G shows an SEM image in top view of an implemented MEMS-based capacitive multiplier.
Figure 13:
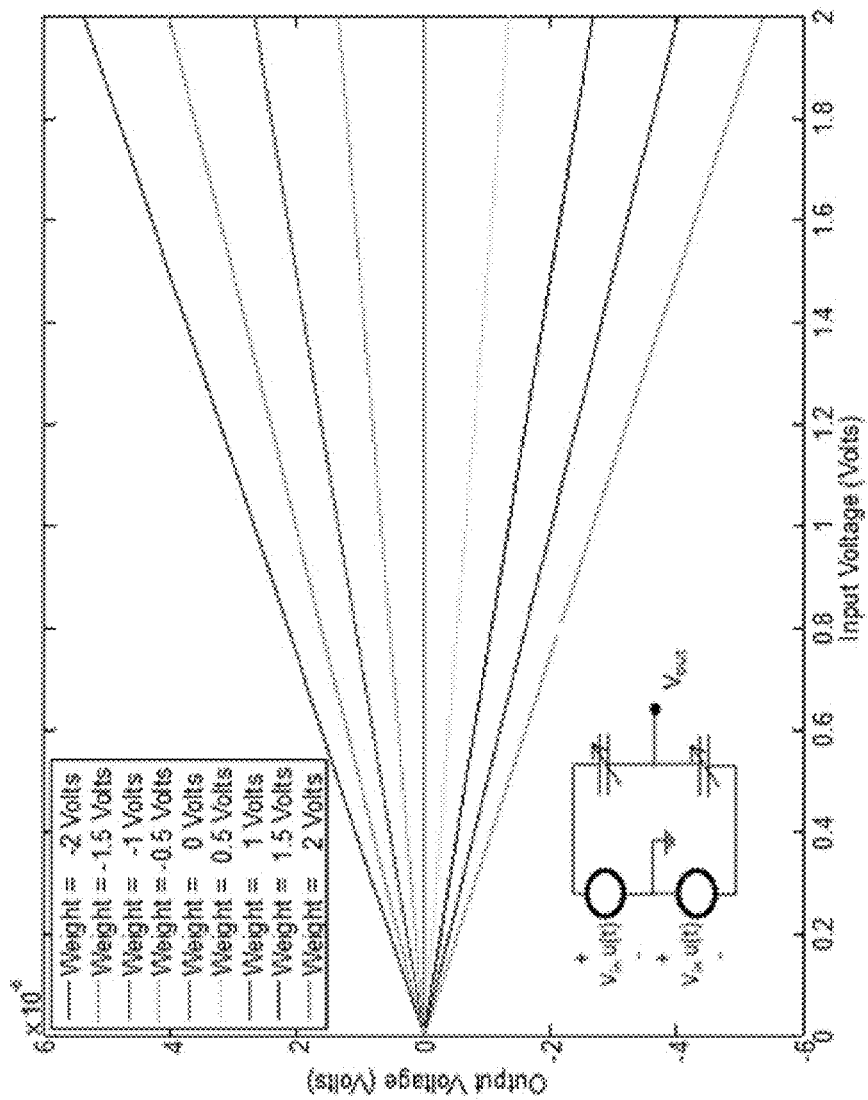
FIG. 13 shows the resulting plot of simulated output voltages from the capacitive multiplier of FIG. 12C using the above dimensions.

FIG. 12G shows an SEM image in top view of an implemented MEMS-based capacitive multiplier. The two variable capacitors which enable the multiplier function are defined between (1) the "Sense+" node and the "center node" and (2) the "Sense−" node and the center node. In order to drive the changes in the capacitances, the nodes labeled as W1, X1 and −X1 are driven with the respective voltages described-above in conjunction with FIG. 12C. In the illustrated implementation, Sense+ and X1 are electrically shorted together and Sense− and −X1 are electrically shorted together. Using this configuration, the multiplier inputs and weight (X1, −X1, W1) are driven with DC voltages while Sense+ and Sense− are driven with AC voltages.

Figure 12H:
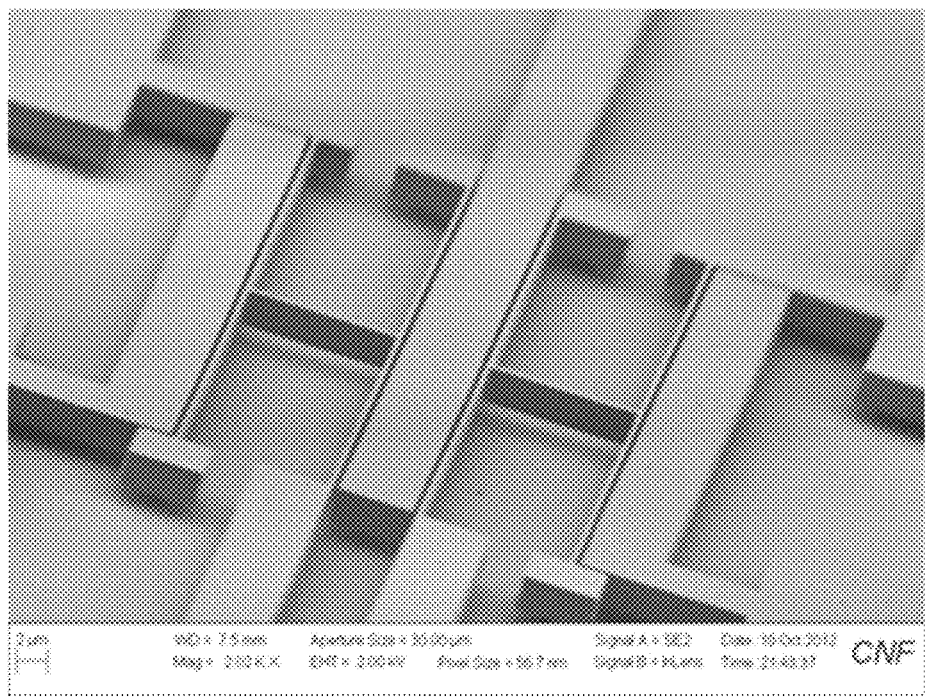
FIG. 12H shows an SEM image in perspective view of the MEMS-based capacitive multiplier shown in FIG. 12G.

FIG. 12H shows an SEM image in perspective view of the MEMS-based capacitive multiplier shown in FIG. 12G.

Figure 12I:
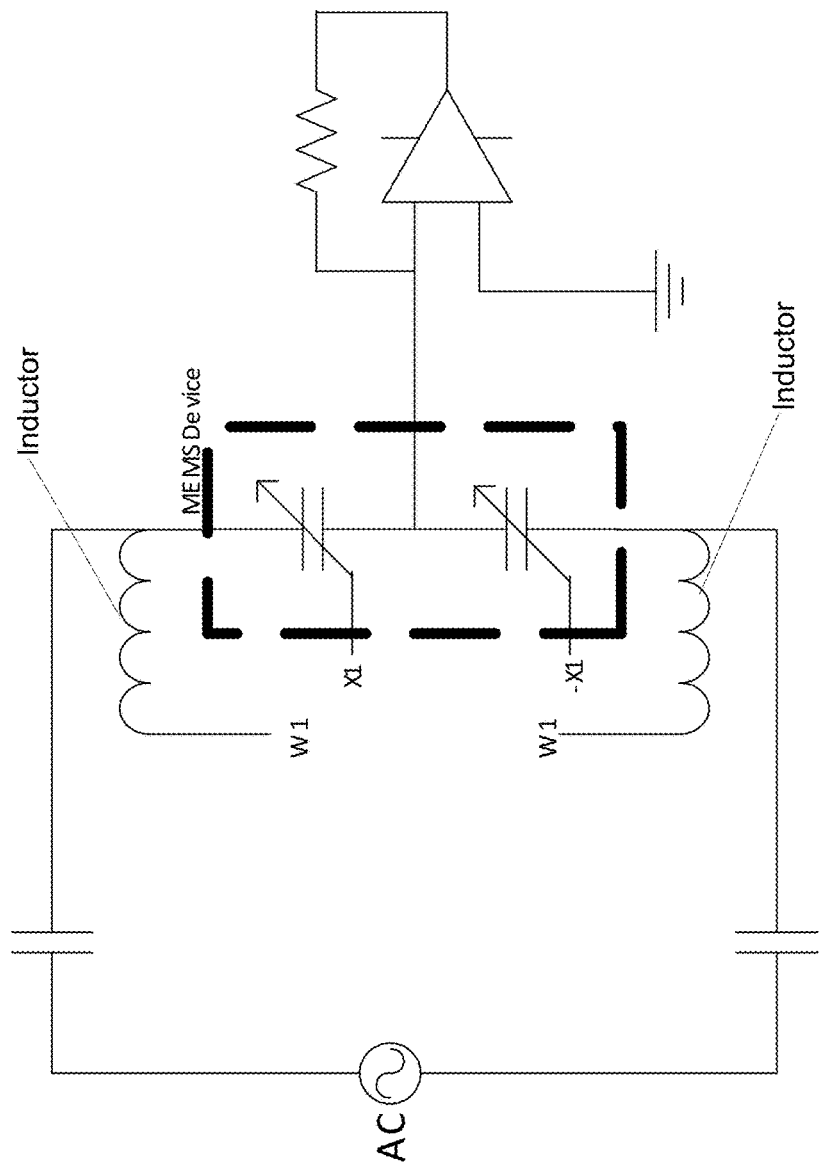
FIG. 12I shows an equivalent circuit (within the dashed line) of the MEMS-based capacitive multiplier in FIGS. 12F-12G and other peripheral circuits.

FIG. 12I shows an equivalent circuit (within the dashed line) of the MEMS-based capacitive multiplier in FIGS. 12F-12G and other peripheral circuits. Because the weight voltages are DC voltages and electrically coupled to the sense nodes, to sense the changes in a capacitance, an AC signal (X1 or –X1) is driven into the multiplier through the capacitance. As can be seen, an inductor may be used to block variations on each of the weight voltage inputs. Also in this embodiment, an op-amp configured as a transimpedance amplifier is used at the device output to sense changes in the capacitance.

Figure 12J:
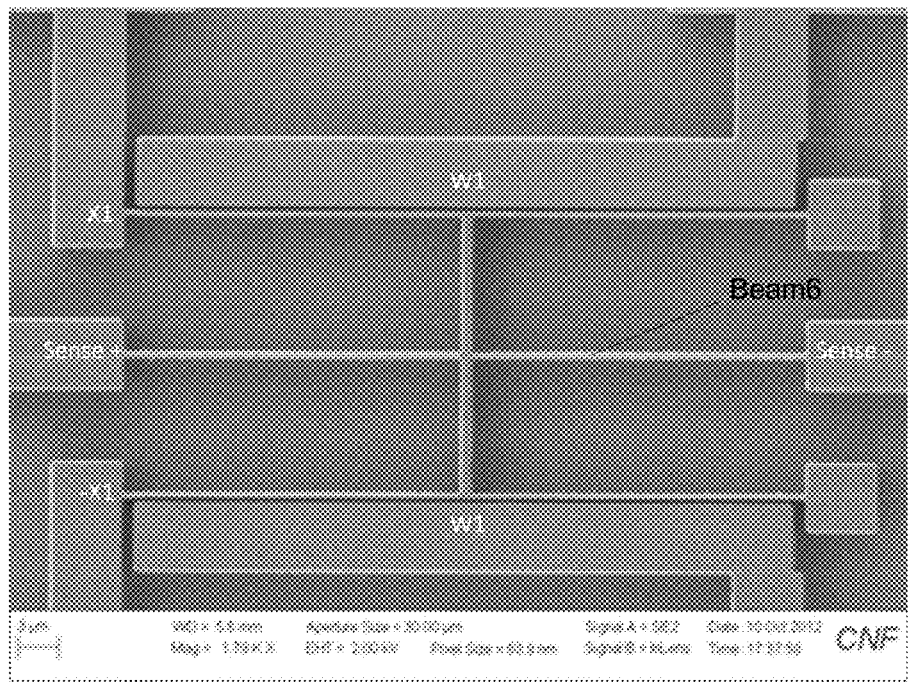
FIG. 12J shows an SEM image in top view of an implemented MEMS-based piezoresistive multiplier.

FIG. 12J shows an SEM image in top view of an implemented MEMS-based piezoresistive multiplier. As described above in conjunction with FIG. 12D, the central beam beam6 in the piezoresistive device will change in resistance when undergoing deformation. In other words, the resistance between sense nodes "Sense+" and "Sense–" will change as the beam6 connecting them deforms. This deformation is caused by a combined effect due to the changes in gaps between (1) the capacitor plates of X1 and W1 and (2) the capacitor plates of –X1 and W1.

Figure 12K:
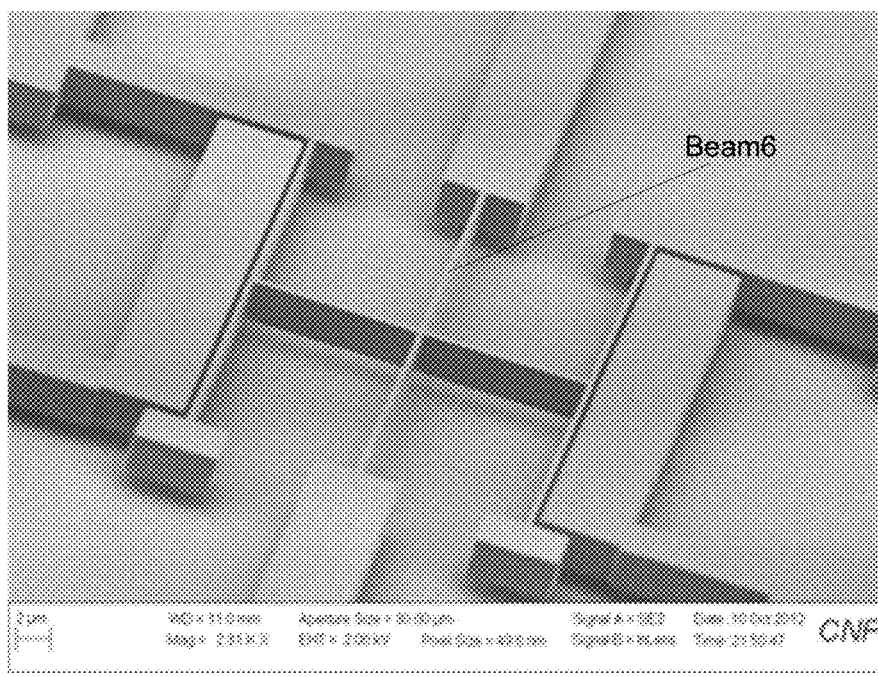
FIG. 12K shows an SEM image in perspective view of the MEMS-based piezoresistive multiplier shown in FIG. 12J.

FIG. 12K shows an SEM image in perspective view of the MEMS-based piezoresistive multiplier shown in FIG. 12J.

Figure 12L:
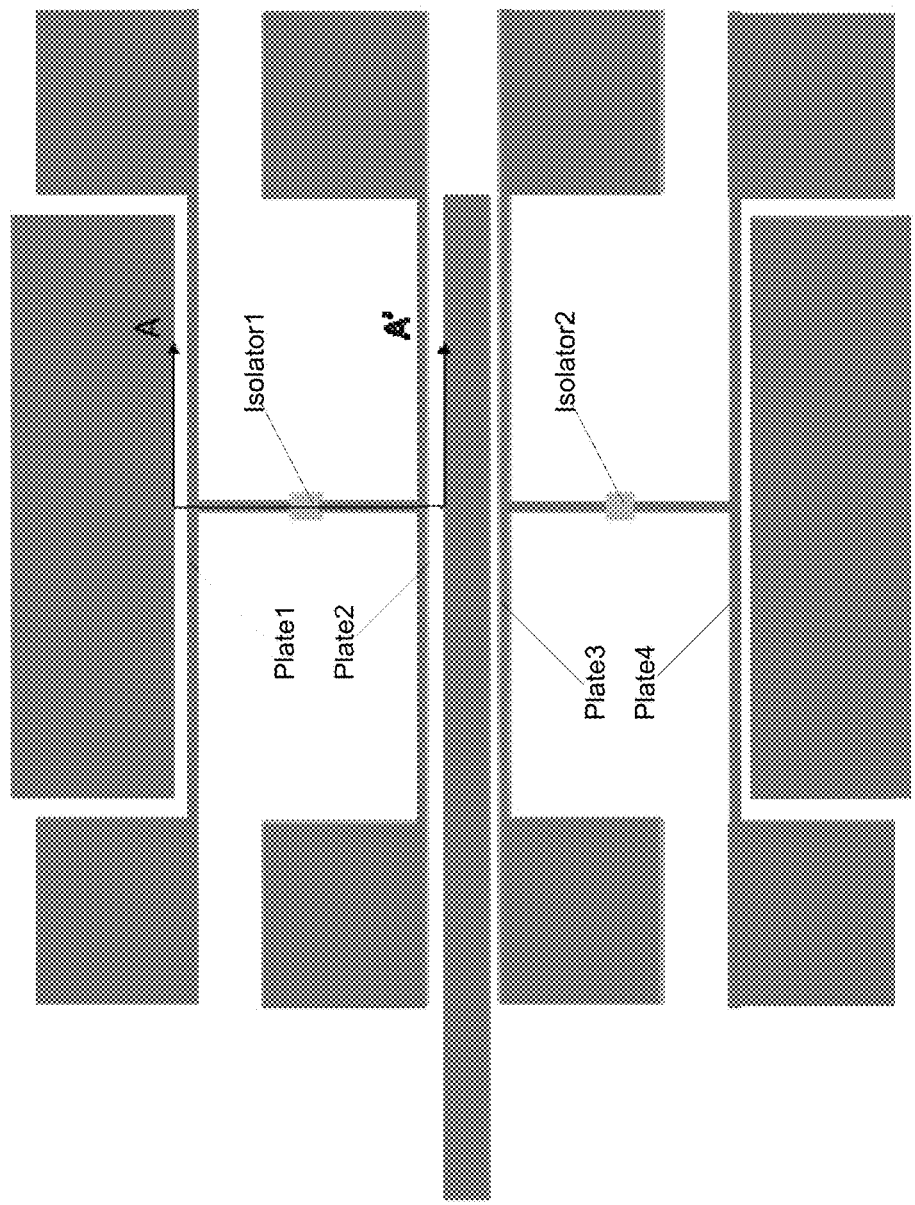
FIG. 12L shows an example implementation of adding an electrical isolation to the armature connecting the two capacitor plates plate1 and plate2 and plates plate3 and plate4 in the MEMS-based capacitive multiplier shown in FIG. 12G.

FIG. 12L shows an example implementation of adding an electrical isolation to the armature connecting the two capacitor plates plate1 and plate2 and plates plate3 and plate4 in the MEMS-based capacitive multiplier shown in FIG. 12G. More specifically, the electrical isolations insulator1 and isolator2 (in orange) are silicon nitride and the insulators are used to electrically separate a corresponding pair of capacitor plates.

FIG. 12M illustrates a process flow for fabricating the MEMS-based capacitive multiplier including the silicon nitride electrical isolation as viewed from a cross-section of AA' in FIG. 12L. The starting structure is an SOI wafer. Next, lithography is used to define and etch a hole into the silicon layer down to the silicon dioxide layer. Next, an deposition of a nitride layer is performed across the entire surface until the hole is filled. A chemical mechanical polishing (CMP) step is then applied to the wafer surface to polish it back to the original silicon surface. Another lithograph step is then applied to define the armature beam by etching through the silicon down to the silicon dioxide layer. Next, vapor HF is used to etch away the silicon dioxide underneath to release the beam structures to obtain the structure shown in FIG. 12L.

CMOS Digital/Analog (D/a) Converter for Capacitive Weights

Figures 14A, 14B:
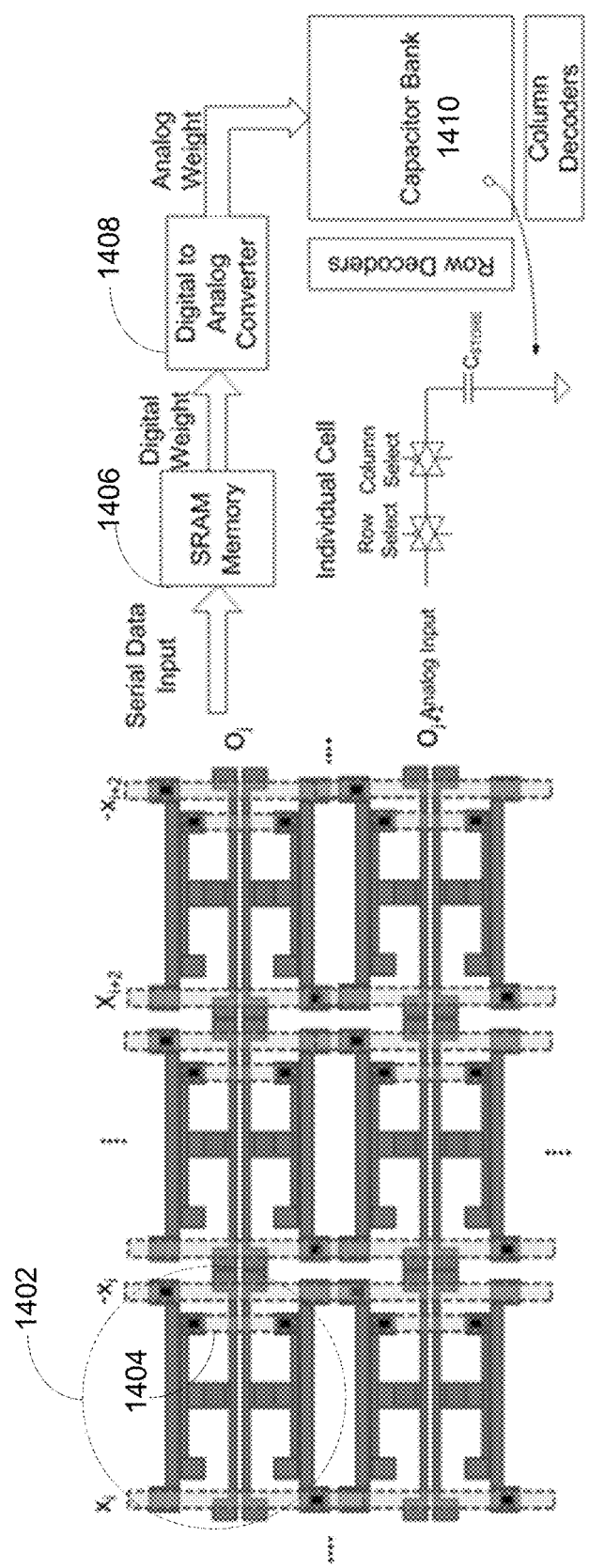
FIG. 14A shows an example of tiling an array of capacitive multipliers and adders in two dimensions to achieve high synapse density.
FIG. 14B shows an exemplary implementation of writing the weights in the tiled 2D multipliers and adders structure.

FIG. 14A shows an example of tiling an array of capacitive multipliers and adders in two dimensions to achieve high synapse density. More specifically, in FIG. 14A, the multipliers and adders are tiled in a 2-dimensional fabric. Each basic building block can have a size of 3-30 um² to achieve a potential of 3-30 million synapses per cm² of chip area. Note that each multiplier block, such as multiplier 1402, is associated with a unique weight 1404, which can be trained and used as a memory element for the synapse array. Moreover, each weight such as 1404 can be implemented by a capacitor so that the weight value can be programmed and then maintained. Because the multiplication and adding operations in the synapses array are achieved through capacitive/electrostatic actuation of micromechanical beams without using transistors, these operations result in almost no DC power consumption in such a computational device. This low power characteristic facilitates achieving high density of synapse array devices which still only consume a reasonable amount of overall power. The power consumption per synapse can be in the range of femtowatts, making it possible to create a computational neuron network that has a neuron density equivalent to neuron density of a human brain. In this computational neuron network, the heat can be dissipated without reaching very high destructive temperatures within a 3-dimensional dense matrix of the NEMS computation elements.

FIG. 14B shows an exemplary implementation of writing the weights in the tiled 2D multipliers and adders structure. In this implementation, the weights are digitally stored in floating point representation in SRAM memory 1406. CMOS D/A converter 1408 in FIG. 14B can convert the digitally stored weights to analog weights which are then written into the capacitors (e.g., capacitor bank 1410) representing the weights in the structure, through multiplexed output. In some implementations, that weights are continuously updated to generate analog weights, which resembles an analog DRAM cell. This implementation provides a relatively low-risk approach in terms of technological approach.

While the NEMS multipliers described above operate in analog domain, conversion of the digital outputs from the digital implementation of a perceptron is necessary. While D/A conversions can be implemented in CMOS technology, Table 1 suggests that NEMS implementations can be used to achieve lower energy per operation and therefore high integration density because using capacitive/electrostatic actuation of beams to replace CMOS transistors requires near zero DC power consumption.

Figure 15:
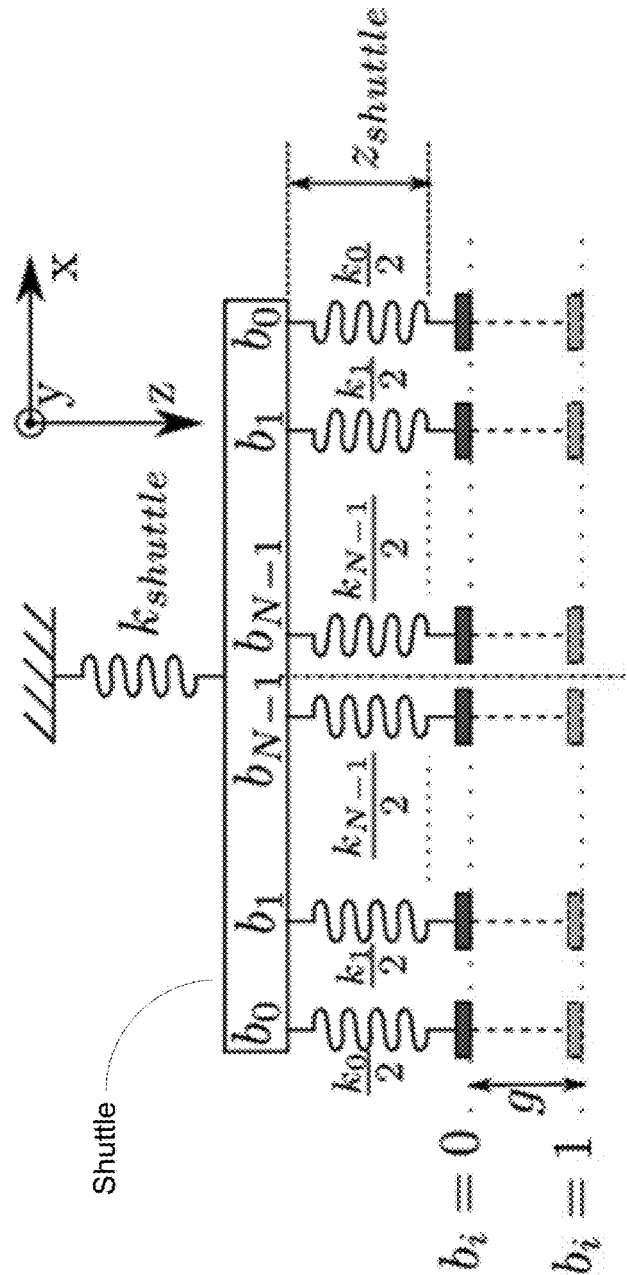
FIG. 15 illustrates the operation principle of a MEMS-based DAC implemented by precision control of positions of MEMS mirrors.

FIG. 15 illustrates the operation principle of a MEMS-based DAC implemented by precision control of positions of MEMS mirrors. As can be seen in FIG. 15, two bit-level electrostatic actuators (which may be identical) are connected to a shuttle symmetrically for every bit $b_i$ of conversion. The coupling spring constants $k_i/2$ between the bit-level actuators and the shuttle are adjusted based on the binary weight/significance of each bit, so that the position of the shuttle (i.e., the displacement $z_{shuttle}$) represents a D/A converted version of the bit sequence. Each of the bit-level actuators is assumed to move down a distance g when $b_i=1$. For example, the operation principle can be quantified as follows.

Assume individual spring constants are designed such that $k_i=k_a(2^i)$ where $i=0, 1, \ldots N-1$, and where $k_a$ is a unit spring constant that is arbitrary based on the design and is equal to the spring constant of the bit 0. Actuator corresponding to bit i moves according to the expression:

$$z_i = \begin{cases} 0, & b_i = 0 \\ g, & b_i = 1 \end{cases}.$$

Figure 16:
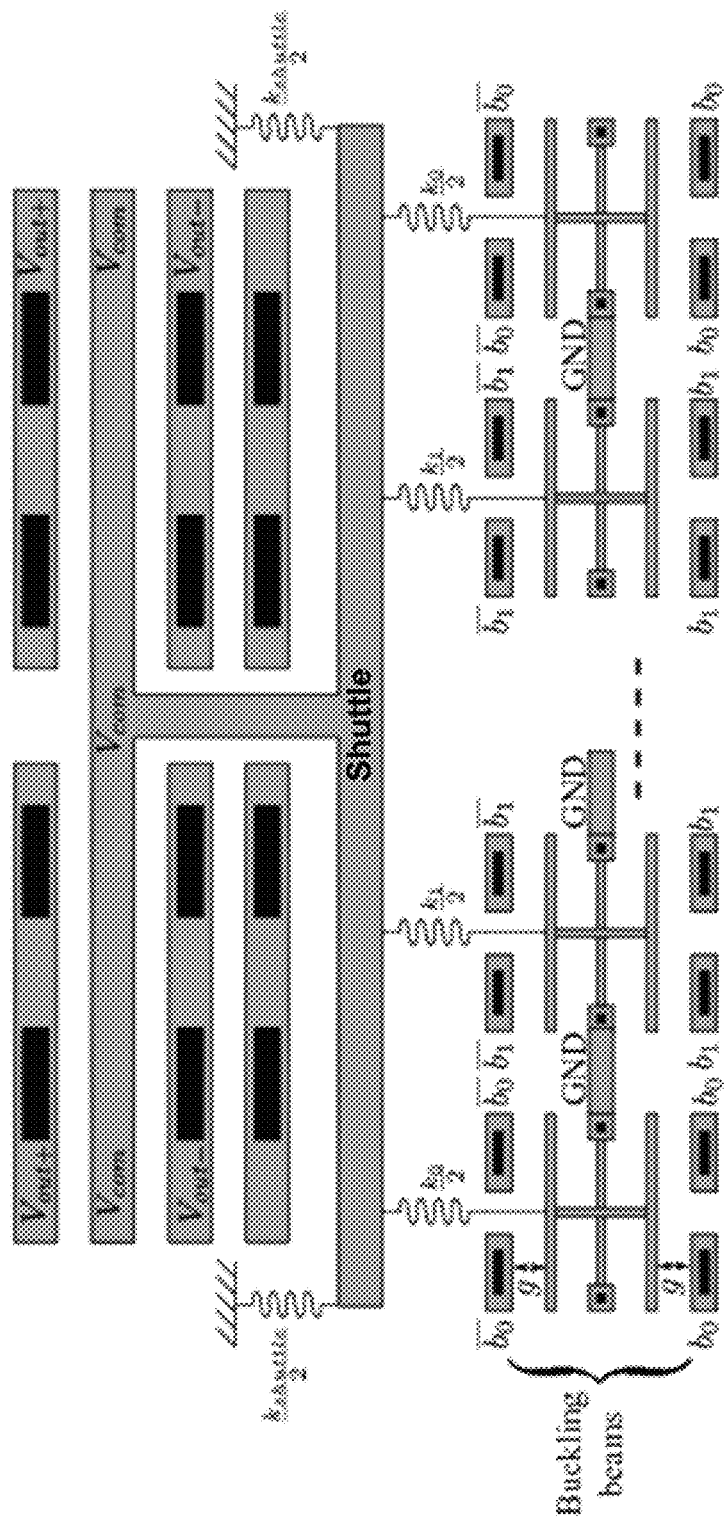
FIG. 16 shows the D/A converter (DAC) implemented with a suspended NEMS that uses buckling beams at the input of each bit-level actuator and capacitive position readout to realize digital to analog conversion.

Denote the sum of spring constants of all actuators as $\Sigma k_i = (2N-1)k_a = k_s$. Then the displacement of the shuttle can be expressed as $$z_{shuttle} = \sum_i \frac{2^i k_a b_i g}{(2^N-1)k_a + k_{shuttle}} = \frac{k_a g}{k_s + k_{shuttle}} \sum_i 2^i b_i,$$

which is the ideal DAC characteristic. Here $k_{shuttle}$ is the spring constant associated with the common shuttle that all the DAC units are mechanically connected to. It is possible to introduce non-volatility to the digital inputs $b_i$ by associating each bit with the bistable state of a buckled beam, essentially acting as a binary memory. FIG. 16 shows the D/A converter (DAC) implemented with a suspended NEMS that uses buckling beams at the input of each bit-level actuator and capacitive position readout to realize non-volatile (indefinite sample and hold at the input) digital to analog conversion. The output of the D/A converter is read differentially using a capacitive readout between the nodes $V_{out+}$, $V_{out-}$, and $V_{com}$. In FIG. 16 the shuttle element is seen to be supported by two parallel connected springs with a spring constant of $k_{shuttle}/2$ leading a total spring constant of $k_{shuttle}$. Individual DAC units are also placed in pairs symmetrically on the left and right to prevent any rotation of the shuttle. The black regions indicate anchors where the structures are attached to the substrate. Note that, inverse of each bit, $\overline{b}_i$, is also used for buckling based actuation of the beam.

Figure 17:
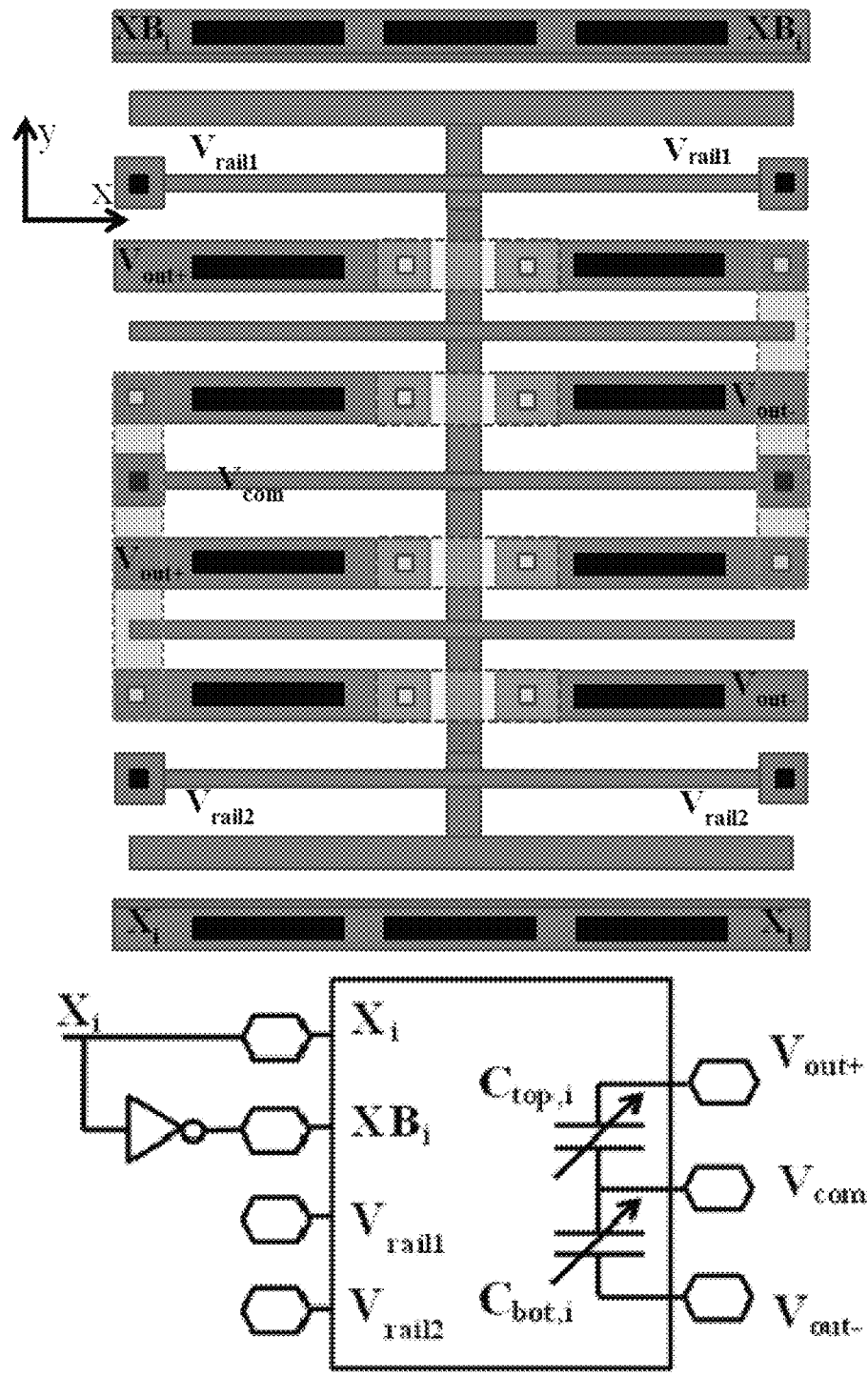
FIG. 17 illustrates an exemplary implementation of the layout and symbolic views of a DAC unit cell that receives bit X, and its inverse XB, as the inputs.

FIG. 17 illustrates an exemplary implementation of the layout and symbolic views of a DAC unit cell that receives bit X, and its inverse XB, as the inputs. Rail voltages are same among all units.

An alternative route to spring constant adjustment for DAC operation can be realized by repetition of unit cells. This exemplary approach can be more robust in the case of fabrication variations in deep-sub-micron processes that can make precise adjustment of spring constants difficult. Here each bit $b_i$ is repeated $2^i$ times based on its binary weight, to avoid precise tuning of spring constants.

Figure 18:
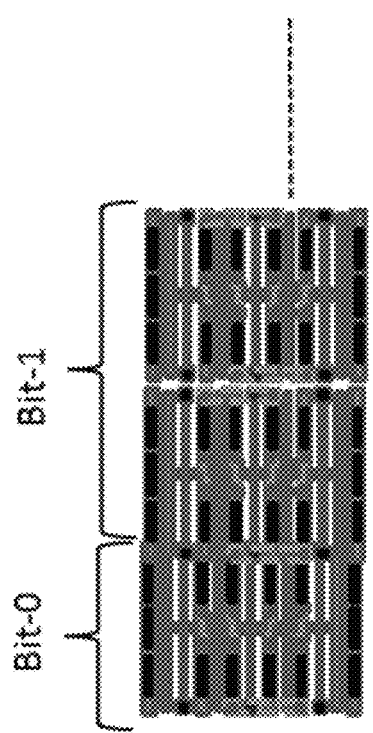
FIG. 18 illustrates an exemplary implementation of layout and schematic level views of stacking of DAC unit cells.
Figure 18:
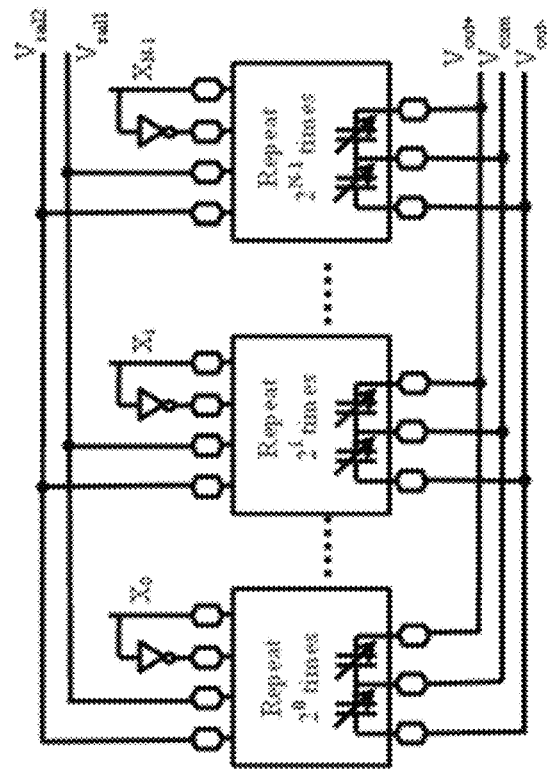

FIG. 18 illustrates an exemplary implementation of layout and schematic level views of stacking of DAC unit cells. Each bit $b_i$ is repeated $2^i$ times based on its binary weight. This technology may be used to avoid precise tuning of the spring constants. Note that similarly to reading a unit cell, the outputs from the stacked cells are also capacitively read through direct connections of the individual bit-level DAC outputs. Such a readout scheme works as a result of the side-by-side stacking.

Figure 19:
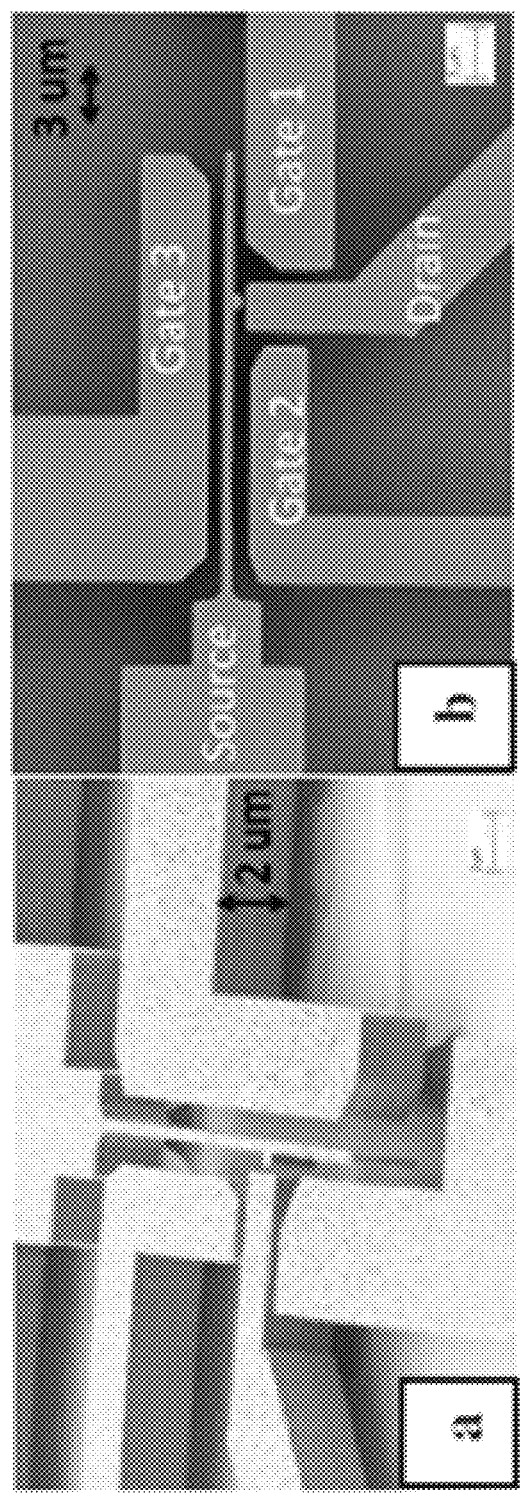
FIG. 19 show perspective and top views of a NEMS-based nanoswitch.

The above-described concept of low power high density integration of perceptron nodes (i.e. "computational neurons") using capacitive actuated beams can be applied to implementing low power high density switches. FIG. 19 show perspective and top views of a NEMS-based nano-switch. The nanoswitch has a contact gap of about 300 nm. In order to reduce the idle power consumption of the CMOS implemented perceptron nodes, NEMS switches that can be actuated with very low actuation voltages can be used, and more importantly at different actuation voltages. As seen in FIG. 19, different electrode gap can result in different pull-in or actuation voltages, that can range from mV to Volts to tens of Volts. This dynamic range in actuation thresholds can assign more importance to some nodes than others, allowing for a wide dynamic range for implementable weights. These exemplary switches can be inserted in series with the main multiply-adder blocks to eliminate the leakage currents and static power consumption of transistors that are significant as compared to dynamic power consumption ($CV^2f$) in deep-submicron technology nodes.

The increase of the number of synapses or neurons to obtain high spatial densities is a key to increasing the effectiveness of artificial intelligence (AI) learning techniques.

Furthermore, the connections among neurons for communication purposes often need to be formed over large distances. The communications for setting up the weights and the connectivity among neurons need to be programmable and power-efficient. The above-described SONAR (Sound Navigation and Ranging) techniques can be used to form a 3D communication networks to read and set the weights of each neuron to facilitate very high fanouts in a programmable manner. At present many efforts are underway to investigate chip-scale optical, magnetic, and RF approaches to signal routing in 3D configuration. These approaches are used for higher bandwidth, but are limited by their fanout capability. The proposed neuron computing architectures require moderate bandwidth, but result in great number of inputs and outputs.

The neuron building blocks can be in the size scale of 20-100 um in all directions. In order to address each neuron individually in a 3D space, a communication channel can be focused into 100-um size volumes. For localization of digital pulses, this means that the associated communication wavelengths also have to be in the 20-100 um range. Acoustic and ultrasonic waves have reasonably low frequencies at such wavelengths, owing to the much lower speed of sound. Hence, beam-forming sonars can be used to construct communication channels, for example, using N piezoelectric pixel elements/actutators. These pixels can focus sonic energy onto different directions in a 3D space, for example, by adjusting the actuation amplitude and phase or time-delay of the N actuators (FIG. 9).

Figure 20:
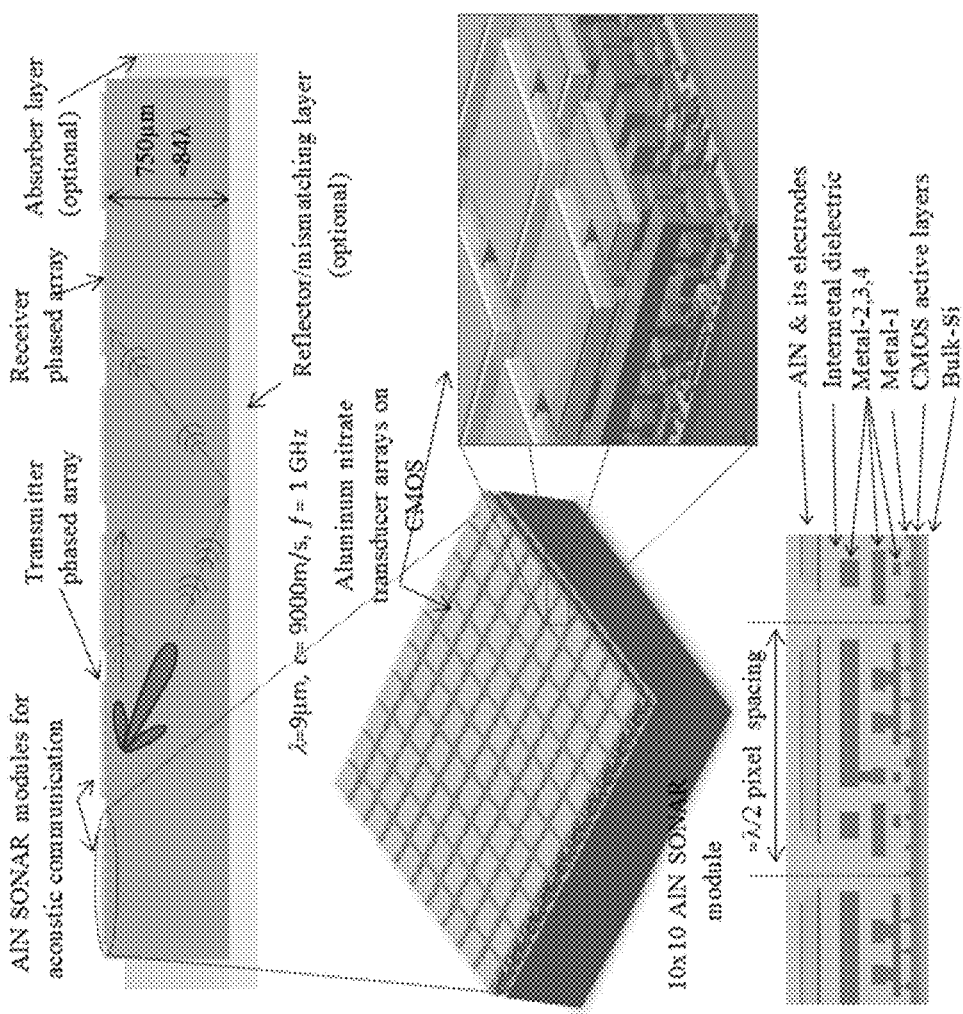
FIG. 20 illustrates aluminum nitride (AlN) SONAR modules built on top of a metallization layer

FIG. 20 illustrates aluminum nitride (AlN) SONAR modules built on top of a metallization layer, which can be a special metallization layer added on top of a CMOS metallization stack. Alternatively, in the case of hybrid integration, a separate AlN sonar array chip can be flip-chip bonded to a CMOS chip electrically connecting the piezoelectric elements to CMOS circuits. The AlN SONAR modules can be implemented as acoustic transmitter modules which are configured to communicate with each other by sending proper phasing of SONAR pulses at desired angles. The transmitted pulses can be reflected off the device boundary and be directed onto an desired destination SONAR element.

In one example, 3D programmable ultrasonic interconnects comprise an array of ultrasonic transducers, operating at 1-GHz, and can generate waves with 9-micron wavelength in silicon. Each transducer itself is a multiple of few half-wavelengths. By developing a phased array of such transducers, a transmitting beam can be focused with approximately 4.5-micron focus. These beams can be used to transmit and listen generated sonic waves. The outputs of each neuron can be used to drive a receiver sonic transducer. This architecture allows for a high degree of 3D integration. Each pulse can be synthesized with a number of acoustic cycles to ensure desired signal to noise ratio at the receivers. The sonic absorption of GHz sound in silicon is very low (~0.1 db/m), due to the high quality factor of silicon. Furthermore, the variations in speed of sound in materials in silicon chips are not substantial leading to transmission of energy through interfacial bonds, metallization layers, and oxide layers. The ultrasonic waves can travel through ultrasonic waveguides with minimal reflection and scattering losses, the minimization of which can be explored by developing sections of each NEMS computational neuron.

Figure 21:
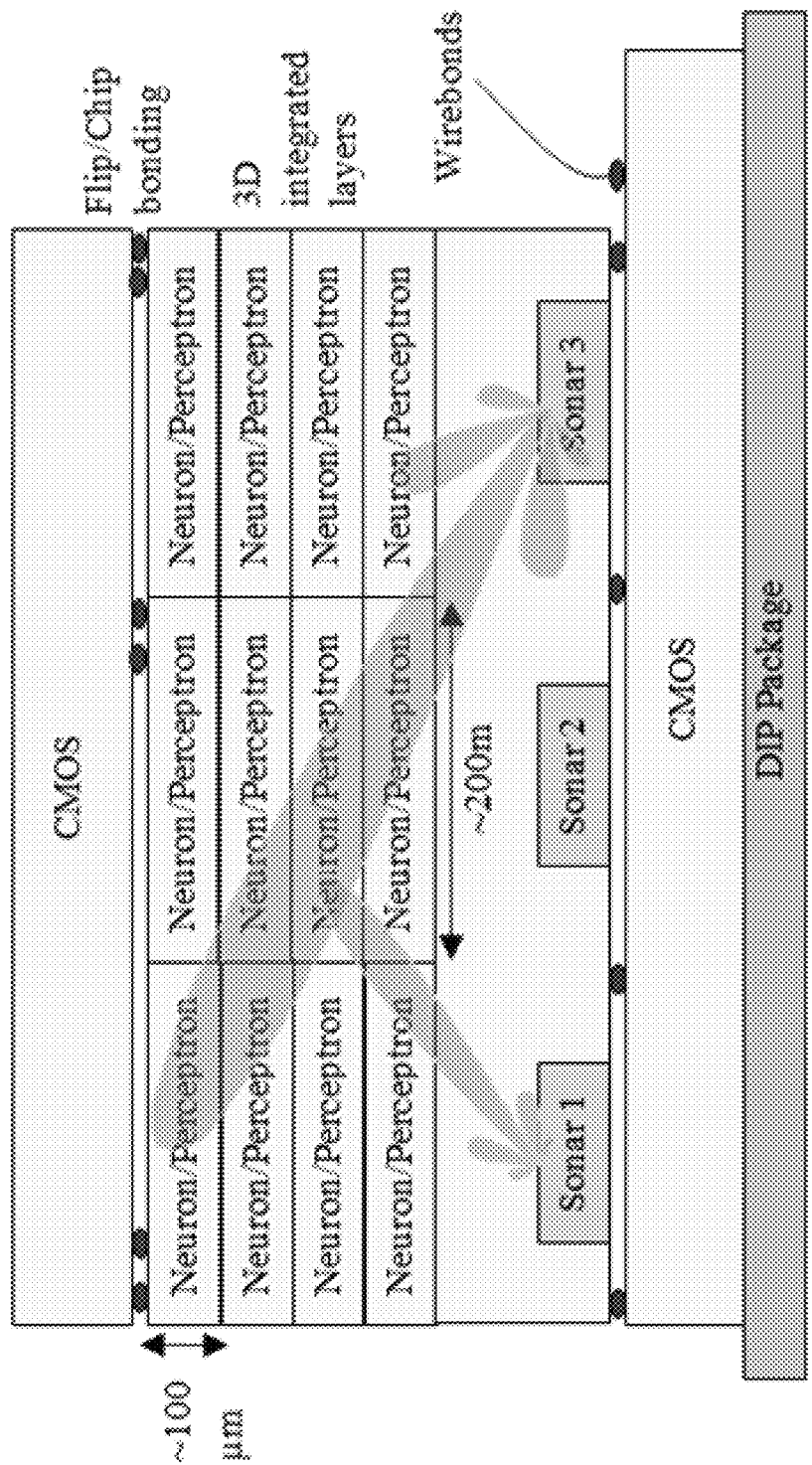
FIG. 21 shows a 3D architecture of integrated stacked neurons and a sonar array to communicate and transmit to each neuron.

FIG. 21 shows a 3D architecture of integrated stacked neurons and a SONAR array to communicate and transmit to each neuron. In the context of the network of basic capacitive building blocks shown in FIG. 14A, each neuron may include one or more of the basic capacitive building blocks 1402. The SONAR beams generated by the multiple SONARs can therefore be used to interrogate neurons. In order for an SONAR to write weights of a neuron, the SONAR can focus itself onto a computational neuron and send a series of pulses with amplitude modulation for each of the weights. Following a clock signal, each of the weight of the neuron can be programmed corresponding to the charge developed on a piezoelectric transducer at the neuron. This allows for fully programmable weight system with 3D architecture. The inputs to the neurons can be formed by different sonars tuned to different frequencies. Preliminary simulations show that with a carrier frequency of 400 MHz, with 5% bandwidth transducers, a data transmission bandwidth of 20 MBits/seconds can be achieved. Assuming 8-bit resolution weight writing, approximately 1000 weights can be updated every millisecond, a speed which is typical of computational neuron weight updating rates need to be updated for image processing implementation.

Figure 22:
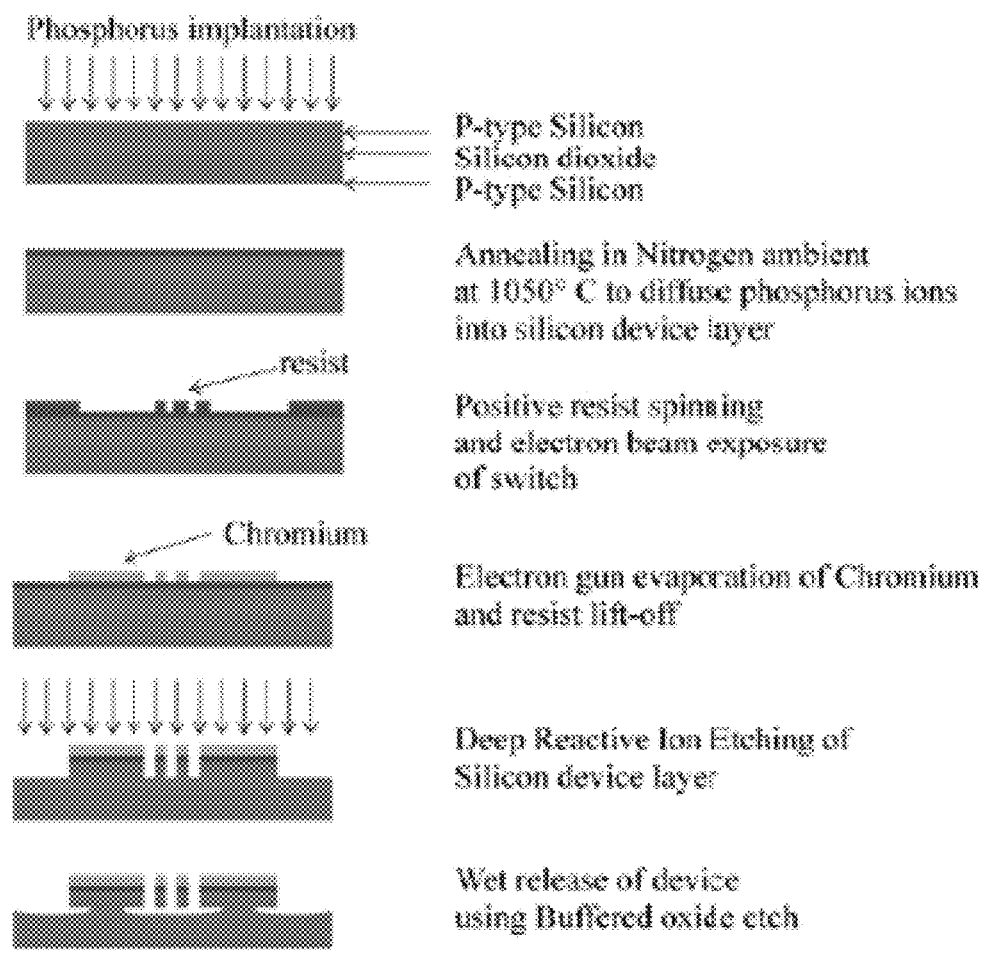
FIG. 22 illustrates a process flow for fabricating NEMS switches using silicon on insulator (SOI) wafers.

FIG. 22 illustrates a process flow for fabricating NEMS switches using silicon on insulator (SOI) wafers. The starting structure is an SOI wafer with structural device layer of thickness, e.g., 2 um. Photoresist is used to define a chromium masking layer. A deep reactive ion etch is then used to define the silicon structures. Next, vapor HF is used to etch away the silicon dioxide underneath to release the beam structures. This etch step is a time rate release etch process, i.e., the smaller structures will be released whereas the larger anchor structures will still be bonded to the substrate. In a particular embodiment, the gap between the capacitor plates as well as the thickness (and therefor compliance) of the multiplier is 300 nm which is limited by the deep UV lithography available for these devices.

Figure 23:
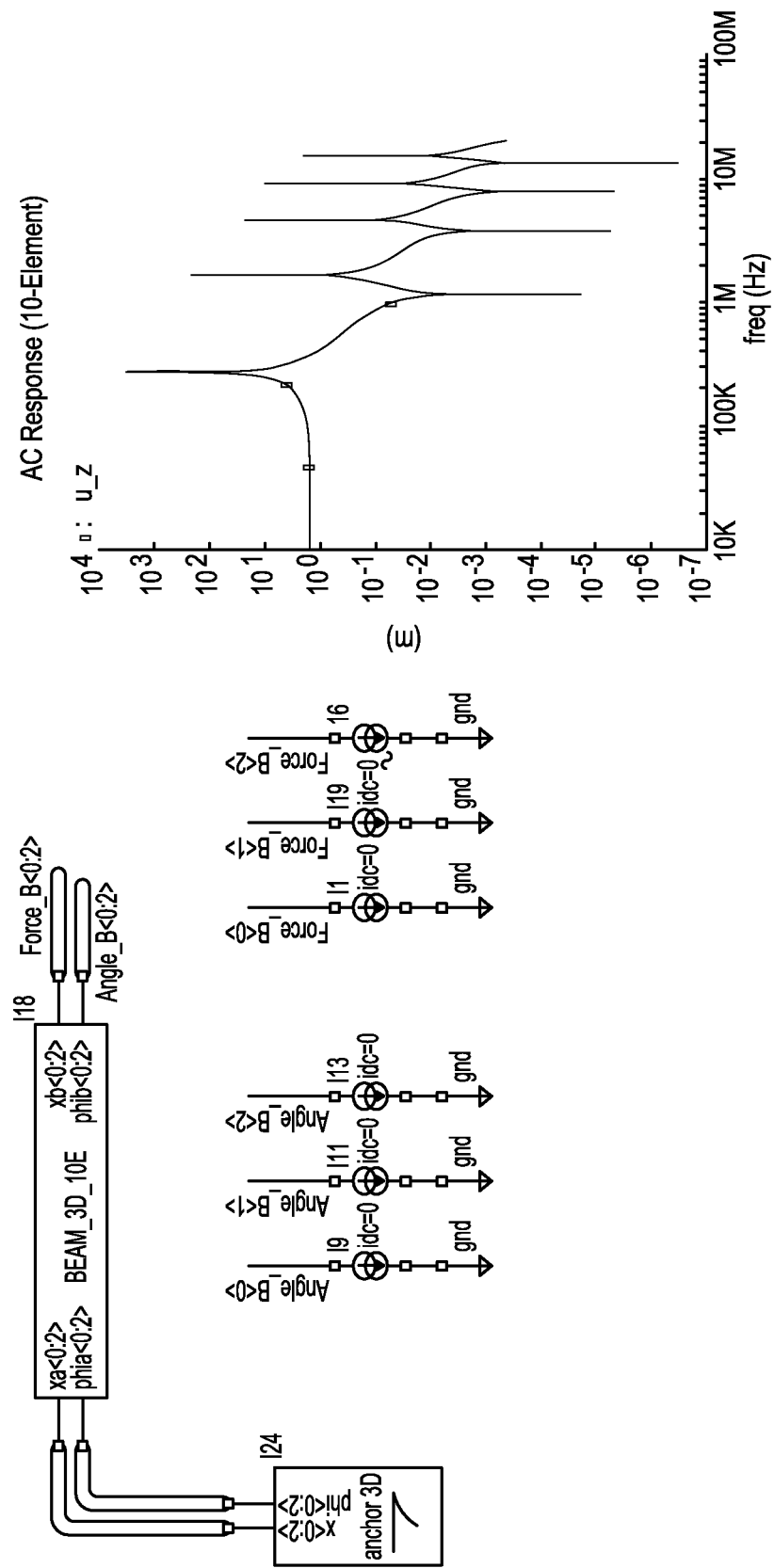
FIG. 23 shows SPICE based simulation of the NEMS devices for fast simulation of mechanical components and transistors within a single CAD framework

FIG. 23 shows SPICE based simulation of the NEMS devices for fast simulation of mechanical components and transistors within a single CAD framework. The plot on the right shows the simulated resonance spectra of a cantilever beam.

Exemplary NEMS Process Development:

Exemplary SOI based process flow to implement NEMS switches. This exemplary process can provide 50 nm gaps using e-beam and DUV lithography, e.g. with an exemplary design space of the spring constants, and the device variability can be measured to help in optimized bounded designs. This exemplary process can be modified such that the connections to beams can be made to a CMOS chip by flip chip bonding.

Exemplary NEMS Vector Product Design Space:

a multivariable optimization code can extract the equivalent SPICE models for the NEMS multipliers and adders, such that the models can be directly be interfaced to CADENCE CMOS layout tools. An exemplary model for NEMS switches can be adopted for an exemplary analog computation model.

Exemplary NEMS DAC Development— exemplary NEMS process flow and models. Different DAC designs based on NEMS conversion can be implemented to chart out the tradeoffs between power, bit resolution, and space per weight. CMOS circuits to implement the weight storage and connections to the DAC can be included in the MOSIS tapeouts. In the exemplary Phase I, 8 bits DAC resolution, which can be extended to 16 bits in the exemplary Phase II. Conversion from floating point numbers can be implemented to extend the dynamic range of the weights that can allow for more direct translation of the software inference engine.

Exemplary AlN Ultrasonic Sonar for High Fanout Development:

An exemplary process flow to integrate AlN pixel array and simple digital drivers for phased array but transmission in 3 dimensions. CMOS circuits can be implemented after characterizing AlN transducers for the equivalent circuit at the peak transduction frequency. The range, link budget as function of carrier frequency and power can be modeled and verified from 3D interconnects.

Exemplary Implementation of the Inference Engine in NEMS—

The exemplary NEMS chip can be interfaced to the CMOS circuitry to enable the direct hardware mapping of the inference engines. Sonic fanout and direct wired connectivity between nodes can be compared to see what will give higher degree of accuracy for output and learning. The learning algorithms can be implemented in the digital electronics section.

In some aspects, the disclosed technology includes nanoscale devices for ultralow power vector product computation and high fanout.

NEMS Nanoelectromechanical Synapses—

The quadratic relationship between the force and the applied voltage across nano-scale beams can be used to realize femtowatt multiplications between weights and input. In addition, nanomechanical transduction of the multiplication weights can be added in series in parallel with zero additional power. Capacitive addition and resistance addition can be used to achieve massively parallel addition. Nanoscale transduction can be provided by the piezoelectricity in graphene, an effect recently discovered as part of the disclosed technology. The disclosed technology can include parallelizing the multiplication and addition vector product in parallel at speeds in the gigahertz range, e.g., enabling real-time image processing applications. The weights can be stored in analog and digital states. The weights can be presented to the multipliers through analog CMOS and exemplary NEMS of the disclosed technology. The disclosed NEMS D to A converters can use new architectures to provide femtowatt DA converters. With the NEMS vector-product architecture, $10^7$ ops/ns μW can be achieved. The disclosed base technology includes nanomechanical switches as synaptic nonlinear switches which consume femotowatt DC power, and multi-gap electrostatic inputs enables multi-threshold actuation for high dynamic range of weights. The disclosed NEMS technology can be used in non-contact mode, sidestepping issue with the reliability of actual mechanical contacts, and relying only on nm-scale displacements of beams to modulate gaps and strains.

Sonar Interconnections—

The inference engine requires high fanout, to a sparse network of computational nodes. Furthermore, these fanout nodes need to be formed on the fly as the network evolves. In the disclosed technology, ultrasonic pulses in the GHz range can be used to form a programmable sonar interconnect system. The wavelengths of GHz sonic pulses can be the 5-10 um range enabling focusing sonic pulses from one channel to another in 3D using piezoelectric phased arrays with programmability and ability to write to thousands of inputs serially at kHz rates, e.g., rates needed for real time image processing. The SONAR elements can take information and transmit it to each 3D stacked NEMS neurons, which each has power going to them and maybe locally connected, allowing for weights to be changed across a much larger volume, and creating a very high fanout.

Integrated Circuits Based Devices for Volatile Compound Detection

Fast and reliable detection of toxic gas-phase industrial chemicals and warfare agents, which may be combustible, odorless, and colorless, necessitates the use of miniaturized multi-functional and portable gas analyzing systems. Disclosed are gas sensor devices, systems, and techniques for measuring ion-mobility and identifying chemical compounds in a gas-phase sample using a silicon micro-machined ion-mobility spectrometer array (IMSA), which is obtained from a versatile high aspect-ratio 3-D fabrication process. The multi-electrode architecture facilitates simultaneous detection of more than one gas species. Such a device has potential use for on-chip ion trapping in a quadrupole or hexapole electrode configuration. It also paves the way for a label-free gas analyzing system that can be monolithically integrated with on-chip low-noise amplifiers to produce a low-cost mobile platform for detection and analysis of multiple gas species.

Figure 24:
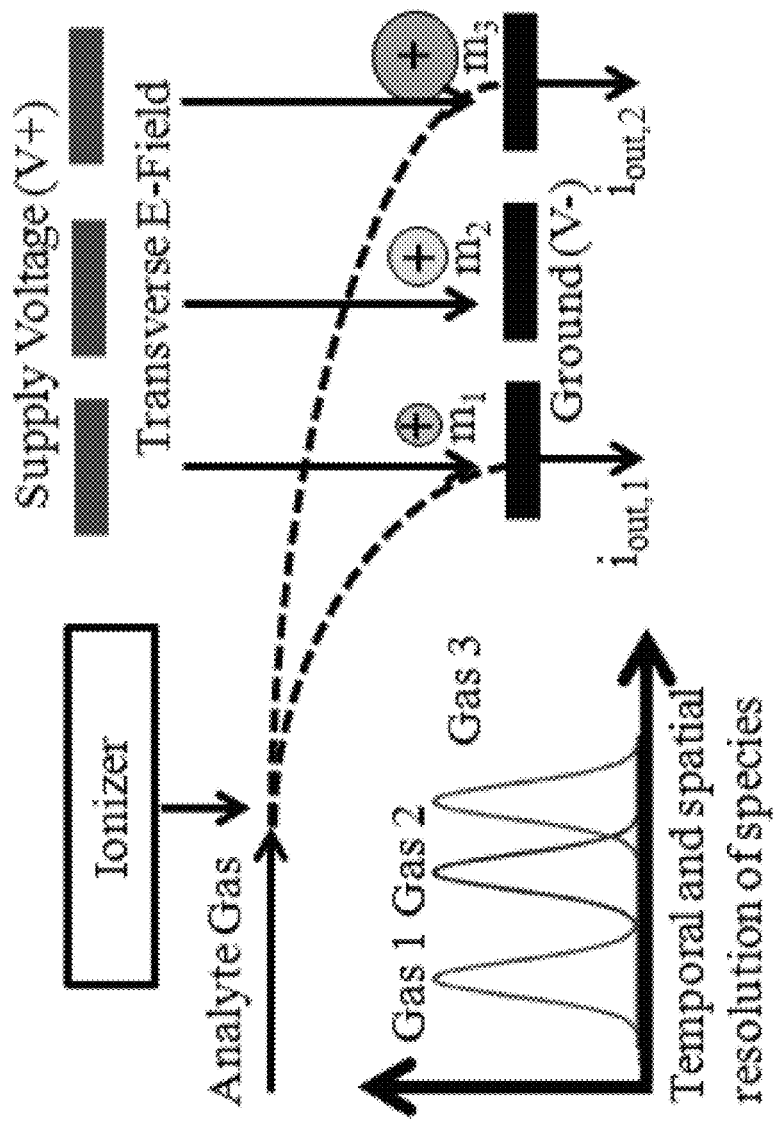
FIG. 24 shows an ion-mobility analysis concept.

FIG. 24 shows an ion-mobility analysis concept. The analyte gas mixture is ionized at the entrance of the flow channel. The ions have a constant lateral velocity and a transverse E-field is applied to this mixture. The ions undergo mobility-dependent segregation on the individual electrode islands which is detected as an output current—the electrode on which the ions are detected provides an estimate of the ion charge and mass. In order to operate an ion-mobility analyzer at low voltages (<5V), the separation between opposite arrays of electrodes be relatively small, for example at 1 mm. This allows generation of electric fields of 5-8 kV/m, sufficient to separate ions of different molecules on individual detector islands. In one implementation, with transverse electric fields of few kV and ion-motion with air as the buffer gas, the electrode width and inter-electrode spacing are designed so that distinct ionized gas species can be detected on different electrodes based on their mobility.

CMOS Ionization Source

In order to identify multiple species of volatile organic compounds (VOC) in charge neutral mixture of compounds in air on the basis of ion-mobility, the molecules need to be ionized. Electrons can ionize gas molecules effectively, and the generated ions have a specific time history of creation and recombination. Ion-formation processes are well-understood. The first ionization energies of gas-phase molecules are of the order of 1-100 eV based on electron-affinity of the molecules, molecular size which determines the tightness of the electron binding, steric hindrance properties etc. The creation of the ions occurs at the time scale of nanoseconds, while recombination can occur at time scale of microseconds to milliseconds. It is assumed that the time history of the charge cloud formation and annihilation will contain information to identify the gas species ionized.

Basis for Performance Targets (Calculations, Simulations, Data):

For the measurement of ion-motion, the ions need to be generated in air. Traditionally, this has been done with on-chip heating via tungsten wires which emit thermal electrons. However, such ion-generation is power hungry (1-100 mW) and can lead to device failure over time due to heating and corrosion. This problem can be overcome using electron-emitting radioactive $^{63}$Ni for ionization—from the Fermi theory of beta decay, the shape of the energy distribution for allowed transitions in $^{63}$Ni—$N(E)=C(E^2+2Em_ec^2)^{1/2}(Q-E)^2(E+m_ec^2)F(Z,E)$.

Figure 25:
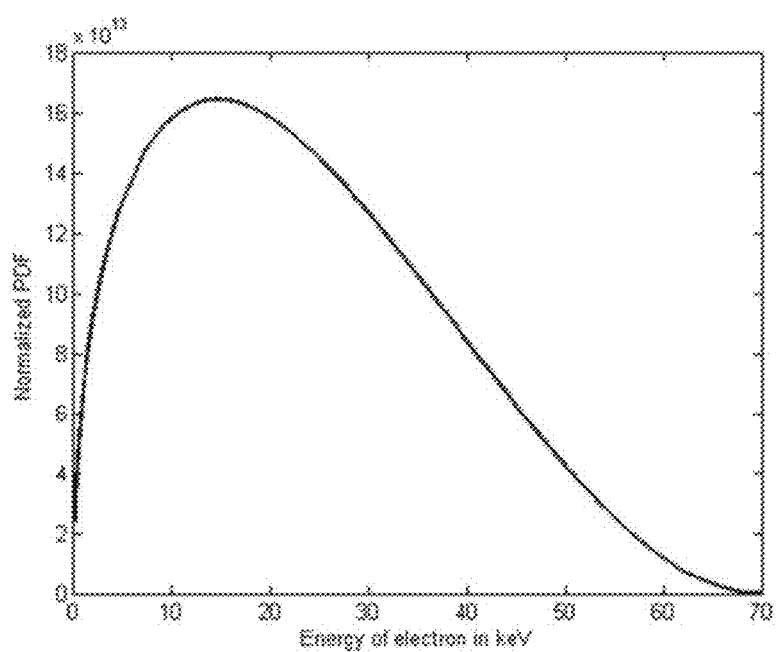
FIG. 25 shows the distribution of electron energy versus density profile for electrons emitted by $^{63}$Ni.
Figure 26:
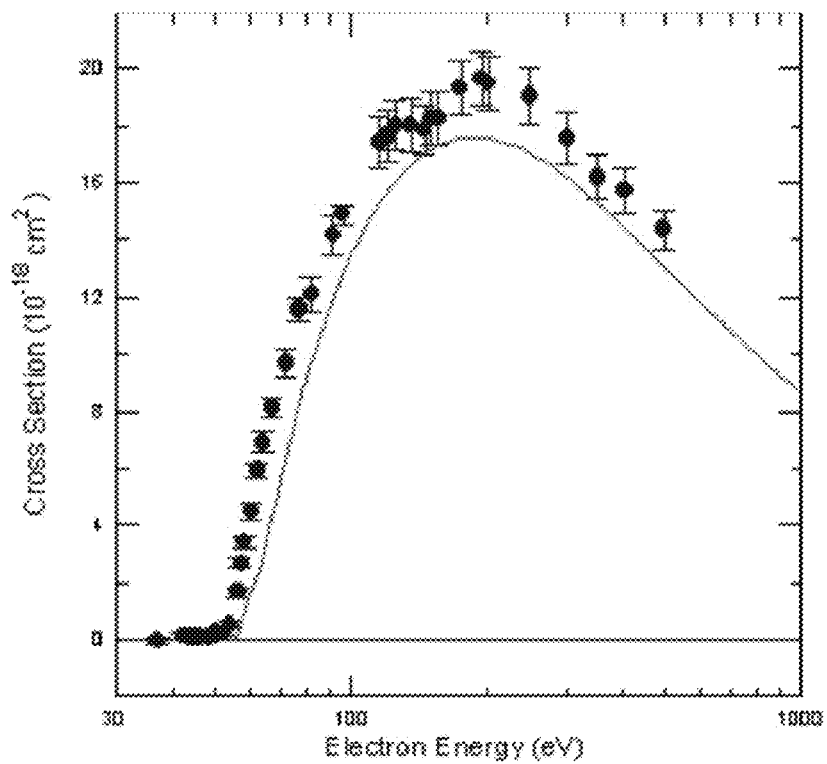
FIG. 26 shows primary energy dependence of the secondary electron yields curve.
Figure 27:
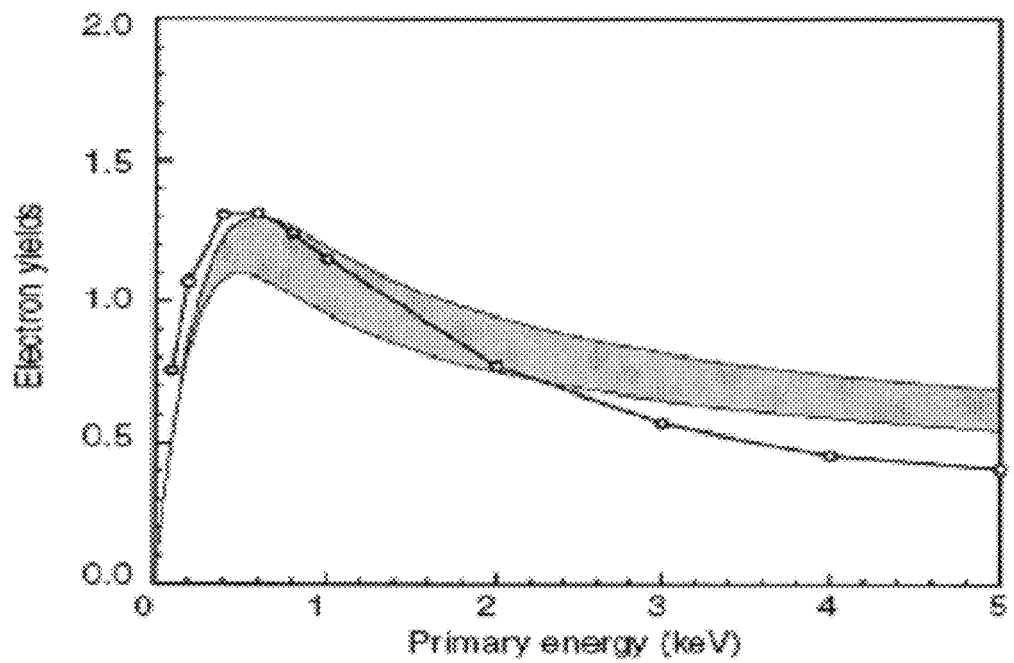
FIG. 27 shows energy dependence on the gas ionization cross section.

The Fermi function F is given by—

$$F(Z, E) = \frac{2\pi\left(\frac{Ze^2c}{\hbar}\right)\sqrt{\frac{m_e}{2E}}}{1 - e^{-2\pi\left(\frac{Ze^2c}{\hbar}\right)\sqrt{\frac{m_e}{2E}}}} \quad \hbar = \frac{6.63 \times 10^{-34}}{2\pi} J.s,$$

where N(E) is the number of electrons emitted at a certain energy E; $m_e$ is mass of an electron; c is the speed of light; Q is the maximum kinetic energy of the emitted electron; Z is nuclear charge on the daughter nucleus. $^{63}$Ni has an average emitted primary electron energy of 17.2 keV and a half-life of 100 years. This is effectively a zero input power source that does not require heating. The penetrating power of these electrons is also very low and can be easily stopped by thin film thicknesses in μm, making them suitable for commercial applications. Monte-Carlo simulations reveal primary electrons on collision with air molecules produce many more secondary electrons with energies up to 300 eV which then produce majority of the ionization. FIG. 25 shows the distribution of electron energy versus density profile for electrons emitted by $^{63}$Ni. FIG. 26 shows primary energy dependence of the secondary electron yields curve. FIG. 27 shows energy dependence on the gas ionization cross section.

A 1-millcurie film of $^{63}$Ni (1 cm×1 cm size) can produce a number of $3.7\times10^7$ primary electrons per second that hit a nanoelectrode surface with nano-gaps. The primary electron and cascade secondary electrons can create $7.4\times10^9$ ions per second in one centimeter square area, based on experimental data and the a cross-section data obtained from FIG. 25. Then it can be estimated that 0.2 ions per second will be generated per 50 nm×50 nm detection area.

Implementations:

$^{63}$Ni films of various activities from tens of uCi up to 1 mCi (1 cm×1 cm) are housed. A device is developed by the integration of electron-emitting radioactive $^{63}$Ni with CMOS-compatible devices, as well as low-cost microfabricated structures. Recently, we have used $^{63}$Ni for the realization of a self-powered ion gauge and ion pump which utilizes electrons emitted from the thin-film radioisotope to compute the pressure based on ionization current and for near-IR scintillation of xenon by radioisotope decay for wavelength calibration and analysis with Spencer's theory of electron penetration using xenon cross-sections derived from the Thomas-Fermi theory. Over the past decade, we have demonstrated the use of $^{63}$Ni for: self-reciprocating radioisotope-powered micromechanical resonators, harvesting mechanical stored energy in these resonators to generate electric power, energy harvesting with integrated betavoltaics, self-powered wireless transmission with, parallel electron lithography.

The specific technique for ionization plays an important role in the broad-band performance of the breath biosensors. Thermal ionization forms the basis of high sensitivity mass spectroscopy in which a purified and pre-concentrated sample is heated after desorption from the pre-concentration surface to produce ions. However, such ionization is power hungry due to the required heating element. Also, the degree of ionization depends on the components of the mixture and a static heating element with a preset heating mechanism may not be able to ionize all the components of the mixture. Photo-ionization with a broad-band light source is limited by the production of predominantly positively charged ions as photoelectrons are knocked out of the analyte mixture and only a small percentage of these are captured by neutral molecules to form negatively charged ions for mobility-based separation.

In contrast, ionization with a Ni-63 thin-film beta-decaying radioisotope provides the advantages of:

Broad-band electron emission with electron energies in the range of 0-67 keV with an average energy of 14.9 keV, which are sufficient to produce positive ions from multiple components of a mixture with various ionization potentials as well negative ions due to electron capture by molecules with strong electron affinities.

In addition to direct ionization of pre-concentrated VOCs, other ion-formation processes are also possible with complexes involving VOCs and one or several molecules of water for hydration. In air, high energy electrons from 63Ni may ionize nitrogen and low-energy thermalized electrons attach to oxygen. With large water vapor in the breath concentration, reactant ions H+(H2O)$_n$ and O2-(H2O)$_n$ are formed. For a particular VOC, the following compound reactions with water molecule displacement are possible, providing further data to analyze and identify the VOC.

VOC+H$^+$(H$_2$O)$_n$↔(VOC)(H$^+$(H$_2$O)$n_{-1}$)+H$_2$O

VOC+O2$^-$(H$_2$O)$_n$↔(VOC)(O2$^-$(H$_2$O)$n_{-1}$)+H$_2$O

The electrons can be easily shielded by thin layers of most materials and do not penetrate any cell layer of skin, making them safe for most applications as a biochemical sensor.

The stable electron decay with a half-life of 100 years and temperature and pressure invariant electron-emission ensures that these ionization sources are not affected by heating required for other components of the gas sensor are not the limiting factors in the operation lifetime of the disclosed sensors.

The thin-film radioisotope is a zero input-power ionizer without any heating elements and hence is ideal for the disclosed breath analyzer sensors.

The ionization of various concentration levels of VOC samples will be investigated using $^{63}$Ni thin films of various sizes. A key factor in minimizing the footprint of the disclosed device and take advantage of scaling is to identify the appropriate level of electron-emission required per second to ionize the VOC. Based on the limiting reagent, i.e. the VOC or the energy-distribution of electrons emitted from $^{63}$Ni, the right number of breath cycles can be chosen for pre-concentrating the VOC. This number can also be chosen based on the required sensitivity for the sensor so that enough samples are ionized to produce a detectable signal.

Gas Pumping Module

Following ionization of the VOCs with the zero-input power $^{63}$Ni, the ions are transferred to the ion mobility spectrometer for detection. In the disclosed system, a mechanical piezoelectric resonator is used for acoustically streaming and pumping the ionized VOCs and hydrated ion-complexes into the IMS for mobility-based sensing. Piezoelectric fans (piezofans) using bulk lead zirconate titanate (PZT) have been previously demonstrated as low-power-consumption and low-noise devices for the dissipation of accumulated heat in confined regions for macro-scale devices with applications in portable electronics such as cell phones and laptops.

Basis for Performance Targets (Calculations, Simulations, Data):

The disclosed piezofan is a PZT plate attached to a Si-cantilever beam or just a fixed-free PZT bimorph beam with electrodes patterned on it for contact. When an AC voltage is applied across the electrodes at the resonance frequency of the structure, the electric field induces mechanical strain in the beam, producing micro-motion of the tip. The structure stiffness may be given by $$-k = \frac{3YI}{L^3},$$

wherein Y is the effective Young's modulus of the structure, L is the length of the suspended beam and I is the moment of inertia about the fixed point expressed in terms of the width 'W' and thickness 'T' of the beam, given by $$-I = \frac{WH^3}{12}$$

The resonance frequency of such a beam is given by $$-f = \frac{1}{2\pi}\sqrt{\frac{k}{m}}.$$

The oscillation of this beam to generate air flow by means of acoustic streaming has been well-studied and theoretical results have been verified in conjunction with experiments. In some implementations, the designed cantilevers with thin film PZTs have resonance frequencies varying between 300 Hz and 500 Hz. Acoustic streaming models for such structures are well-known. Disclosed is the use of such piezofans at their resonant frequencies as well as at higher modes to investigate the flow of ionized molecules into the device. Enhanced gas mixing to produce a more homogenous mixture prior to injection into the IMS is possible with higher resonance modes at the cost of higher power, as seen with macroscale fans before.

Figure 28:
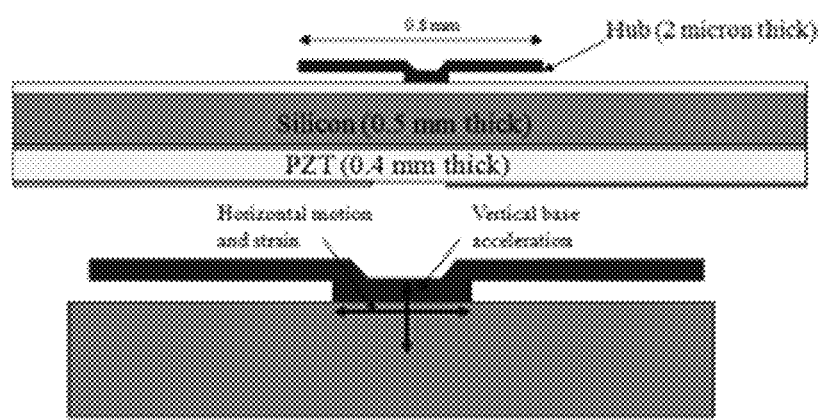
FIG. 28 shows a schematic of a surface micromachined hub for producing acoustic streaming with actuation at fundamental and 4th mode.
Figure 29:
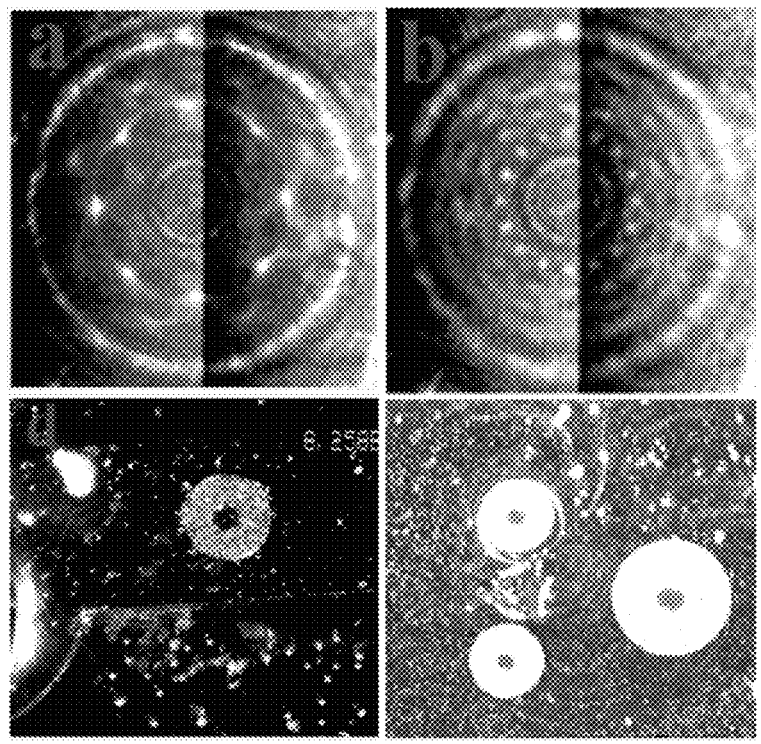
FIG. 29 shows interferometer measurement of flexural mode vibrations of hub (subplots a and b) and vortex generation & particle concentration channels (subplots c and d).
Figure 30:
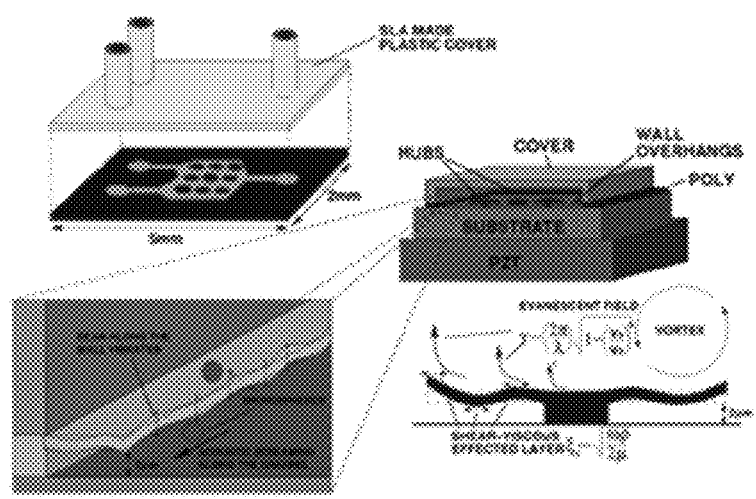
FIG. 30 shows addressable vortex generation and particle concentration using the flexural mode vibration hubs.
Figure 31:
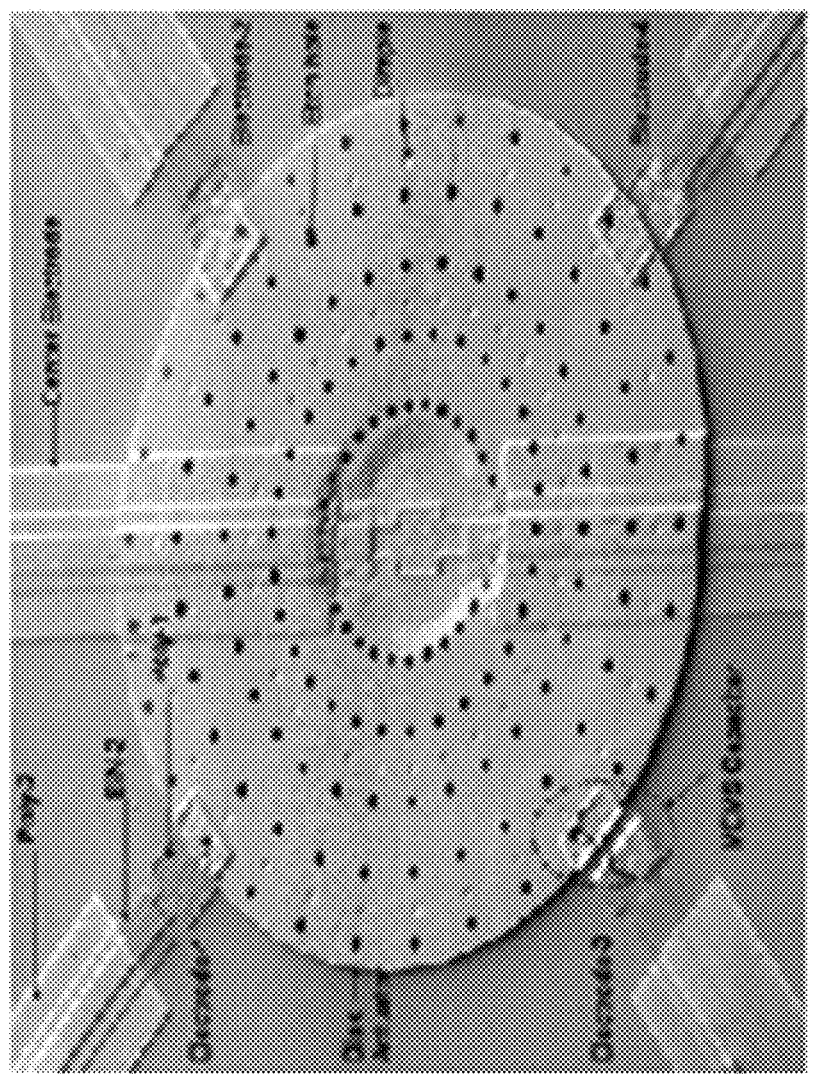
FIG. 31 shows an all-electronic cytometery with integrated co-axial pickup for electronic and sonic cell separation.

Implementations:

Surface micromachined hubs are developed for flexure mode excitation to produce acoustic streaming. FIG. 28 shows a schematic of a surface micromachined hub for producing acoustic streaming with actuation at fundamental and 4th mode. In a particular implementation, the base of the hub is vertically accelerated to cause horizontal strain and buckling in the device. FIG. 29 shows interferometer measurement of flexural mode vibrations of hub (subplots a and b) and vortex generation & particle concentration channels (subplots c and d). More specifically, these plots show interferometrically obtained vibration modes at 2.17 MHz and 6 MHz with as low as 2.5 V$_{pp}$ drive for the PZT and addressable vortex generation and particle concentration using these flexural mode vibration hubs for streaming in micro-fluidic channels illustrated in FIG. 30. FIG. 31 shows an all-electronic cytometery with integrated co-axial pickup for electronic and sonic cell separation. We have performed all electronic cytometery using these devices with integrated coaxial pickup for effective sonic and electrostatic separation of cells and signal pickup at precise locations on the hub shown in FIG. 31. It is desirable to leverage the disclosed gas pumping technology and the disclosed novel thin-film PZT growth and patterning to build and test piezofans for ion-pumping with acoustic streaming. It is also possible to used bulk PZT to study the effects of ultrasonic actuation on micro-mechanical devices such as membrane-based resonators, silicon micro-machined micromotors, neural probes and recently for in-plane actuators.

Piezofans are promising as gas pump due to their low electromagnetic noise as well as minimum space requirement. The effects of tip structure, gap, and amplitude of the piezoelectric fan have been studied. Significantly scaled-down miniature thin-film microfabricated PZT fans can be used for modulating the air flow fairly precisely.

The disclosed gas pumping module can regulate the ion-flow accurately with precise micro-motion of resonant cantilever fans. The prototypes have been developed using a novel thin-film deposition process for PZT and air-bridges for metallization contacts to actuate the fan electrodes. In the disclosed sensor, an optimal design for a ion flow regulator that can simultaneously minimize the power consumption, actuation voltage and positioning to transfer ions to the IMS device need to be investigated. With basic COMSOL simulations, various resonance frequencies of the fabricated devices of different lengths and widths for a fixed PZT thickness can be determined and a mode can be chosen that provides maximum homogeneity of the ionized mixture as well as dynamic range in flow rates over the IMS device, based on tip micro-motion. The modes of the resonator can be confirmed experimentally using an impedance analyzer to determine the frequencies for lowest motional impedance and interferometric vibrometer measurements with frequency scanning. In addition, the resonant frequency can be fine-tuned by atomic layer deposition (ALD) of platinum electrodes as well as focused ion beam (FIB) etching precisely as a fabrication process. Typical power consumptions for bulk-PZT-based piezofans are between 1-100 mW. However, for thin-film PZT piezofans <1 mW consumption is expected.

Some advantages of the disclosed technology include: (1) reduced form factor to match the CMOS scaling of breath sensing devices in the IMS; and (2) electromechanical coupling factors of microfabricated single crystal structures are usually higher than bulk devices, making the former easier to benefit from a larger dynamic range actuated modes with lower actuation voltages.

Also disclosed in this disclosure are molecular sensor devices, systems, and techniques for measuring ion-mobility to detect gases in ultra-portable packages capable of integration with mobile communication devices. The disclosed sensors includes a piezoelectric micro fan that is low power, low voltage, and sufficiently small to provide air molecule samples at rates determined by convection. In other aspects, the disclosed sensor devices include semiconductor integrated circuits having integrated in-chip acoustic communication links and nodes for use in fingerprint scanners.

In some aspects, the disclosed molecular sensor devices includes a chip-scale gas sensor using a low-voltage thin-film piezoelectric sense-actuate fan pair.

In one aspect, an ion-gas sensor device includes a substrate including an array of pillars and troughs, a microfan component including a first stack and a second stack of layers of a piezoelectric composite material formed on the pillars of the substrate and protruding over the troughs, the first stack of layers to sense the flow of ions in a gas and the second stack of layers actuate to drive the ions to a detection region of the device at a controlled flow rate, a layer of a radioactive material formed in the trough of the substrate to ionize the gas when the gas is flowed above the layer, and an array of electrode formed in the detection region to detect ion mobility of the ions of the gas.

Microscale ion-mobility measurement is an approach to sensing gases in ultra-portable packages such as the burgeoning hand-held smart-phone markets. A key component of a gas sensor is the ability to sample the air molecules at rates determined by convection rather than diffusion for faster detection time. The disclosed technology includes devices having a piezoelectric micro fan, including a micro-fan architecture that is low power (e.g., 10.6 mW/sccm), low voltage (e.g., 8.5 V/sccm), and sufficiently small (0.1 mm³/sccm). In some implementations, for example, the devices can include a multi-electrode configuration of ion-detection with less than 5V operating voltage. Exemplary implementations of the disclosed technology described herein demonstrate a pathway towards a chip-scale ion-mobility based gas detector with a process compatible with the ion-detection system, and the actuate and sense micro-fan architecture presented here.

Figure 32:
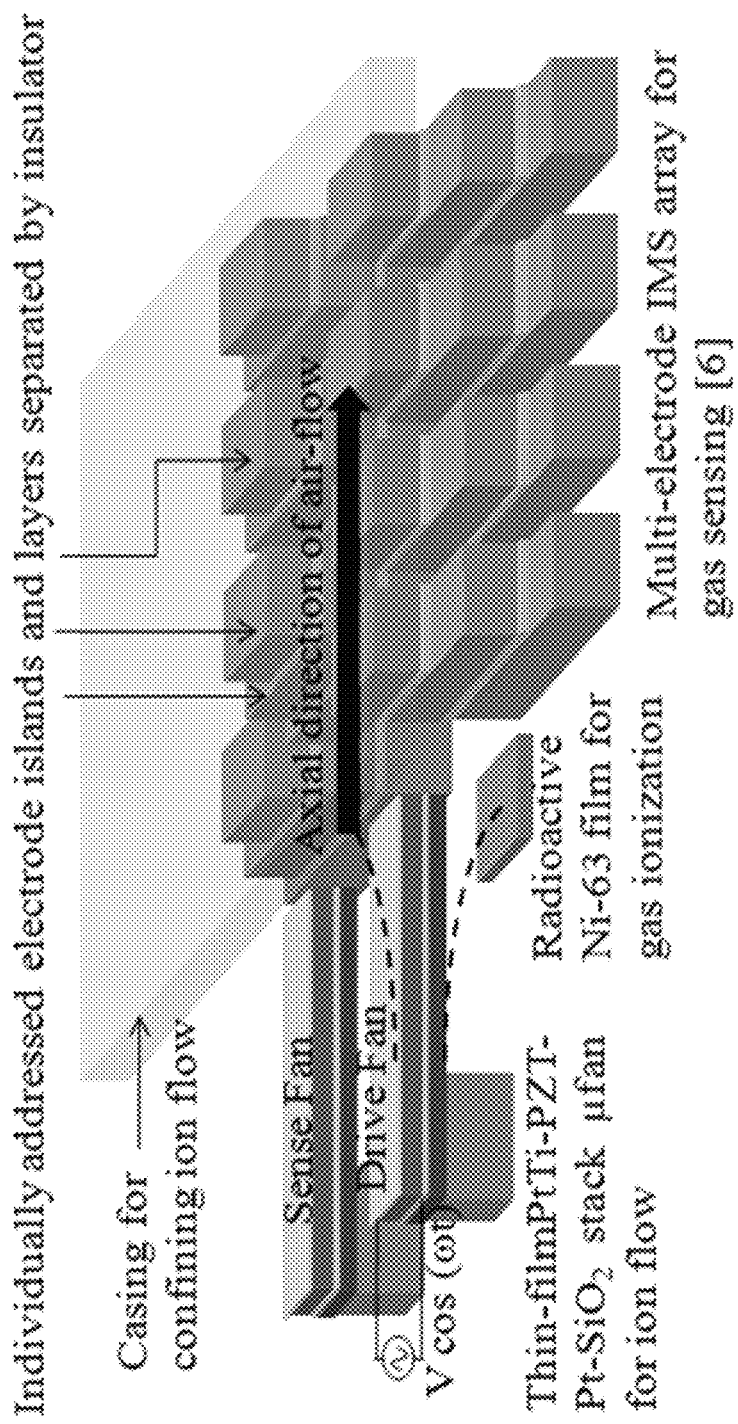
FIG. 32 shows a diagram of an exemplary chip scale ion-gas sensor of the disclosed technology.

FIG. 32 shows a diagram of an exemplary chip scale ion-gas sensor of the disclosed technology. More specifically, the ion-gas sensor comprises an IMS array gas sensor, radioactive Ni-63 film for gas ionization, and piezoelectric microfans for producing ion-flow and integrated with the IMS array gas sensor.

In ion-mobility gas sensors, one desires high ion flow velocity without turbulence, to maximize the sampled air volume for a given sampling time. To prevent turbulence in micro-channels, inertial fluid forces should be weaker than viscous forces. For a Reynolds number ~10, a flow velocity of ~2 m/s can be tolerated for a 100 µm diameter micro-channel. These velocities can be achieved by actuators driving air directly, but typically require high voltages. Alternatively, secondary flow due to nonlinear effects such as acoustic streaming can result in high motion even with low motion in small channels due to high gradients of acoustic and ultrasonic fields. In order to achieve the high velocities, micro-scale fans and pumps have been explored for use in micro-gas analyzers, mass-specs, ion-mobility-based sensors as well as cooling via convective airflow and gas accumulation. For example, micro-valve-based multi-stage micropumps can be useful in producing large flow rates and pressure differentials for on-chip gas flow. In some examples, electrostatically actuated torsional micro-fans can also been used. These devices, however, require high-voltage operation (e.g., ~100 V) not compatible with portable and low-power platforms. Rotary fans have scratch-drive actuators and <30$V_{p-p}$ resonant operation, but are prone to frictional wearing inherent in their principle of operation.

Figure 33:
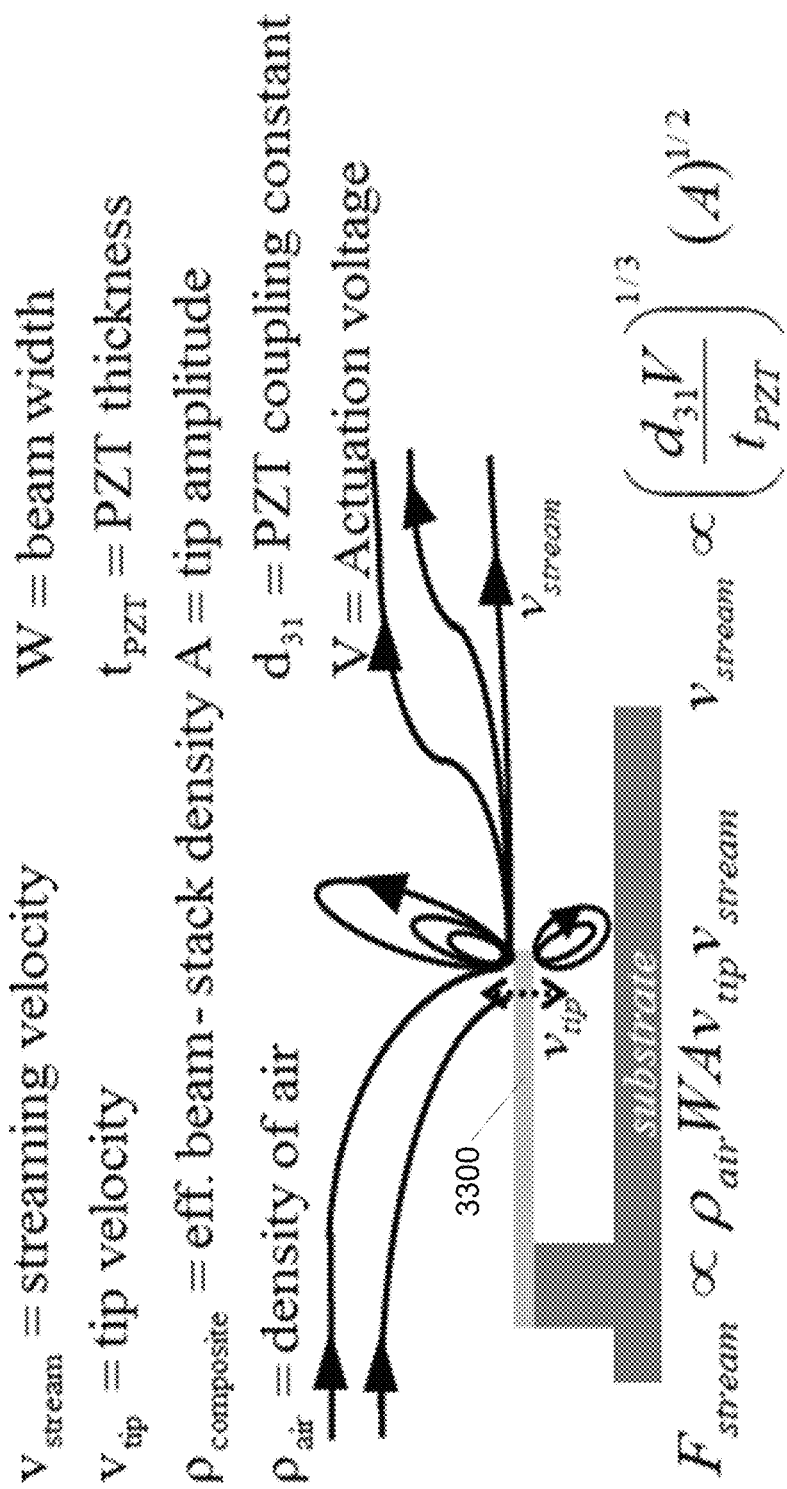
FIG. 33 illustrates a micro-fan comprising a thin-film stack including a piezoelectric layer.

The disclosed devices include a micro-fan design that uses a thin-film $SiO_2$—TiPt—PZT-Pt stack as a composite unimorph actuated at resonance. For example, FIG. 33 illustrates a micro-fan 3300 comprising a thin-film stack including a piezoelectric layer. The micro-fan peak-to-peak displacement, magnified at resonance, produces air flow along its axis by shedding air vortices close to its tip, as well as re-circulating loops above surface of the micro-fan. The produced air flow is a function of Reynolds number, tip-substrate gap, and etch-holes on the surface of the micro-fan. The ability to produce controllably large microscale air-flow is an attractive feature for chip-scale gas-sensing.

Figure 34:
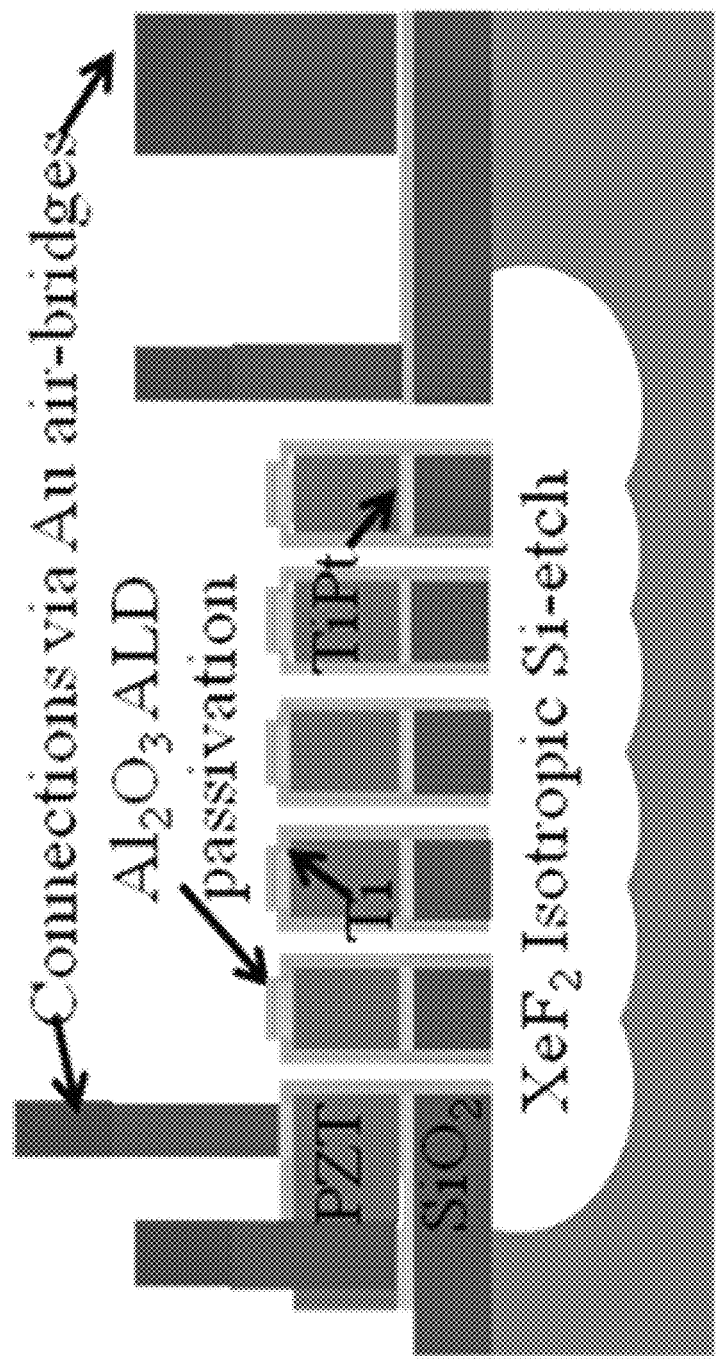
FIG. 34 shows a cross-sectional view of an exemplary device including a micro-fan structure formed by a $SiO_2$—TiPt—PZT—Pt stack.

FIG. 34 shows a cross-sectional view of an exemplary device including a micro-fan structure formed by a $SiO_2$—TiPt—PZT-Pt stack, wherein the micro-fan is anchored on the substrate at one end and suspended over a gap above the substrate at the other end.

Figure 35:
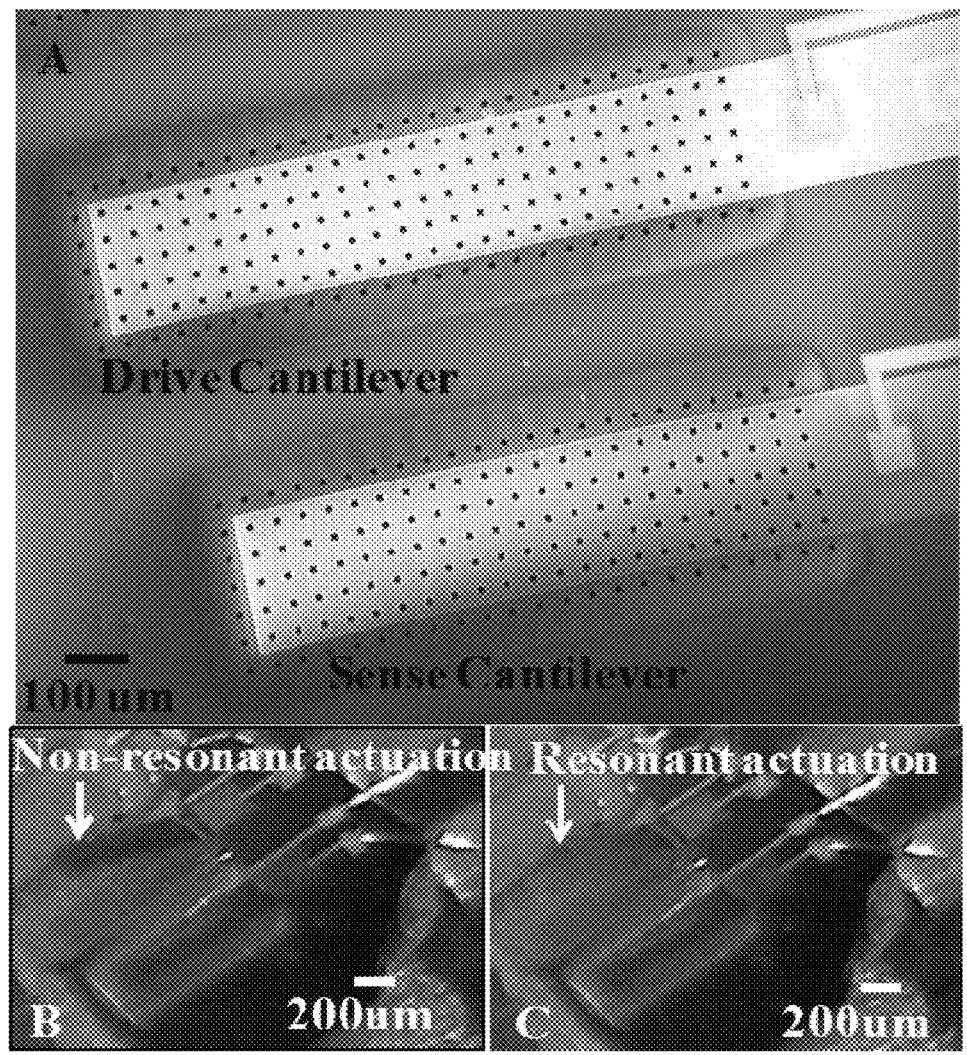
FIG. 35 shows images of a fabricated micro-fan structure on a substrate.

FIG. 35 shows images of a fabricated micro-fan structure on a substrate, wherein the micro-fan structure includes a actuate-sense fan pair (subplot A), wherein the micro-fan can be in non-resonant actuation (subplot B) and in resonant actuation (subplot C).

Exemplary implementations of the exemplary devices were performed. The exemplary actuate-sense fan pairs with widths of 200 µm and lengths 800 µm and 1000 µm, respectively, were tested in micro-channels. Multilayer analysis for arbitrary piezoelectric-elastic layer stacks, and exemplary measured data from DC actuation from 0-6V, yielded piezoelectric coupling coefficient $d_{31}$=−85.8±5 pC/N for the PZT films, less than values for bulk PZT but within expectation for multi-layer stressed thin-film devices. Resonance frequencies were measured to be at 614 Hz and 505 Hz, with peak-to-peak tip-displacement >200 um 2-Vpp, with 2.5 mW power input. A RTD element was used to measure air-velocity close to the tip of the fan.

Figure 36:
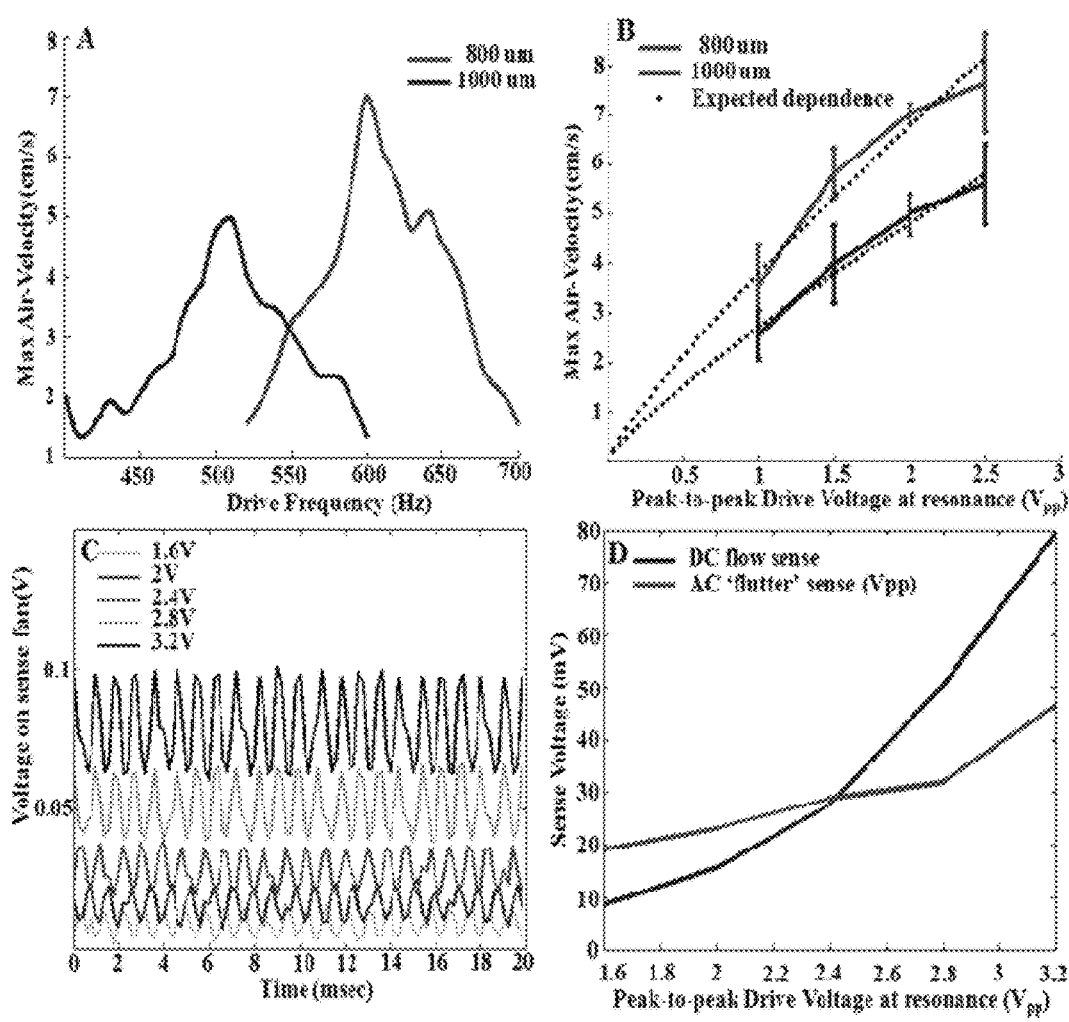
FIG. 36 shows the plots of measured air-velocity as a function of frequency and as a function of voltage at resonant-drive.

FIG. 36 shows the plots of measured air-velocity as a function of frequency and as a function of voltage at resonant-drive. More specifically, subplot A in FIG. 36 shows Max flow-velocity at the tip of the micro-fan as a function of drive frequency, and subplot B in FIG. 36 show Max flow-velocity at the tip of the micro-fan as a function of peak-to-peak drive voltage at resonance. Table 2 shows that using the micro-fan design of FIG. 33, a Max flow-voltage of 7 cm/sec is achieved for a maximum flow rate of 235.6 uL/min.

TABLE 2 compares the exemplary device with previous conventional designs.

| Work | Max Flow (μL/min) | Nominal Voltage | Power (mW) |
| --- | --- | --- | --- |
| Conventional Micropump | 4000 | 100 V | ~57 |
| Conventional Electrostatic Microfan | 10 | 100 $V_{p-p}$ | — |
| Exemplary Piezofan of Disclosed Tech | 235.6 | 2 $V_{p-p}$ | 2.5 |

Moreover, the sense-fan signal is measured (subplot C and subplot D in FIG. 36) to provide an integrated feedback element for the flow sensor. The larger random-motion signal from the flow indicates that a critical flow, the sense fan becomes unstable and starts to flutter, allowing the monitoring of the Reynolds number.

A Monolithic Ultrasonic Fingerprint Scanner

In some aspects, the disclosed technology includes a monolithic ultrasonic fingerprint scanner integrated on a CMOS die.

As personal portable electronics such as cell-phones and laptops become ubiquitous along with multiple digital identities one uses in cyberspace, the need for biometric identification has expanded well beyond the traditional areas of law enforcement or control of cleared access. In addition, the trends in the personalization of the services offered by companies and government, the demand in the security of the associated data generated by daily activities, and recent regulations on border security constitute firm signs that, the importance of biometric identification systems will continue to increase.

While biometric identification systems can use one or more types of any characteristic patterns in face, iris, or DNA, fingerprint imaging is one of the most common techniques due to its relatively optimal standing in terms of cost of equipment, time of identification (e.g., throughput), difficulty in falsifying results, ease of application to the subject, and operator-free (e.g., automatic) operation. The simplicity and relatively good performance of pen and ink method have made this approach the traditional standard to build the law enforcement databases used in criminal practice. This method, however, is gradually being replaced by more convenient and sophisticated devices utilizing optical, capacitive, and ultrasonic techniques that yield digitized data directly and minimize use of consumables and operation cost.

Figure 37:
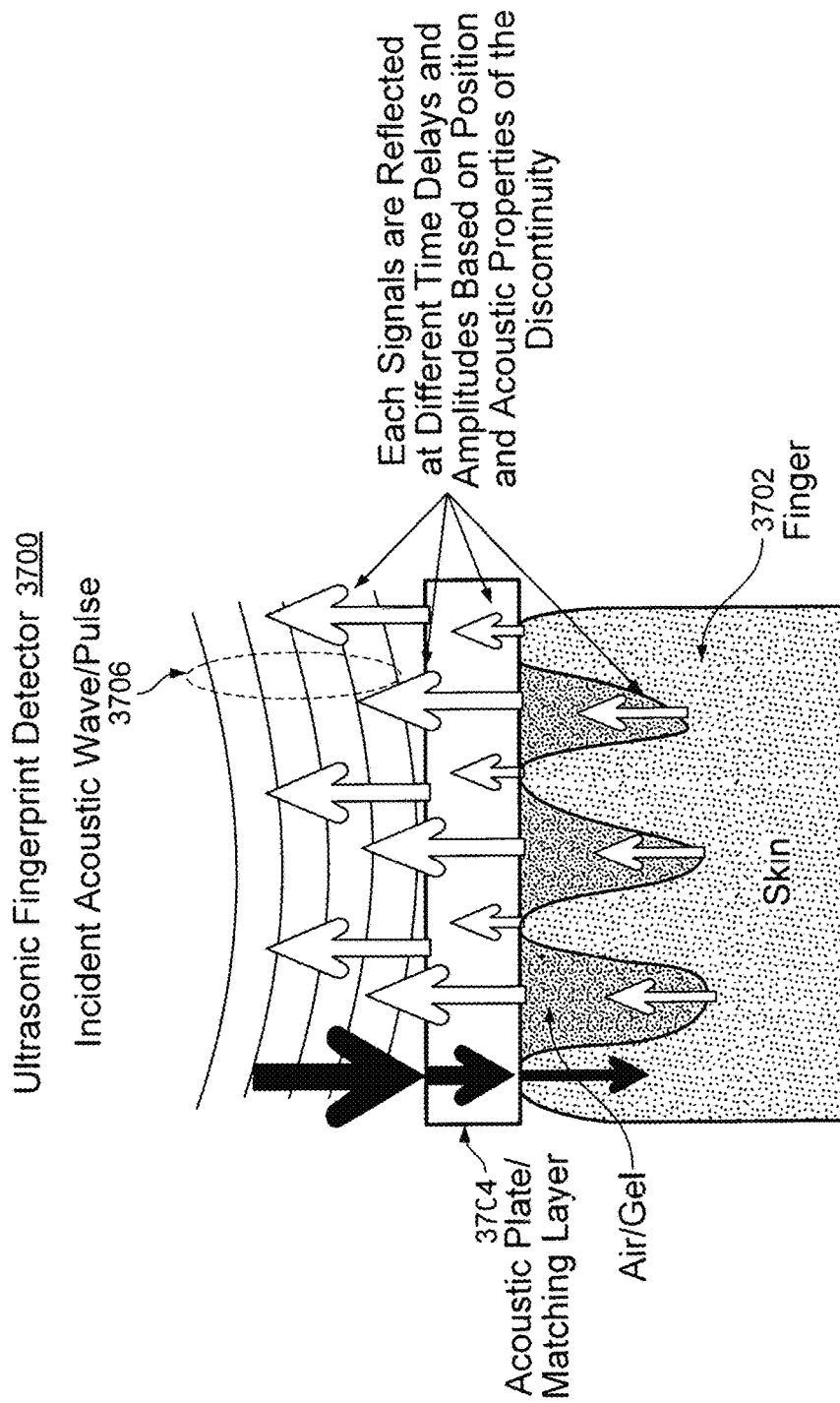
FIG. 37 illustrates the concept of ultrasonic fingerprint imaging based on pulse-echo principal.

Ultrasonic fingerprint imaging, which is the working principle of the disclosed device, uses an initial acoustic pulse and records the magnitude and time delay of the reflected acoustic waves from discontinuities along its path. FIG. 37 illustrates the concept of ultrasonic fingerprint imaging based on pulse-echo principal. As can be seen in FIG. 37, a finger 3702 makes contact with a ultrasonic fingerprint detector 3700, for example, by touching an acoustic plate or matching layer 3704 of ultrasonic fingerprint detector 3700. An incident acoustic wave 3706 traveling in a downward direction within the ultrasonic fingerprint detector 3700 is reflected off valleys and hills of the skin on finger 3702 at different times with different amplitudes to create echo singles. The arrows of different weight represent echoes of the incident ultrasonic wave (e.g., shown by black arrow) that are reflected at different depths and times across the cross-section of the skin. A 2D recording of echoes yields high resolution images of the skin, which can be used for identification of ridges of the fingerprint. Identification of ridges of the fingerprint from the echoes can be based on the frequency of the emitted acoustic waves and the characteristics of the specific transducers implemented in ultrasonic fingerprint detector 3700, which is described in detail below.

Some exemplary advantages of the ultrasonic imaging as compared to optical and/or capacitive approaches include: (1) improved image quality, especially in case of very dry or oily fingers or in humid conditions; (2) higher performance in the presence of contaminants such as grease, ink, as sound waves can penetrate through those; (3) possibility for 3D imaging as well as temporal imaging to distinguish blood flows within the tissues, thereby enabling a higher security against detached fingers or finger skins for breaching security.

Biometric identification products can be implemented based on the above-described ultrasonic fingerprint imaging principle. Unlike the conventional method of using bulk-piezoelectric ceramics and connecting these to drive and sense electronics using hybrid packaging approaches, the exemplary devices of the disclosed technology include a monolithic approach that relies on deposition of a thin-film piezoelectric film, e.g., AlN or PZT, as ultrasonic transducers on a CMOS die. This technology can be used to realize on-chip ultrasonic communication links based on beam forming principles to achieve configurability as shown in FIG. 38.

Figure 38:
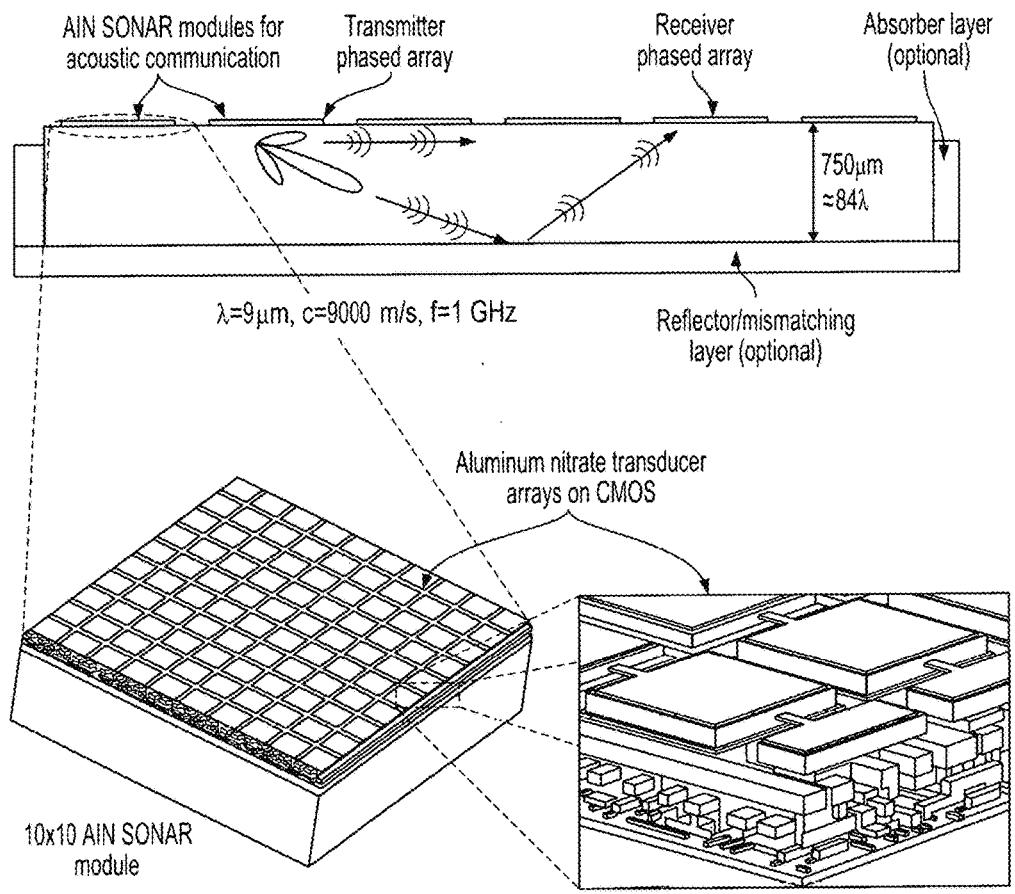
FIG. 38 illustrates aluminum nitride (AlN) transducer arrays built on top of a metallization layer, wherein the AlN transducer arrays can be configured as an ultrasonic fingerprint scanner.
Figure 38:
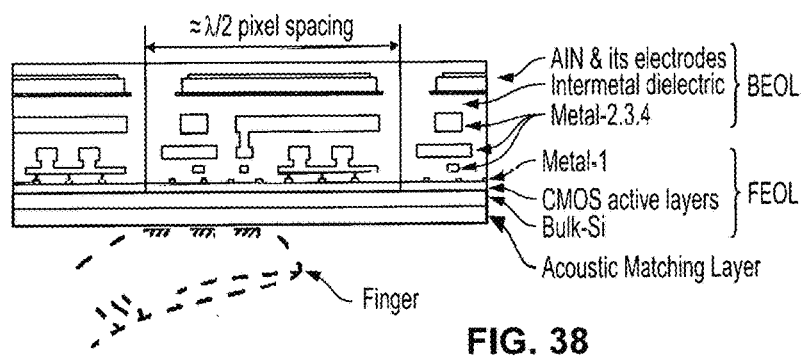

FIG. 38 illustrates aluminum nitride (AlN) transducer arrays built on top of a metallization layer, wherein the AlN transducer arrays can be configured as an ultrasonic fingerprint scanner. These arrays will be distributed on top of the chip as acoustic transmitter modules, which can communicate with each other by sending proper phasing of SONAR pulses at desired angles. The transmitted pulses can be reflected off the device boundary and be directed onto an desired destination SONAR element. Alternatively, Surface Acoustic Waves (SAW) can be used to communicate laterally.

Figure 39:
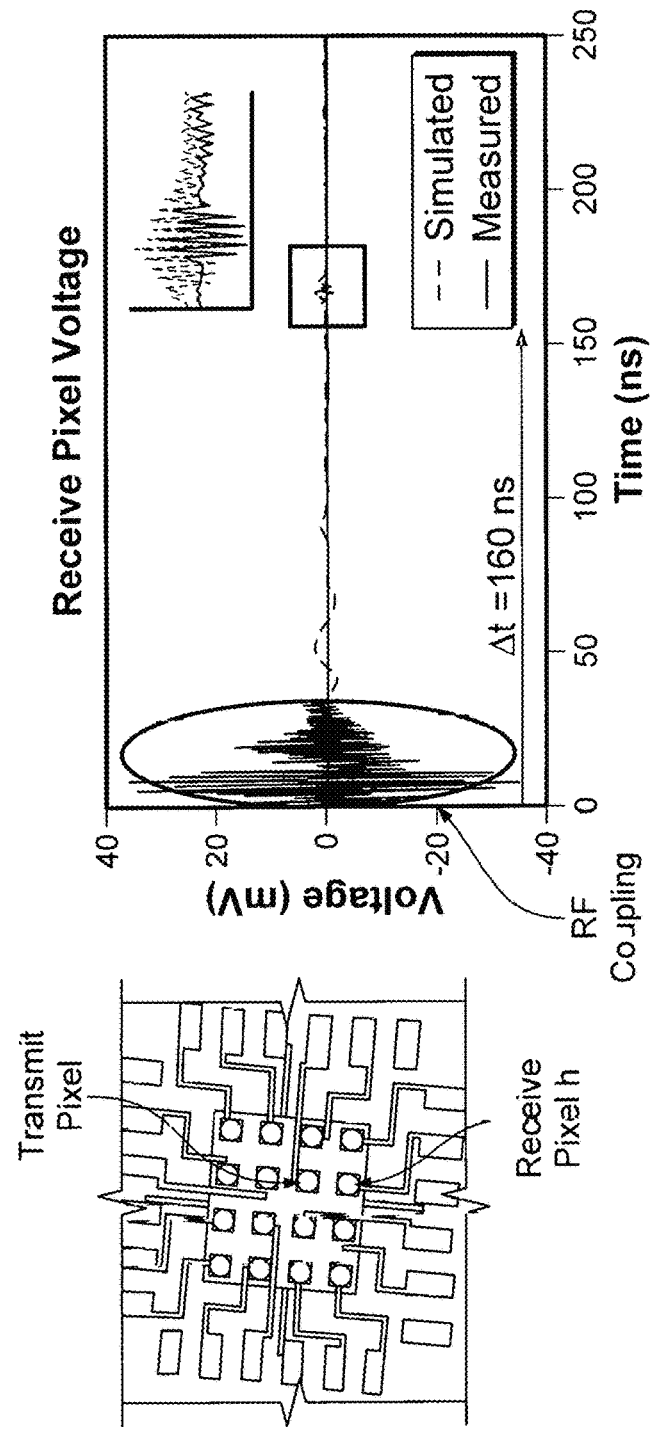
FIG. 39 shows an array of AlN transducers coupled to a silicon wafer are tested by sending an acoustic pulse from an first pixel through silicon and picking up on an neighboring pixel.

FIG. 39 shows an array of AlN transducers coupled to a silicon wafer are tested by sending an acoustic pulse from an first pixel through silicon and picking up on an neighboring pixel. During testing, one AlN transducer is actuated by a pulsed set of several cycles of a sine wave at 900 megahertz and transmits the pulses, and one receiving AlN transducer receives these pulses which are amplified by an on-chip CMOS RF amplifier of 10 dB gain.

Figure 40:
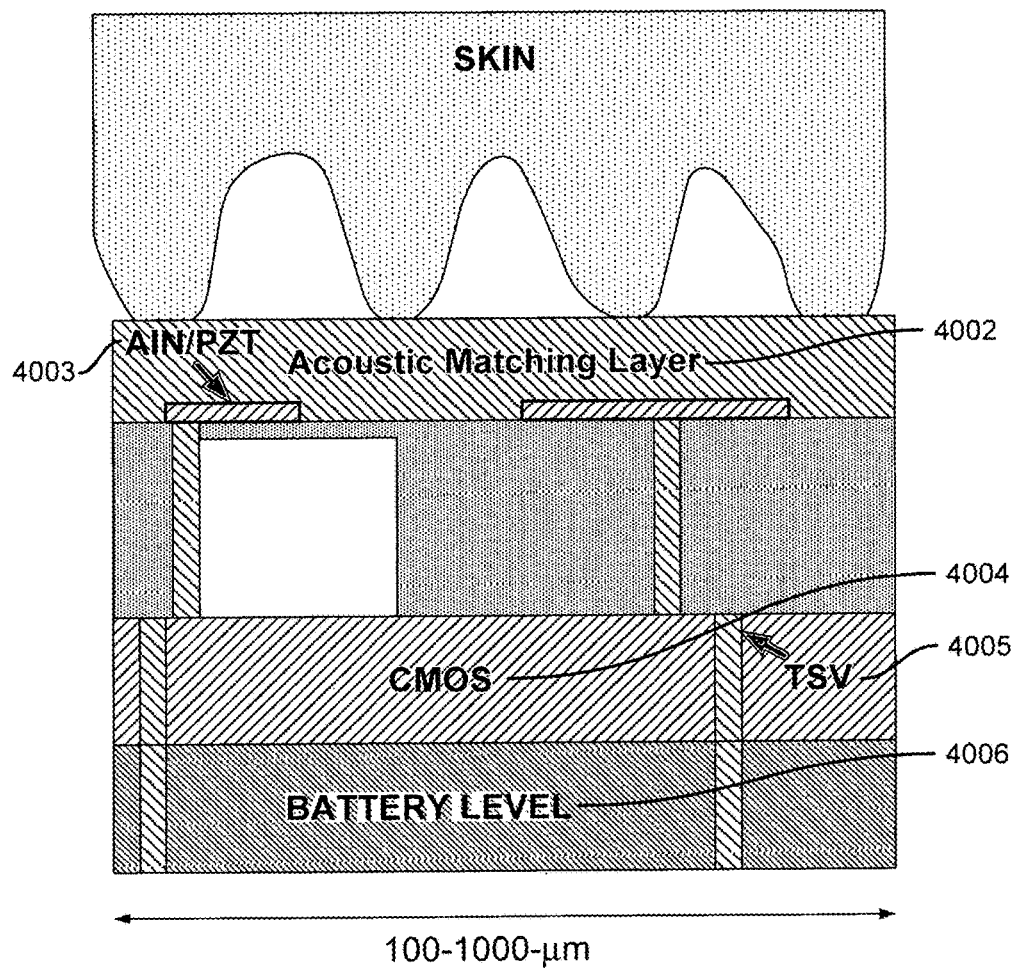
FIG. 40 shows a cross-section of the proposed monolithic ultrasonic fingerprint imaging unit.

FIG. 40 shows a cross-section of the proposed monolithic ultrasonic fingerprint imaging unit 4000. As can be seen in FIG. 40, an additional acoustic matching layer 4002 is included in the device. Focal Plane Arrays (FPA) of thin film AlN/PZT transducer pixels 4003 integrated on a CMOS die 4004, and coupled to through-Silicon via (TSV) 4005, are used as drive and readout electronics which are configured to perform pulse-echo imaging of the tissue with high resolution and improved size, weight and power merits than competing hybrid approaches. Furthermore, on chip membranes with piezoelectric films can be used for vibration energy harvesting or single trigger energy storage for one-time recording of the fingerprint image. SU8 based nano-composite can be used to fine tune the acoustic impedance of the matching layer so as to optimize the image quality. Included battery layer 4006 at the bottom of the CMOS die 4004 can be either a thin film or can be replaced by an external off-the-shelf battery to enable self-powering. Piezoelectric films on membranes or compliant structures can be used for energy harvesting each time a pressure is applied on the die for imaging or it can be designed to harvest energy from ambient vibrations by proper inertial loading.

Figure 41:
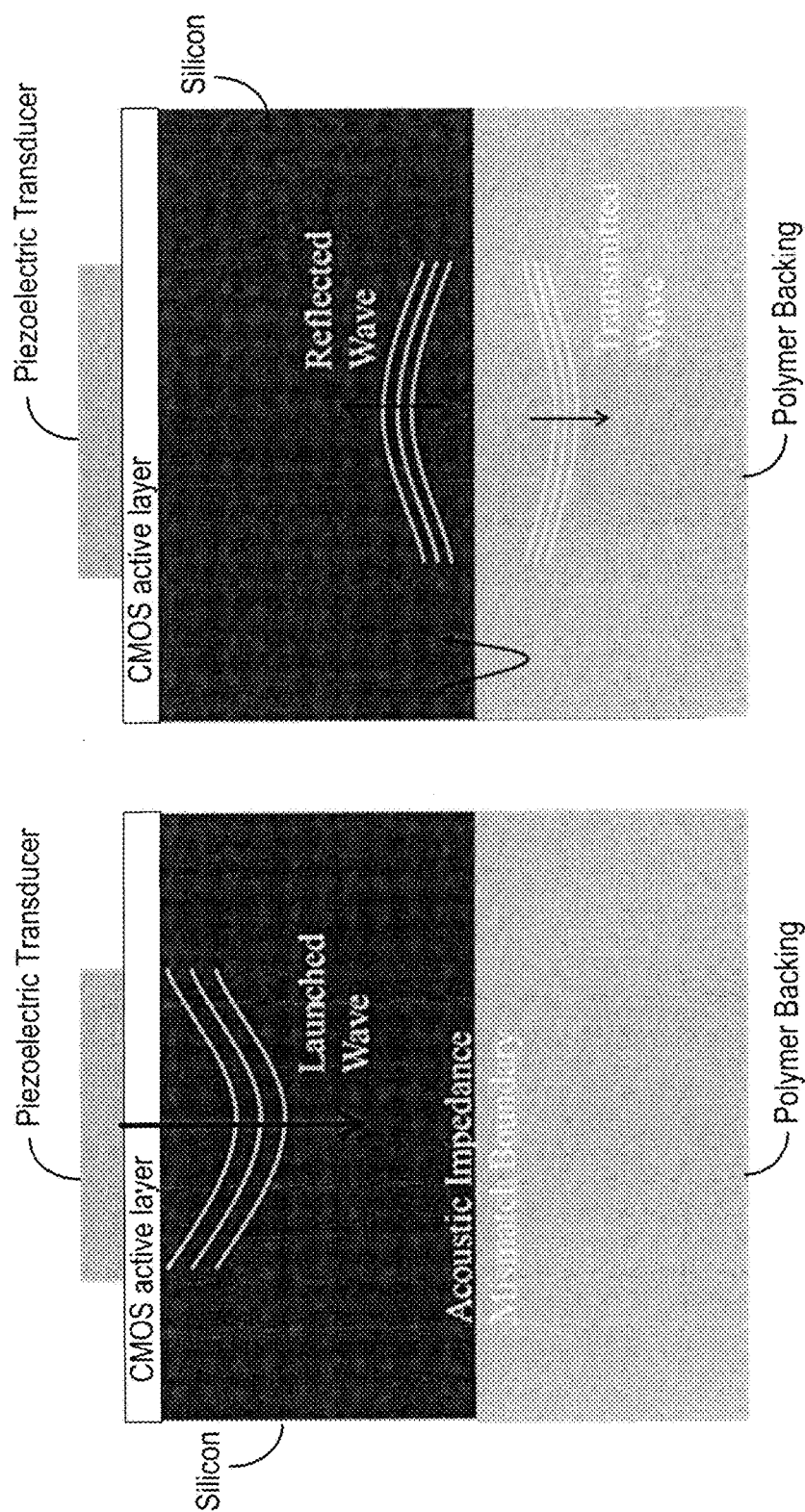
FIG. 41 shows the piezoelectric transducer launches ultrasonic pulse into silicon so that the reflected wave power can be used to determine properties of an object in the vicinity of the back side.

Thin film piezoelectric transducers have long been studied in the area of RF MEMS for their high Quality Factor and Piezoelectric coupling co-efficient ($k_t^2$). Much work has been done in this area to create CMOS compatible processes for RF resonators and filters. For example, we demonstrated the use of one of these process to utilize the Silicon wafer itself as a medium to transport mechanical ultrasonic waves As ultrasound is a wave phenomenon, there are many properties which are directly analogous to transmission line and electromagnetic wave theory, including acoustic impedance. All materials have an acoustic impedance determined by their mechanical properties, in particular density ($\rho_m$) and elastic stiffness (c) ($Z_0 = \sqrt{\rho_m c}$). This acoustic impedance determines the relationship between the stress component and the particle velocity component of the wave. As with electromagnetics, a boundary between two mediums with different impedances will reflect some of a waves energy and allow some to pass through, depending on the relationship between the two impedances ($\Gamma = (Z_2 - Z_1)/(Z_2 + Z_1)$). This reflection coefficient will be utilized to determine the properties of whatever may be present on the back side of the silicon wafer. FIG. 41 shows the piezoelectric transducer launches ultrasonic pulse into silicon so that the reflected wave power can be used to determine properties of an object in the vicinity of the back side.

Using silicon as the substrate, a piezoelectric thin film such as Aluminum Nitride can be fabricated on the top surface of a CMOS die, with the drive and sense electronics needed for interrogation integrated with the transducer. This transducer can be pulsed so as to excite an ultrasonic wave into the silicon which will reflect off of the back surface. Depending on the material attached to the back side of the silicon, different levels of power will return to the transducer. These can be quantified to distinguish between the presence or absence of a finger or even distinguish between a set of materials. For instance, as seen in Table 3, silicon itself has an acoustic impedance of almost 20 MRayls (106 kg/m2 sec), whereas air has an impedance of about 400 Rayls (kg/m2 sec) in this case the reflection coefficient is almost 1 and nearly all the energy in the wave is reflected back toward the transducer. However if something like Teflon (Z0=3 MRayls) were on the back then the reflection coefficient would be 73% and the signal returning would be measurable lower than the air backed case. Additionally human tissue is closely matched to water and on the order of 1.5 to 3 MRayls which would be measurable.

TABLE 3

Values of Acoustic Impedance of common materials
[Ref: Ristic "Principles of Acoustic Devices"
1983 John Wiley & Sons, Inc.]

| Material | Acoustic Impedance ($\times 10^6$) kg/m$^2$ sec) |
|---|---|
| Silicon | 19.7 |
| Glycerine | 2.5 |
| Teflon | 3 |

TABLE 3-continued

Values of Acoustic Impedance of common materials
[Ref: Ristic "Principles of Acoustic Devices"
1983 John Wiley & Sons, Inc.]

| Material | Acoustic Impedance ($\times 10^6$) kg/m$^2$ sec) |
|---|---|
| Polyethlyne | 1.75 |
| Polystyrene | 2.47 |
| Epoxy resin | 2.7-3.6 |
| Nylon | 2.4-3.1 |
| Silicone | 1.04 |
| Water | 1.5 |
| Air | 411E-6 |

TABLE 4

Signal levels and noise for various backing conditions

| Boundary Condition | Signal Measured (µV) | Signal Variance (µV) |
|---|---|---|
| Air Backed | 655.27 | 28.59 |
| Polymer Backed (gelatinous) | 503.00 | 29.28 |
| Polymer Backed (solid) | 343.73 | 28.68 |

Experimentally this phenomenon has been demonstrated, as seen in FIG. 42. More specifically, FIG. 42 shows experimental measurements of different silicon backing conditions. In the embodiments of FIG. 42, two transducers are utilized: one to transmit a pulse and a neighboring one to receive it. Subplot (a) is test board setup showing ultrasonic transducers locations and the connection to pulsing and measurement electronics. Subplots (b) and (c) show the back side of the silicon chip with and without a layer of polymer placed directly underneath the transducer. and annotating the location where the transducers are located. Subplots (b) and (c) show the backside of the silicon with and without a layer of polymer placed directly underneath the transducers. More specifically, subplot (b) does present an air backed condition while subplot (c) shows a polymer attached to the back side. Subplots (d-f) are the pulse measured after reflection from the backside. More specifically, subplot (d) is air backed, (e) is polymer backed when in gelatinous phase, (f) is polymer backed once it has completely solidified.

Note that the signal is the greatest in subplot (d) when there is nothing on the backside. The signal is reduced when the polymer is attached to the back as in subplot (e). This first measurement is made when the polymer is placed on the back in a gelatinous form as in (c). As the polymer solidifies its material properties change, and therefore it presents a higher acoustic impedance and a lower reflected signal in subplot (f) when the polymer solidified. In one embodiment, the polymer used is PVDF, having an acoustic impedance (1.5-3 MRayls) on the same order as human tissue (1.5-2 MRayls), operating as a suitable phantom for modelling the presence of a finger underneath the silicon. Similarly, the oils in the skin which leave a fingerprint behind could be detected as they also have a greater acoustic impedance than air.

An important aspect to this is the acoustic impedance presented by the polymer and whether or not its thickness matters. Crystalline materials have very low acoustic losses, silicon for instance, when operated at 3 GHz, has loss on the order of 1e-4 dB/wavelength. Polymers on the other hand exhibit 15-750 dB/wavelength of loss at 3 Ghz. The speed of sound in polymers is on the order of 1000-2000 m/s, at 1 Ghz this corresponds to a wavelength of 300-700 nm.

Another technique of detection involves measuring changes in the quality factor of an acoustic resonator. Thin disk transducers, that is transducers which are much smaller than their area, have resonances associated with their thickness. The transducer by itself has a resonant mode when the thickness of the ultrasonic wave is integer multiples of the half-wavelength. If a lossy material is placed on either side of the resonator, the resonator will lose energy to that material and lower its quality factor.

Figure 43:
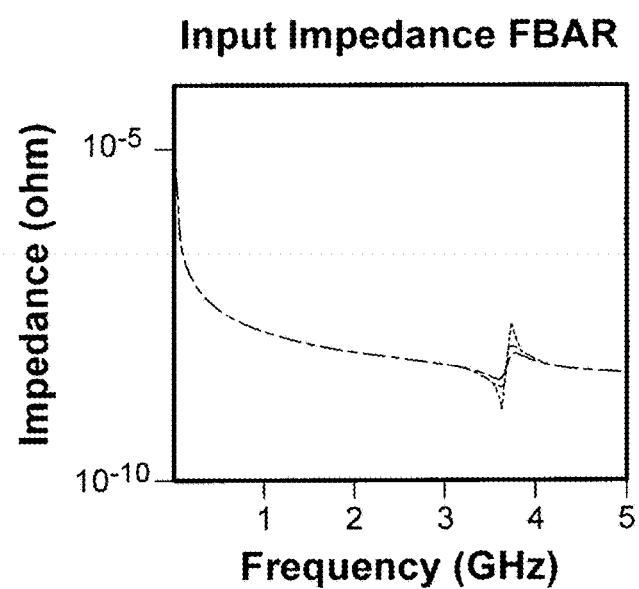
FIG. 43 shows a change in the acoustic impedance of the polymer resulting in a drop in the quality factor.

In the case of a thin film bulk acoustic resonator (FBAR), the proposed process can be altered so that the transducer is released from the substrate to create the resonator. In this case the polymer can be placed on the top side of the FBAR which presents a different acoustic boundary condition for the FBAR. If we model a 1 μm AlN FBAR with varying loads, FIG. 43 shows a change in the acoustic impedance of the polymer resulting in a drop in the quality factor. Here the maximum quality factor is limited by the AlN's intrinsic quality factor of about 90. Changes in these quality factors are determined with computer models.

TABLE 4

Summary of Simulated Quality factors of FBAR and HBAR resonators with polymer backing

| Condition | Q (FBAR) | Q (HBAR) |
|---|---|---|
| Air Load ($Z_0$ = 400) | 85.7 | 514.3 |
| Polymer Load ($Z_0$ = 1e6) | 25.0 | 157.0 |
| Polymer Load ($Z_0$ = 2e6) | 10.8 | 68.6 |

Figure 44:
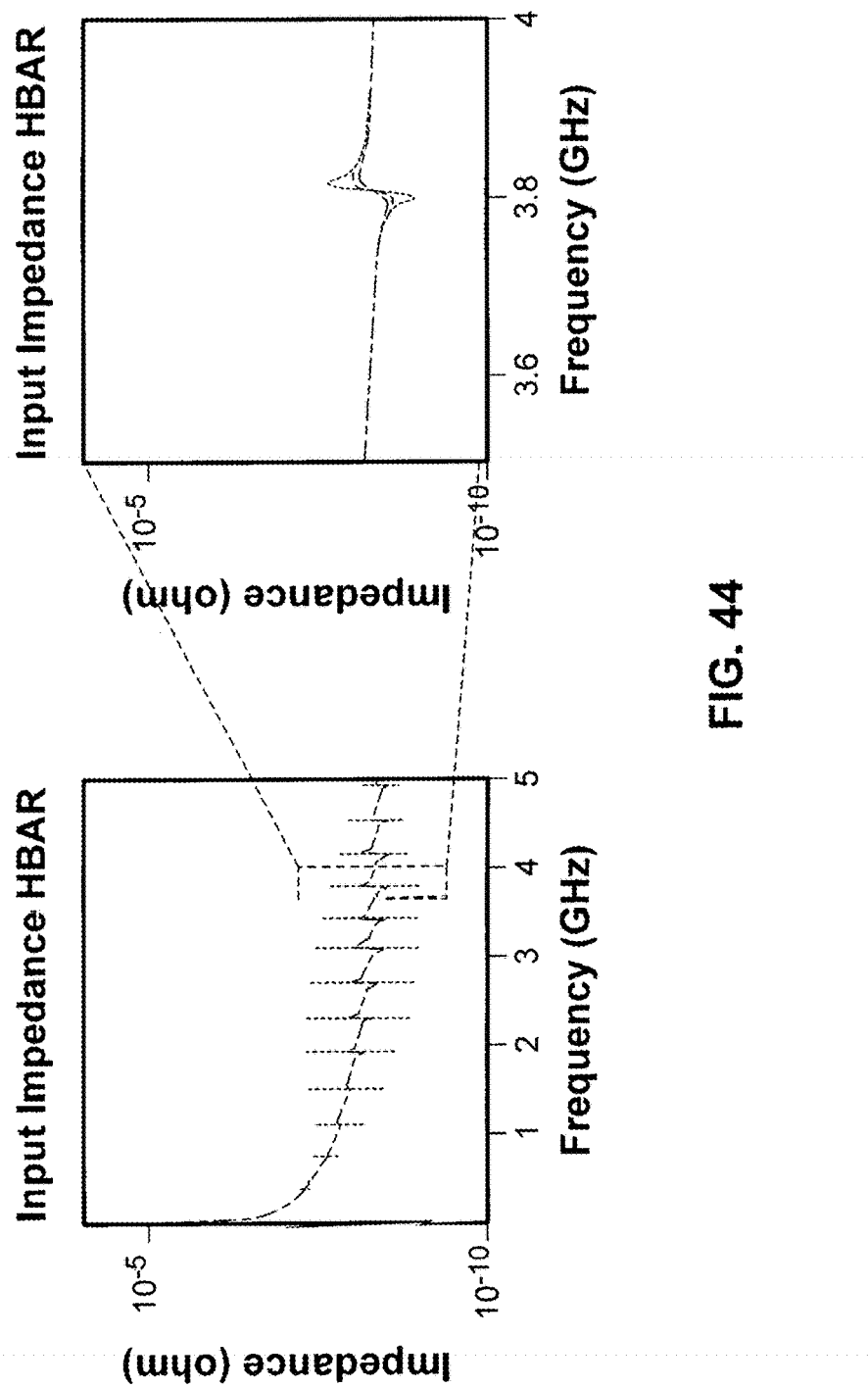
FIG. 44 shows the modeling of an HBAR with a 1 µm AlN transducer on top of a 10 µm thick silicon substrate and three loads.

If instead, we continue with the original structure the silicon layer would represent a mass load for the thin disk resonator. This structure is known as a highly over-tone bulk acoustic resonator (HBAR) since now the resonant mode is established due to the composite of the silicon and the transducer. The advantage of such a structure is that the intrinsic quality factor of silicon is much higher than that of AlN. Therefore, the composite structure has a larger quality factor than FBAR. The disadvantage is that there are many more resonant frequencies, so careful design is needed to lock to the correct one. FIG. 44 shows the modeling of an HBAR with a 1 μm AlN transducer on top of a 10 μm thick silicon substrate and three loads (air, and 2 different polymer models). Looking only at the resonant peak nearest the thickness mode of the AlN around 3.8 GHz much larger changes in quality factor are shown. A summary of the changes in quality factor are shown in Table 4.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A monolithic ultrasonic fingerprint scanner using piezoelectric transducers, comprising:
a substrate comprising a semiconductor material;
an acoustic matching layer, coupled to a backside of the substrate, to provide a surface for a finger to make contact;
a CMOS active layer attached directly on a topside of the substrate; and an array of piezoelectric transducers, solidly arranged over the CMOS active layer, wherein each of the piezoelectric transducers is operable to generate an incident acoustic wave or an incident acoustic pulse having one or more frequencies of at least 1 GHz that propagates through the substrate and toward the acoustic matching layer, wherein each of the piezoelectric transducers is operable to receive reflected acoustic waves or reflected acoustic pulses reflected from an object being detected at the surface, wherein the substrate lies below the piezoelectric transducers, wherein the acoustic matching layer lies below the substrate and above the object being detected, wherein the surface lies at a bottom of the acoustic matching layer, wherein the CMOS active layer includes a CMOS die in electrical communication with the array of piezoelectric transducers to receive and process outputs from the piezoelectric transducers produced in response to the reflected acoustic waves or the reflected acoustic pulses.

2. The monolithic ultrasonic fingerprint scanner of claim 1, wherein the incident acoustic wave or the incident acoustic pulse is able to be reflected from valleys and hills of the skin on a finger at different times with different amplitudes to create the reflected acoustic waves or the reflected acoustic pulses including echo signals of different amplitudes and delays to represent features of a fingerprint.

3. The monolithic ultrasonic fingerprint scanner of claim 1, wherein each of the piezoelectric transducers is operable to communicate with any other piezoelectric transducer in the array of piezoelectric transducers by sending proper phasing of acoustic pulses at desired angles.

4. The monolithic ultrasonic fingerprint scanner of claim 1, wherein the acoustic matching layer has a thickness of less than 10 microns.

5. The monolithic ultrasonic fingerprint scanner of claim 1, wherein the active CMOS layer includes one or more control circuits including at least one of a driving circuit, read circuit, or logic circuit including digital logic, analog logic and/or amplifiers.

6. The monolithic ultrasonic fingerprint scanner of claim 1, wherein the generated incident acoustic wave or pulse generated by each of the piezoelectric transducers has the one or more frequencies in a range of 1 GHz to 10 GHz.

7. The monolithic ultrasonic fingerprint scanner of claim 1, further comprising a layer coupled to the substrate and comprising one or mule of an inter-metal dielectric material, a metal material or a polymer material.

* * * * *

UNITED STATES PATENT AND TRADEMARK OFFICE
CERTIFICATE OF CORRECTION

| | | |
|---|---|---|
| PATENT NO. | : 10,217,045 B2 | |
| APPLICATION NO. | : 14/273540 | |
| DATED | : February 26, 2019 | |
| INVENTOR(S) | : Amit Lal et al. | |

It is certified that error appears in the above-identified patent and that said Letters Patent is hereby corrected as shown below:

In the Specification

1. In Column 1, Lines 46-47, delete "for implementing for implementing" and insert -- for implementing --, therefor.

2. In Column 2, Line 56, delete "gas" and insert -- gas. --, therefor.

3. In Column 4, Line 42, delete "pizeoresistive" and insert -- piezoresistive --, therefor.

4. In Column 5, Line 15, delete "X, and its inverse XB," and insert -- Xi and its inverse XBi --, therefor.

5. In Column 5, Line 22, delete "layer" and insert -- layer. --, therefor.

6. In Column 5, Line 30, delete "framework" and insert -- framework. --, therefor.

7. In Column 6, Lines 2-3, delete "an first" and insert -- a first --, therefor.

8. In Column 6, Line 3, delete "an neighboring" and insert -- a neighboring --, therefor.

9. In Column 7, Line 14, delete "(R&D" and insert -- (R&D) --, therefor.

10. In Column 9, Line 38, delete "depending the" and insert -- depending on the --, therefor.

11. In Column 10, Line 5, delete "lower that" and insert -- lower than --, therefor.

12. In Column 10, Line 51, delete "a ultrasound" and insert -- an ultrasound --, therefor.

13. In Column 11, Line 24, delete "k/2)," and insert -- λ/2), --, therefor.

Signed and Sealed this
First Day of October, 2019

Andrei Iancu
*Director of the United States Patent and Trademark Office*

14. In Column 16, Line 26, delete "R. Each" and insert -- Rn. Each --, therefor.

15. In Column 16, Line 32, delete "w is" and insert -- ω is --, therefor.

16. In Column 17, Line 60, delete "receive signal" and insert -- received signal --, therefor.

17. In Column 20, Line 7, delete "deposited though" and insert -- deposited through --, therefor.

18. In Column 24, Line 14, delete "various of applications." and insert -- various applications. --, therefor.

19. In Column 24, Lines 26-27, delete "for implementing for implementing" and insert -- for implementing --, therefor.

20. In Column 28, Line 39, delete "pizeoresistive" and insert -- piezoresistive --, therefor.

21. In Column 29, Lines 37-38, delete "an deposition" and insert -- a deposition --, therefor.

22. In Column 29, Line 47, delete "(D/a)" and insert -- (D/A) --, therefor.

23. In Column 30, Line 55, delete "$\sum k_i = (2N-1)ka = ks.$" and insert -- $\sum k_i = (2^N - 1)ka = ks.$ --, therefor.

24. In Column 31, Line 18, delete "X, and its inverse XB," and insert -- Xi and its inverse XBi --, therefor.

25. In Column 32, Line 18, delete "elements/actutators." and insert -- elements/actuators. --, therefor.

26. In Column 32, Line 33, delete "an desired" and insert -- a desired --, therefor.

27. In Column 36, Line 20, delete "the a cross-section" and insert -- the cross-section --, therefor.

28. In Column 39, Line 2, delete "a ion" and insert -- an ion --, therefor.

29. In Column 40, Line 16, delete "-2 m/s" and insert -- ~2 m/s --, therefor.

30. In Column 40, Line 30, delete "also been used." and insert -- also be used. --, therefor.

31. In Column 40, Lines 53-54, delete "a actuate-sense" and insert -- an actuate-sense --, therefor.

32. In Column 41, Line 66, delete "a ultrasonic" and insert -- an ultrasonic --, therefor.

33. In Column 42, Lines 44-45, delete "an desired" and insert -- a desired --, therefor.

34. In Column 42, Lines 49-50, delete "an first" and insert -- a first --, therefor.

35. In Column 42, Line 50, delete "an neighboring" and insert -- a neighboring --, therefor.

CERTIFICATE OF CORRECTION (continued)
U.S. Pat. No. 10,217,045 B2

36. In Column 44, Line 36, delete "transducer. and" and insert -- transducer and --, therefor.

In the Claims

1. In Column 48, Line 23, in Claim 7, delete "mule" and insert -- more --, therefor.